United States Patent
Cirillo et al.

(10) Patent No.: US 7,335,657 B2
(45) Date of Patent: *Feb. 26, 2008

(54) CYTOKINE INHIBITORS

(75) Inventors: Pier Francesco Cirillo, Woodbury, CT (US); Donghong Amy Gao, Hopewell Junction, NY (US); Daniel R. Goldberg, Redding, CT (US); Abdelhakim Hammach, Danbury, CT (US); Ming-Hong Hao, Ridgefield, CT (US); Victor Marc Kamhi, Danbury, CT (US); Neil Moss, Ridgefield, CT (US); Matthew Russell Netherton, Danbury, CT (US); Kevin Chungeng Qian, New Milford, CT (US); Mark Stephen Ralph, Beacon Falls, NY (US); Lifen Wu, New Milford, CT (US); Zhaoming Xiong, Danbury, CT (US); Ronald A. Aungst, Jr., Clifton Park, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/426,603

(22) Filed: Jun. 27, 2006

(65) Prior Publication Data

US 2006/0235017 A1 Oct. 19, 2006

Related U.S. Application Data

(63) Continuation of application No. 10/789,354, filed on Feb. 27, 2004, now Pat. No. 7,078,419.

(60) Provisional application No. 60/453,364, filed on Mar. 10, 2003.

(51) Int. Cl.
*A61K 31/50* (2006.01)
*A61K 43/54* (2006.01)
*C07D 239/02* (2006.01)

(52) U.S. Cl. ............ 514/249; 514/274; 514/272; 514/252.14; 544/239; 544/316; 544/123; 544/349

(58) Field of Classification Search ......... 544/239, 544/316, 123, 349; 514/274, 252.14, 272, 514/249, 239
See application file for complete search history.

(56) References Cited

U.S. PATENT DOCUMENTS 7,078,419 B2 * 7/2006 Cirillo et al. ............ 514/336

\* cited by examiner

*Primary Examiner*—Janet L. Andres
*Assistant Examiner*—Binta Robinson
(74) *Attorney, Agent, or Firm*—Michael Morris; Mary-Ellen M. Devlin; Anthony P. Bottino

(57) ABSTRACT

Disclosed are compounds of formula (I)

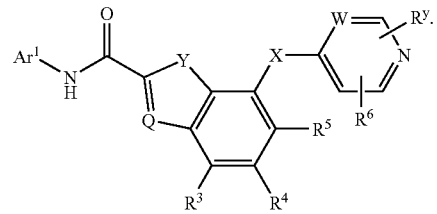

Where $Ar_1$, X, Y, Q, W, $R^3$, $R^4$, $R^5$, $R^6$ and $R^y$ are defined herein. The compounds of the invention inhibit production of cytokines involved in inflammatory processes and are thus useful for treating diseases and pathological conditions involving inflammation such as chronic inflammatory disease. The compounds are also useful for treating diseases or conditions related to oncology and anticoagulant or fibrinolytic therapy. Also disclosed are processes for preparing these compounds and pharmaceutical compositions comprising these compounds.

16 Claims, No Drawings

CYTOKINE INHIBITORS

APPLICATION DATA

This application is a continuation of U.S. application Ser. No. 10/789,354 filed Feb. 27, 2004 now U.S. Pat. No. 7,078,419 which claims benefit to U.S. provisional application No. 60/453,364 filed Mar. 10, 2003.

BACKGROUND OF THE INVENTION

1. Technical Field

This invention relates to compounds of formula (I)

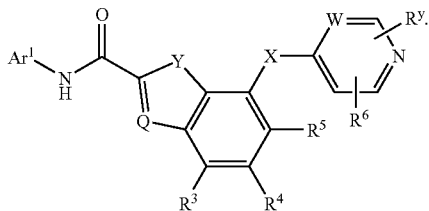

The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

2. Background Information

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al, 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., 2001 March, *Coron Artery Dis* 12(2): 107-13). An important and accepted therapeutic approach for potential drug intervention in these diseases is the reduction of proinflammatory cytokines such as TNF (also referred to in its secreted cell-free form as TNFα and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24-5, 1997). These include the treatment of rheumatoid arthritis, Crohn's disease and ulcerative colitis (Rankin, E. C. C., et al., 1997, *British J. Rheum.* 35: 334-342 and Stack, W. A., et al., 1997, *Lancet* 349: 521-524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al, 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol*. 109, 54). IL-1 and TNF are both involved in periodontal disease. The destructive process associated with periodontal disease may be due to a disregulation of both IL-1 and TNF (Howells, 1995, *Oral Dis*. 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med*., 35, 26). TNFα has also been implicated in cachexia and muscle degradation, associated with HIV infection (Lahdiverta et al., 1988, *Amer. J. Med*., 85, 289). Obesity is associated with an increase incidence of infection, diabetes and cardiovascular disease. Abnormalities in TNFα expression have been noted for each of the above conditions (Loffreda, et al., 1998, *FASEB J*. 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J*., 15, 281). Circulating TNFα may also contribute to weight loss associated with this disease (N. Takabatake et al., 2000, *Amer. J. Resp. & Crit. Care Med*., 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol*., 278, L3-12), kidney (Lemay et al., 2000, *Transplantation*, 69, 959), and the nervous system (Mitsui et al., 1999, *Brain Res*., 844, 192).

TNFα is also a potent osteoclastogenic agent and is involved in bone resorption and diseases involving bone resorption (Abu-Amer et al., 2000, *J. Biol. Chem*., 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther*., 14, 31). Cytokines including IL-1, TNF and GM-CSF have been shown to stimulate proliferation of acute myelogenous leukemia blasts (Bruserud, 1996, *Leukemia Res*. 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat*. 7, 177). Data obtained from IL-1 knock out mice indicates the critical involvement in fever for this cytokine (Kluger et al., 1998, *Clin Exp Pharmacol Physiol*. 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr*. 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol*. 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol*. 21: 487). Marked cytokine differences, such as IL-6 levels, exist in vivo between osteoclasts of normal bone and bone from patients with Paget's disease (Mills, et al., 1997, *Calcif Tissue Int*. 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther*. 1, 107). Several infectious diseases, such as influenza, indicate IL-6 and IFN alpha as key factors in both symptom formation and in host defense (Hayden, et al., 1998, *J Clin Invest*. 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci*. 6, 929). Compounds that interfered with the production of cytokines including IL-6,and TNF were effective in blocking a passive cutaneous anaphylaxis in mice (Scholz et al., 1998, *J. Med. Chem*., 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biolog* 62, 41). Bronchial asthma is characterised by an inflammatory process in lungs. Involved cytokines include GM-CSF amongst others (Lee, 1998, *J R Coll Physicians Lond* 32, 56).

Interferon γ (IFNγ) has been implicated in a number of diseases. It has been associated with increased collagen deposition that is a central histopathological feature of graft-versus-host disease (Parkman, 1998, *Curr Opin Hematol*. 5, 22). Following kidney transplantation, a patient was diagnosed with acute myelogenous leukemia.

Retrospective analysis of peripheral blood cytokines revealed elevated levels of GM-CSF and IFNγ. These elevated levels coincided with a rise in peripheral blood white cell count (Burke, et al., 1995, *Leuk Lymphoma*. 19, 173). The development of insulin-dependent diabetes (Type 1) can be correlated with the accumulation in pancreatic islet cells of T-cells producing IFNγ (Ablumunits, et al., 1998, *J Autoimmun*. 11, 73). IFNγ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol*. 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFNγ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFNγ following challenge with Vespula venom (Bonay, et al., 1997, *Clin Exp Immunol*. 109, 342). The expression of a number of cytokines, including IFNγ has been shown to increase following a delayed type hypersensitivity reaction thus indicating a role for IFNγ in atopic dermatitis (Szepietowski, et al., 1997, *Br J Dermatol*. 137, 195). Histopathologic and immunohistologic studies were performed in cases of fatal cerebral malaria. Evidence for elevated IFNγ amongst other cytokines was observed indicating a role in this disease (Udomsangpetch et al., 1997, *Am J Trop Med Hyg*. 57, 501). The importance of free radical species in the pathogenesis of various infectious diseases has been established. The nitric oxide synthesis pathway is activated in response to infection with certain viruses via the induction of proinflammatory cytokines such as IFNγ (Akaike, et al., 1998, *Proc Soc Exp Biol Med*. 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFNγ, TNF and IL-2 (Chisari, et al., 1995, *Springer Semin Immunopathol*. 17, 261). IFNγ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and post-menopausal osteoporosis (Evans, et al., 1996, *J Bone Miner Res*. 11, 300). Studies with gene deficient mice have demonstrated that the IL-12 dependent production of IFNγ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon*. 43, 277). IFNγ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther*. 10 Suppl 2, 43). An elevated level of serum IgE is associated with various atopic diseases such as bronchial asthma and atopic dermatitis. The level of IFNγ was negatively correlated with serum IgE suggesting a role for IFNγ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke. TNFα anatagonists are apparently also useful for the treatment of endometriosis, see EP 1022027 A1. Infliximab, in clinical trials for RA, has also been indicated to be useful for treating various inflammatory diseases including Behcet's disease, uveitis and ankylosing spondylitis. Pancreatitis may also be regulated by inflammatory mediator production, see J Surg Res 2000 May 15 90(2)95-101; Shock 1998 September 10(3):160-75. p38MAP kinase pathway plays an role in B.burgdorferi-elicited infammation and may be useful in treating inflammation induced by the Lyme disease agent. Anguita, J. et. al., *The Journal of Immunology*, 2002, 168: 6352-6357.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

Compounds active against p38 MAP kinase can also be useful for treating various types of cancers as described in WO 03/068223.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production with small molecule compounds will be beneficial in the treatment of various disease states.

It is therefore an object of the invention to provide compounds of formula (I)

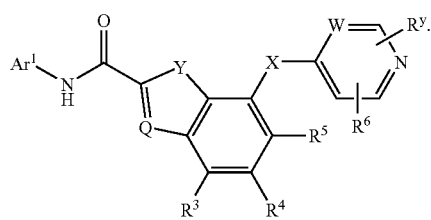

It is a further object of the invention to provide methods for treating cytokine mediated diseases and pathological conditions involving inflammation such as chronic inflammatory disease, using the novel compounds of the invention.

It is yet a further object of the invention to provide pharmaceutical compositions and processes of preparation of the above-mentioned novel compounds.

DETAILED DESCRIPTION OF THE INVENTION

In the broadest generic embodiment, there is provided compounds of the formula (I)

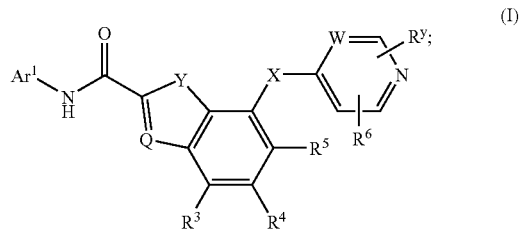

wherein:

$Ar^1$ is an aromatic carbocycle substituted with one $R^1$, and wherein $Ar^1$ is independently substituted with two $R^2$ groups and wherein one $R^1$ and one $R^2$ on adjacent ring atoms optionally form a 5- or 6-membered carbocyclic or heterocyclic ring;

$R^1$ is halogen, $NO_2$, $NH_2$, $J-N(R^a)-(CH_2)_m-$, $N(J)_2-(CH_2)_m-$, $NH_2C(O)-$, $J-N(R^a)-C(O)-$, $J-S(O)_m-N(R^a)-$, $J-N(R^a)-S(O)_m-$ or heterocycle-$(CH_2)_m-$ wherein the heterocyclic group is optionally substituted by $C_{1-5}$ alkyl;

Q is a N or $CR^p$;

Y is $>CR^pR^v$, $-CR^p=C(R^v)-$, $-O-$, $-N(R^x)-$ or $>S(O)_m$;

wherein $R^a$, $R^p$, $R^v$, $R^x$ and $R^y$ are each independently hydrogen or $C_{1-5}$ alkyl;

X is $-CH_2-$, $-N(R^a)-$, $-O-$ or $-S-$;

W is N or CH;

each m is independently 0, 1 or 2;

J is chosen from C1-10 alkyl and carbocycle each optionally substituted by $R^b$;

$R^2$ is chosen from C1-6 alkyl, C3-7 cycloalkyl optionally substituted by C1-5 alkyl, C1-4 acyl, aroyl, C1-4 alkoxy, each being optionally partially or fully halogenated, halogen, C1-6 alkoxycarbonyl, carbocyclesulfonyl and $-SO_2-CF_3$;

each $R^3$, $R^4$ and $R^5$ are independently chosen from hydrogen, C1-6 alkyl and halogen;

$R^6$ is optionally attached at a position ortho or meta to the N atom of the indicated ring, and is chosen from a bond, $-O-$, $-O-(CH_2)_{1-5}-$, $>C(O)$, $-NH-$, $-C(O)-NH-$, $-S-$, $C_{1-5}$ alkyl branched or unbranched, $C_{2-5}$ alkenyl, $C_{1-3}$ acyl, $C_{1-3}$ alkyl(OH), heterocycle selected from morpholinyl, piperazinyl, piperidinyl, pyrrolidinyl and tetrahydrofuranyl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl or aryl each alkyl, alkenyl, acyl, heterocycle, heteroaryl and aryl are optionally substituted by one to three hydroxy, oxo, $C_{1-3}$ alkyl, $C_{1-3}$ alkoxy, $C_{1-5}$ alkoxycarbonyl, $-NR_7R_8$ or $NR_7R_8-C(O)-$;

wherein each $R_6$ is further optionally covalently attached to groups chosen from:

hydrogen, $-NR_7R_8$, $C_{1-3}$ alkyl, $C_{3-6}$ cycloalkyl$C_{0-2}$alkyl, hydroxy, $C_{1-3}$ alkoxy, phenoxy, benzyloxy, aryl$C_{0-4}$ alkyl, heteroaryl $C_{0-4}$ alkyl and heterocycle $C_{0-4}$alkyl, each above-listed heterocycle, heteroaryl and aryl group is optionally substituted by one to three hydroxy, oxo, $C_{1-4}$ alkyl, $C_{1-3}$ alkoxy, $C_{1-5}$ alkoxycarbonyl, $NR_7R_8$—C(O)— or $C_{1-4}$ acyl;

each $R_7$ and $R_8$ are independently hydrogen, phenyl $C_{0-3}$alkyl optionally subtituted by halogen, $C_{1-3}$ alkyl or $diC_{1-5}$ alkyl amino, or $R_7$ and $R_8$ are $C_{1-2}$ acyl, benzoyl or $C_{1-5}$ branched or unbranched alkyl optionally substituted by $C_{1-4}$ alkoxy, hydroxy or mono or $diC_{1-3}$ alkyl amino;

and $R^b$ is chosen from hydrogen, C1-5 alkyl, hydroxy C1-5 alkyl, C2-5 alkenyl, C2-5 alkynyl, carbocycle, heterocycle, heteroaryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, or $R^b$ is chosen from C1-5 alkylsulphonylamino, hydroxy, oxo, halogen, nitro and nitrile;

or the pharmaceutically acceptable salts, acids, esters or isomers thereof

In another embodiment, there are provided compounds of the formula (I) as described above and wherein Y is —O—, —S—, —NH—, —N(CH$_2$CH$_3$)— or —N(CH$_3$)—;

X is —N(R$^a$)—, or —O—;

Q is CH;

J is chosen from C1-10 alkyl, aryl or C3-7 cycloalkyl each optionally substituted by $R^b$;

R$_2$ is independently chosen from C1-6 alkyl, C3-6 cycloalkyl optionally substituted by C1-3 alkyl, acetyl, aroyl, C1-5 alkoxy, each being optionally partially or fully halogenated, halogen, methoxycarbonyl, phenylsulfonyl and —SO$_2$—CF$_3$;

each R$^3$, R$^4$ and R$^5$ are hydrogen;

$R^b$ is chosen from hydrogen, C1-5 alkyl, C2-5 alkenyl, C2-5 alkynyl, C3-8 cycloalkyl C0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, C1-5 sulphonylamino, hydroxy, halogen, trifluoromethyl, nitro, nitrile or $R^b$ is chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

In yet another embodiment, there are provided compounds of the formula (I) as described immediately above and wherein Ar$_1$ is chosen from phenyl, naphthyl, tetrahydronaphthyl, indanyl and indenyl, each Ar$^1$ is optionally substituted with one R$^1$, and independently substituted with two R$^2$ groups;

Y is —O—, —S— or —N(CH$_3$)—;

R$^6$ is present, and is chosen from a bond, —O—, —O—(CH$_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl, pyrrolidinyl and tetrahydrofuranyl, or aryl chosen from phenyl and naphthyl, each alkyl, alkenyl, heterocycle and aryl are optionally substituted by one to three hydroxy, $C_{1-3}$ alkyl, $C_{1-3}$ alkoxy, mono or $diC_{1-3}$ alkyl amino, amino or $C_{1-5}$ alkoxycarbonyl;

wherein each R$_6$ is further optionally covalently attached to groups chosen from:

hydrogen, —NR$_7$R$_8$, $C_{1-3}$ alkyl, $C_{3-6}$ cycloalkylC$_{0-2}$alkyl, hydroxy, $C_{1-3}$ alkoxy, phenoxy, benzyloxy, phenylC$_{0-4}$ alkyl, piperazinylC$_{0-4}$ alkyl, piperidinylC$_{0-4}$alkyl, pyrrolidinylC$_{0-4}$ alkyl, morpholinylC$_{0-4}$ alkyl, tetrahydrofuranylC$_{0-4}$ alkyl, triazolyl C$_{0-4}$alkyl, imidazolyl C$_{0-4}$alkyl and pyridinyl C$_{0-4}$alkyl, each abovelisted heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, —NR$_7$R$_8$, NR$_7$R$_8$—C(O)— or $C_{1-4}$ acyl;

each R$_7$ and R$_8$ are independently hydrogen, phenylC$_{0-3}$ alkyl optionally subtituted by halogen, $C_{1-3}$ alkyl or $diC_{1-5}$ alkyl amino, or R$_7$ and R$_8$ are $C_{1-2}$ acyl, benzoyl or $C_{1-5}$ branched or unbranched alkyl optionally substituted by $C_{1-4}$ alkoxy, hydroxy or mono or $diC_{1-3}$ alkyl amino.

In yet another embodiment, there are provided compounds of the formula (I) as described immediately above and wherein X is —O—;

Y is —N(CH$_3$)—;

J is C1-10 alkyl optionally substituted by $R^b$;

R$_2$ is independently chosen from C1-6 alkyl, C3-6 cycloalkyl optionally substituted by C1-3 alkyl and C1-5 alkoxy, each being optionally be partially or fully halogenated;

R$^6$ is chosen from a bond, —O—, —O—(CH$_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl and pyrrolidinyl or phenyl, each alkyl, alkenyl, heterocycle and phenyl are optionally substituted by one to three hydroxy, $C_{1-3}$ alkyl, $C_{1-3}$ alkoxy, mono or $diC_{1-3}$ alkyl amino, amino or $C_{1-5}$ alkoxycarbonyl;

wherein each R$_6$ is further optionally covalently attached to groups chosen from:

hydrogen, —NR$_7$R$_8$, $C_{1-3}$ alkyl, $C_{3-6}$ cycloalkylC$_{0-2}$alkyl, benzyloxy, phenylC$_{0-4}$ alkyl, piperazinylC$_{0-4}$ alkyl, piperidinyl C$_{0-4}$alkyl, pyrrolidinylC$_{0-4}$ alkyl, morpholinylC$_{0-4}$ alkyl, triazolyl C$_{0-4}$alkyl, imidazolyl C$_{0-4}$alkyl and pyridinyl C$_{0-4}$alkyl, each above-listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, amino, NR$_7$R$_8$—C(O)— or $C_{1-4}$ acyl;

each R$_7$ and R$_8$ are independently hydrogen, phenylC$_{0-2}$ alkyl optionally subtituted by halogen, $C_{1-3}$ alkyl or $diC_{1-5}$ alkyl amino, or $R_7$ and $R_8$ are $C_{1-5}$ branched or unbranched alkyl optionally substituted by $C_{1-4}$ alkoxy, hydroxy or mono or $diC_{1-3}$ alkyl amino;

$R^b$ is chosen from hydrogen, C1-5 alkyl, C3-7 cycloalkylC0-2 alkyl, aryl, C1-5 alkoxy, amino, C1-5 alkylamino, C1-3 dialkylamino, C1-3 acyl, C1-5 alkoxycarbonyl, C1-3 acyloxy, C1-3 acylamino, C1-3 sulphonylamino, hydroxy, halogen, trifluoromethyl, nitro, nitrile;

or $R^b$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl.

In yet still another embodiment, there are provided compounds of the formula (J) as described immediately above and wherein
$Ar^1$ is formula (A) or (B)

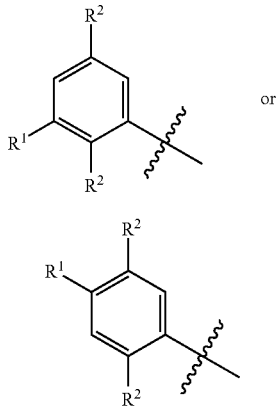

wherein:

when $Ar^1$ is formula (A) then:
$R^1$ is $NH_2$, J-N($R^a$)—($CH_2$)$_m$—, $NH_2C(O)$—, J-N($R^a$)—C(O)—, J-S(O)$_2$—N($R^a$)—, J-N($R^a$)—S(O)$_2$— or heterocycle-($CH_2$)$_{1-2}$— wherein the heterocycle is chosen from pyrrolidinyl, morpholinyl and piperazinyl each optionally substituted by C1-4 alkyl, and
J is $C_{1-5}$ alkyl optionally substituted by $R^b$;

or when $Ar^1$ is formula (B) then:
$R^1$ is hydrogen or halogen;
$R_2$ is independently chosen from C1-5 alkyl, C3-6 cycloalkyl optionally substituted by C1-3 alkyl and C1-5 alkoxy, each being optionally partially or fully halogenated;
$R^6$ is chosen from a bond, —O—, —O—($CH_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl and pyrrolidinyl or phenyl, each alkyl, alkenyl, heterocycle and phenyl are optionally substituted by one to three hydroxy, $C_{1-3}$ alkyl, $C_{1-3}$ alkoxy, mono or $diC_{1-3}$ alkyl amino, amino or $C_{1-5}$ alkoxycarbonyl;

wherein each $R_6$ is further optionally covalently attached to groups chosen from:

hydrogen, —$NR_7R_8$, $C_{1-3}$ alkyl, $C_{3-6}$ cycloalkyl$C_{0-2}$alkyl, benzyloxy, phenyl$C_{0-4}$ alkyl, piperazinyl, piperazinyl$C_{1-2}$ alkyl, piperidinyl, piperidinyl $C_{1-2}$alkyl, pyrrolidinyl, pyrrolidinyl $C_{1-2}$ alkyl, morpholinyl, morpholinyl$C_{1-2}$ alkyl, triazolyl, triazolyl $C_{1-2}$alkyl, imidazolyl, imidazolyl $C_{1-2}$alkyl, pyridinyl and pyridinyl $C_{1-2}$alkyl, each above-listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, amino, $NR_7R_8$—C(O)— or $C_{1-4}$ acyl.

In yet still another embodiment, there are provided compounds of the formula (I) as described immediately above and wherein
$Ar^1$ is formula (A) or (B)

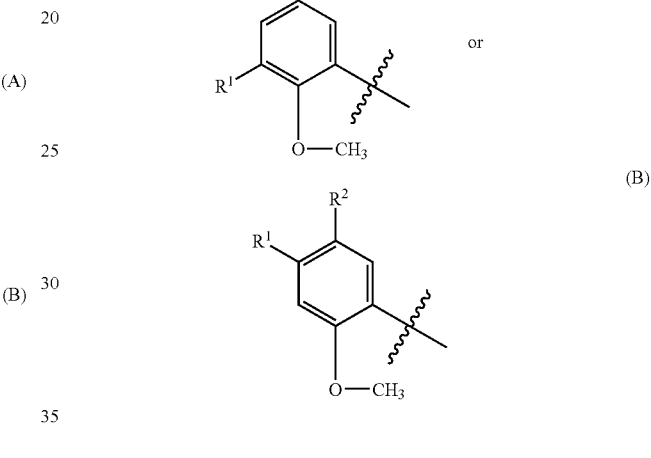

and $R^2$ is chosen from

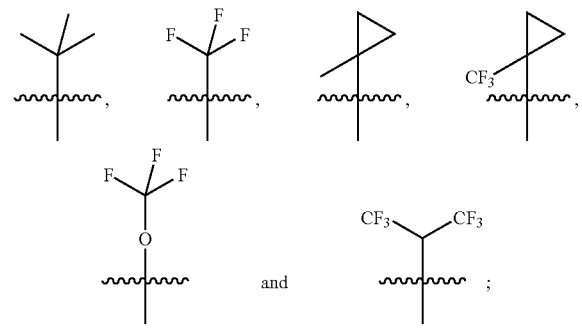

when $Ar^1$ is formula (A) then:

when $R^1$ is J-S(O)$_2$—N($R^a$)— or J-N($R^a$)—S(O)$_2$— then J is $C_{1-3}$ alkyl;

and when $R^1$ is $NH_2$, J-N($R^a$)—($CH_2$)$_m$—, $NH_2C(O)$—, J-N($R^a$)—C(O)—, or heterocycle-($CH_2$)$_{1-2}$— wherein the heterocycle is chosen from pyrrolidinyl, morpholinyl, piperazinyl or C1-4alkylpiperazinyl, then
J is C1-3 alkyl optionally substituted by $R^b$.

In yet another embodiment, there are provided compounds of the formula (I) as described immediately above and wherein $R^b$ is chosen from hydrogen, C1-5 alkyl, C3-6 cycloalkylC0-2 alkyl, phenyl, C1-5 alkoxy, amino, C1-5 alkylamino, C1-3 dialkylamino, C1-3 acyl, C1-5 alkoxycarbonyl, C1-3 acyloxy, C1-3 acylamino, hydroxy, halogen;

or $R^b$ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl.

In yet another embodiment, there are provided compounds of the formula (I) as described immediately above and wherein $R^b$ is chosen from amino, C1-5 alkylamino, C1-3 dialkylamino;

or $R^b$ is chosen morpholinyl, piperidinyl and pyridinyl.

In yet still another embodiment, there are provided compounds of the formula (I) as described immediately above and wherein $Ar^1$ is formula (A).

In yet still another embodiment, there are provided compounds of the formula (I) as described above and wherein $Ar^1$ is formula (B).

In yet another embodiment, there are provided compounds of the formula (I) as described above and wherein $Ar^1$ is

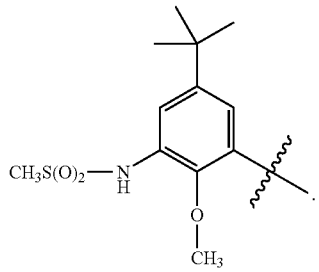

The following are representative compounds of the invention which have been made according to the general schemes and working examples below:

TABLE I

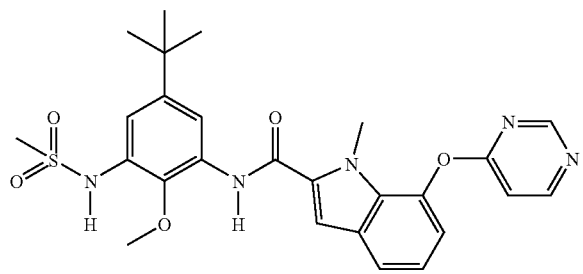

1-Methyl-7-(pyrimidin-4-yloxy)-1H-indole-2-carboxylic acid (5-tert-butyl-3-methanesulfonylamino-2-methoxy-phenyl)-amide

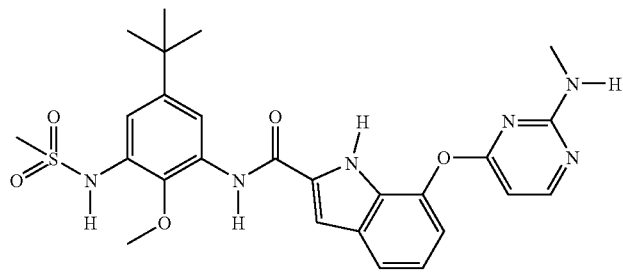

7-(2-Methylamino-pyrimidin-4-yloxy)-1H-indole-2-carboxylic acid (5-tert-butyl-3-methanesulfonylamino-2-methoxy-phenyl)-amide

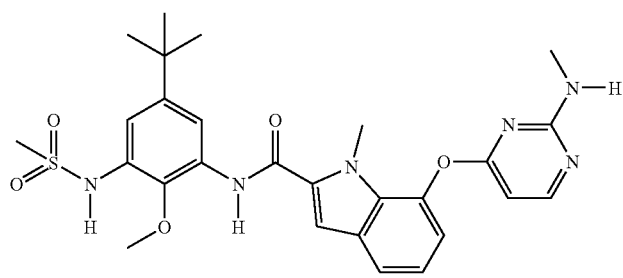

1-Methyl-7-(2-methylamino-pyrimidin-4-yloxy)-1H-indole-2-carboxylic acid (5-tert-butyl-3-methanesulfonylamino-2-methoxy-phenyl)-amide TABLE I-continued

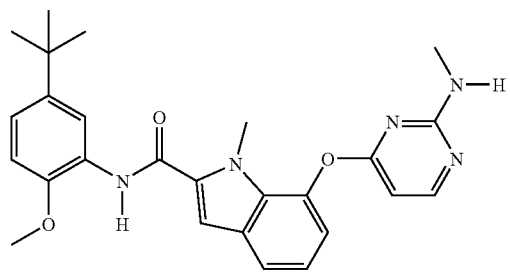

1-Methyl-7-(2-methylamino-pyrimidin-4-yloxy)-1H-indole-2-carboxylic acid (5-tert-butyl-2-methoxy-phenyl)-amide

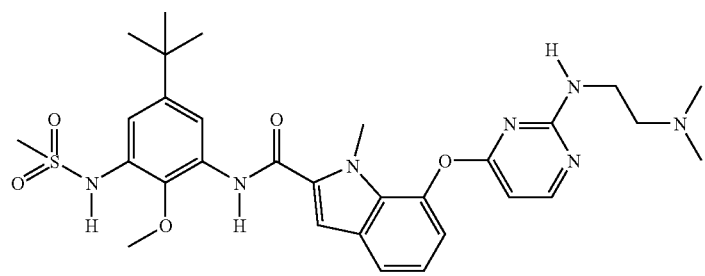

7-[2-(2-Dimethylamino-ethylamino)-pyrimidin-4-yloxy]-1-methyl-1H-indole-2-carboxylic acid (5-tert-butyl-3-methanesulfonylamino-2-methoxy-phenyl)-amide

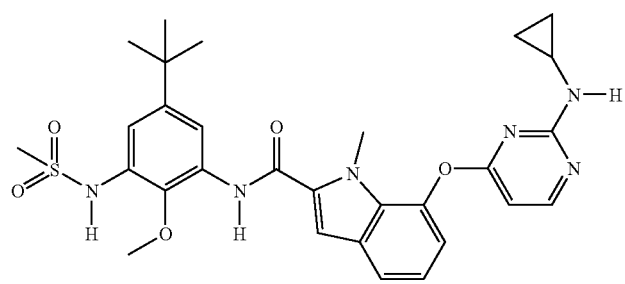

7-(2-Cyclopropylamino-pyrimidin-4-yloxy)-1-methyl-1H-indole-2-carboxylic acid (5-tert-butyl-3-methanesulfonylamino-2-methoxy-phenyl)-amide

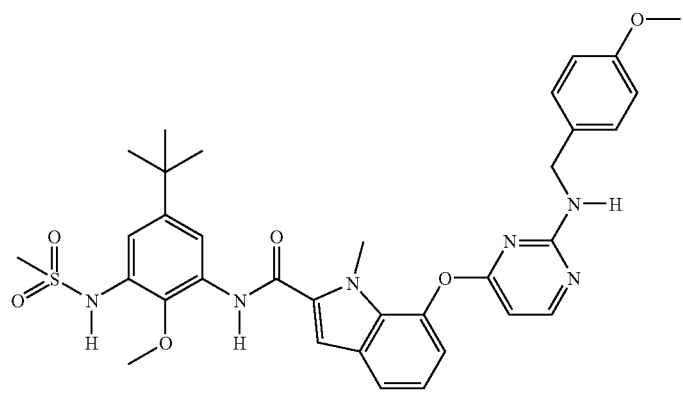

7-[2-(4-Methoxy-benzylamino)-pyrimidin-4-yloxy]-1-methyl-1H-indole-2-carboxylic acid (5-tert-butyl-3-methanesulfonylamino-2-methoxy-phenyl)-amide

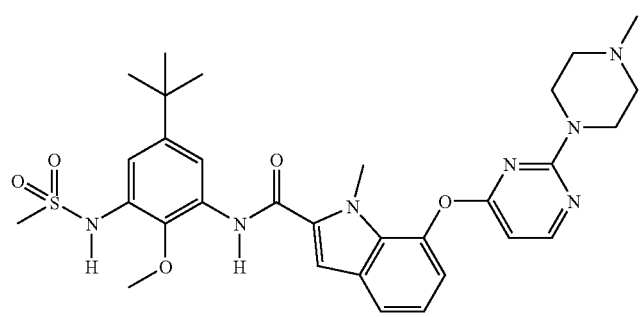

1-Methyl-7-[2-(4-methyl-piperazin-1-yl)-pyrimidin-4-yloxy]-1H-indole-2-carboxylic acid (5-tert-butyl-3-methanesulfonylamino-2-methoxy-phenyl)-amide TABLE I-continued

| Structure | Name |
|---|---|
| 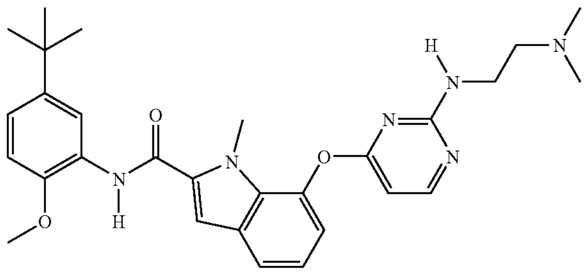 | 7-[2-(2-Dimethylamino-ethylamino)-pyrimidin-4-yloxy]-1-methyl-1H-indole-2-carboxylic acid (5-tert-butyl-2-methoxy-phenyl)-amide |
| 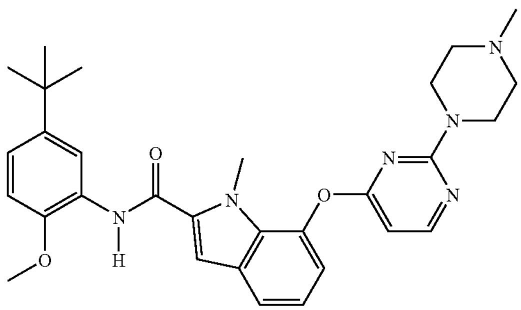 | 1-Methyl-7-[2-(4-methyl-piperazin-1-yl)-pyrimidin-4-yloxy]-1H-indole-2-carboxylic acid (5-tert-butyl-2-methoxy-phenyl)-amide |
| 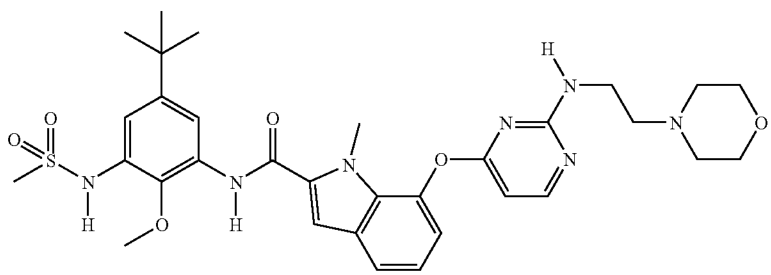 | 1-Methyl-7-[2-(2-morpholin-4-yl-ethylamino)-pyrimidin-4-yloxy]-1H-indole-2-carboxylic acid (5-tert-butyl-3-methanesulfonylamino-2-methoxy-phenyl)-amide |
| 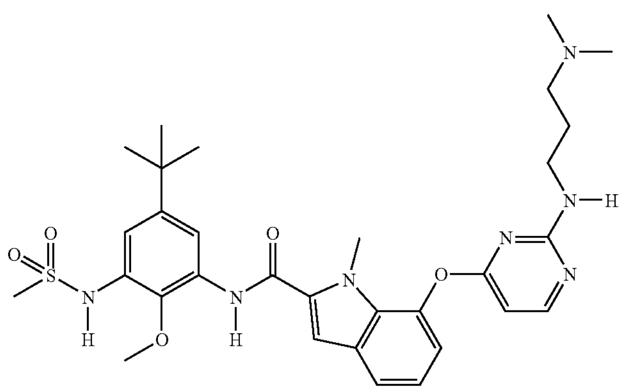 | 7-[2-(3-Dimethylamino-propylamino)-pyrimidin-4-yloxy]-1-methyl-1H-indole-2-carboxylic acid (5-tert-butyl-3-methanesulfonylamino-2-methoxy-phenyl)-amide |
| 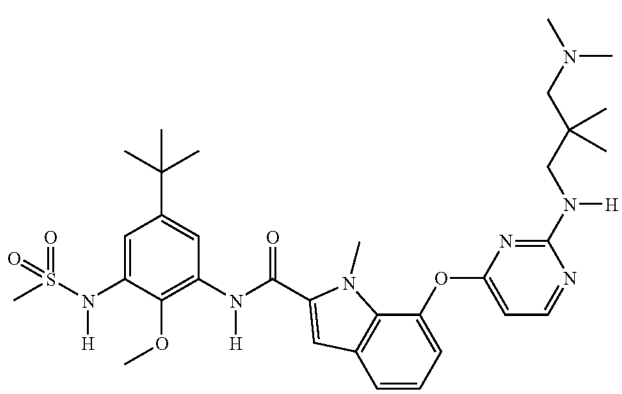 | 7-[2-(3-Dimethylamino-2,2-dimethyl-propylamino)-pyrimidin-4-yloxy]-1-methyl-1H-indole-2-carboxylic acid (5-tert-butyl-3-methanesulfonylamino-2-methoxy-phenyl)-amide |

TABLE I-continued

| Structure | Name |
|---|---|
| (structure) | 7-(2-Dimethylamino-pyrimidin-4-yloxy)-1-methyl-1H-indole-2-carboxylic acid (5-tert-butyl-3-methanesulfonylamino-2-methoxy-phenyl)-amide |
| (structure) | 1-Methyl-7-(6-methyl-2-methylamino-pyrimidin-4-yloxy)-1H-indole-2-carboxylic acid (5-tert-butyl-3-methanesulfonylamino-2-methoxy-phenyl)-amide |
| (structure) | 1-Methyl-7-[2-(2-pyrrolidin-1-yl-ethylamino)-pyrimidin-4-yloxy]-1H-indole-2-carboxylic acid (5-tert-butyl-3-methanesulfonylamino-2-methoxy-phenyl)-amide |
| (structure) | 1-Methyl-7-[2-(piperidin-4-ylamino)-pyrimidin-4-yloxy]-1H-indole-2-carboxylic acid (5-tert-butyl-3-methanesulfonylamino-2-methoxy-phenyl)-amide |
| (structure) | 4-{4-[2-(5-tert-Butyl-3-methanesulfonylamino-2-methoxy-phenylcarbamoyl)-1-methyl-1H-indol-7-yloxy]-pyrimidin-2-ylamino}-piperidine-1-carboxylic acid tert-butyl ester |

TABLE I-continued

| Structure | Name |
|---|---|
| 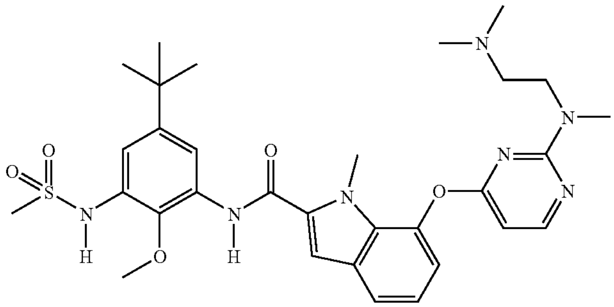 | 7-{2-[(2-Dimethylamino-ethyl)-methyl-amino]-pyrimidin-4-yloxy}-1-methyl-1H-indole-2-carboxylic acid (5-tert-butyl-3-methanesulfonylamino-2-methoxy-phenyl)-amide |
| 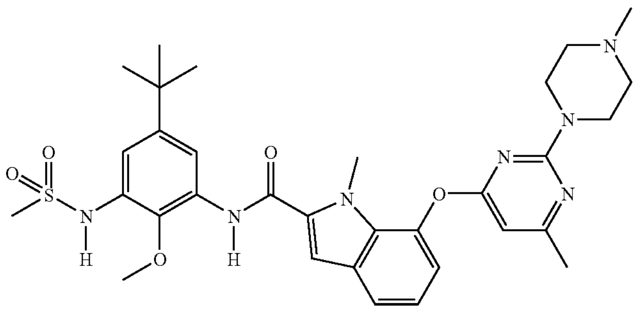 | 1-Methyl-7-[6-methyl-2-(4-methyl-piperazin-1-yl)-pyrimidin-4-yloxy]-1H-indole-2-carboxylic acid (5-tert-butyl-3-methanesulfonylamino-2-methoxy-phenyl)-amide |
| 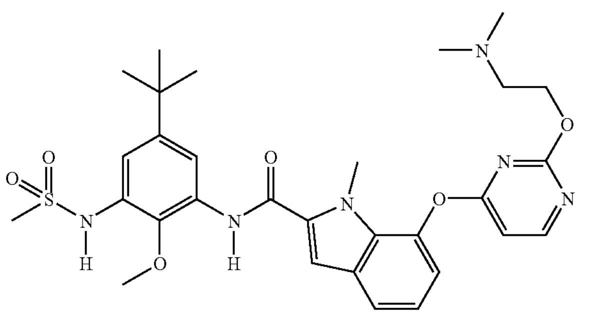 | 7-[2-(2-Dimethylamino-ethoxy)-pyrimidin-4-yloxy]-1-methyl-1H-indole-2-carboxylic acid (5-tert-butyl-3-methanesulfonylamino-2-methoxy-phenyl)-amide |
| 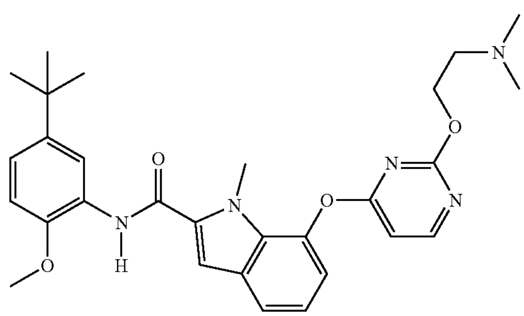 | 7-[2-(2-Dimethylamino-ethoxy)-pyrimidin-4-yloxy]-1-methyl-1H-indole-2-carboxylic acid (5-tert-butyl-2-methoxy-phenyl)-amide |
| 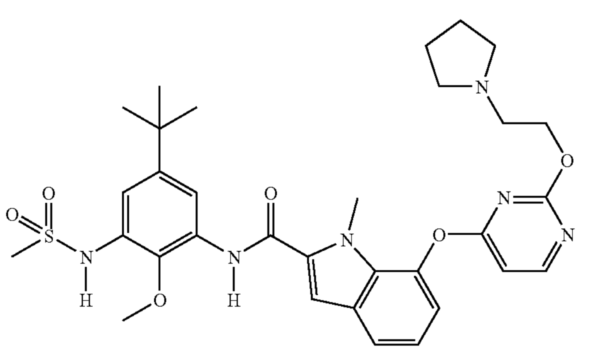 | 1-Methyl-7-[2-(2-pyrrolidin-1-yl-ethoxy)-pyrimidin-4-yloxy]-1H-indole-2-carboxylic acid (5-tert-butyl-3-methanesulfonylamino-2-methoxy-phenyl)-amide |

TABLE I-continued

| Structure | Name |
|---|---|
| (structure) | 1-Methyl-7-[2-(2-morpholin-4-yl-ethoxy)-pyrimidin-4-yloxy]-1H-indole-2-carboxylic acid (5-tert-butyl-3-methanesulfonylamino-2-methoxy-phenyl)-amide |
| (structure) | 1-Methyl-7-[2-(1-methyl-piperidin-4-yloxy)-pyrimidin-4-yloxy]-1H-indole-2-carboxylic acid (5-tert-butyl-3-methanesulfonylamino-2-methoxy-phenyl)-amide |
| (structure) | 7-[2-(2-Dimethylamino-ethoxy)-6-methyl-pyrimidin-4-yloxy]-1-methyl-1H-indole-2-carboxylic acid (5-tert-butyl-3-methanesulfonylamino-2-methoxy-phenyl)-amide |
| (structure) | 1-Methyl-7-(2-methylcarbamoyl-pyridin-4-yloxy)-1H-indole-2-carboxylic acid [5-tert-butyl-3-(2-dimethylamino-ethylcarbamoyl)-2-methoxy-phenyl]-amide |

TABLE I-continued

| Structure | Name |
|---|---|
| (structure) | 7-[2-(2-Dimethylamino-ethylcarbamoyl)-pyridin-4-yloxy]-1-methyl-1H-indole-2-carboxylic acid (5-tert-butyl-3-methanesulfonylamino-2-methoxy-phenyl)-amide |
| (structure) | 1-Methyl-7-(2-methylamino-pyrimidin-4-yloxy)-1H-indole-2-carboxylic acid [5-tert-butyl-3-(2-dimethylamino-ethylcarbamoyl)-2-methoxy-phenyl]-amide |
| (structure) | 1-Methyl-7-(2-methylamino-pyrimidin-4-yloxy)-1H-indole-2-carboxylic acid [5-tert-butyl-2-methoxy-3-(2-morpholin-4-yl-ethylcarbamoyl)-phenyl]-amide |
| (structure) | 1-Methyl-7-(2-methylamino-pyrimidin-4-yloxy)-1H-indole-2-carboxylic acid (5-tert-butyl-3-carbamoyl-2-methoxy-phenyl)-amide |
| (structure) | 1-Methyl-7-(2-methylamino-pyrimidin-4-yloxy)-1H-indole-2-carboxylic acid (5-tert-butyl-2-methoxy-3-methylcarbamoyl-phenyl)-amide |

TABLE I-continued

| Structure | Name |
|---|---|
| 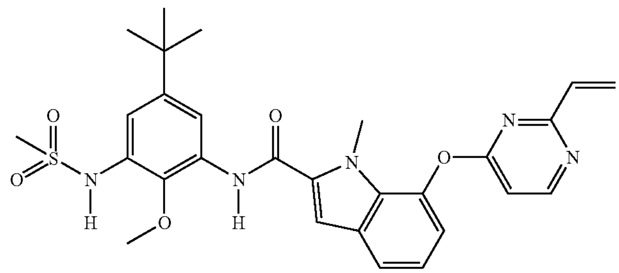 | 1-Methyl-7-(2-vinyl-pyrimidin-4-yloxy)-1H-indole-2-carboxylic acid (5-tert-butyl-3-methanesulfonylamino-2-methoxy-phenyl)-amide |
| 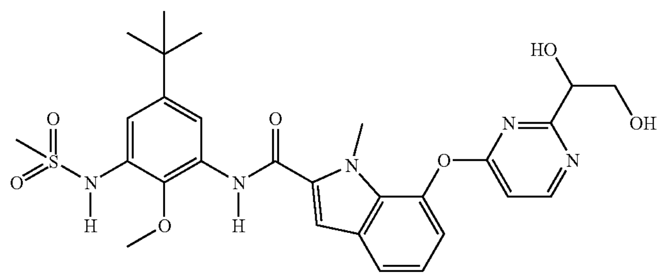 | 7-[2-(1,2-Dihydroxy-ethyl)-pyrimidin-4-yloxy]-1-methyl-1H-indole-2-carboxylic acid (5-tert-butyl-3-methanesulfonylamino-2-methoxy-phenyl)-amide |
| 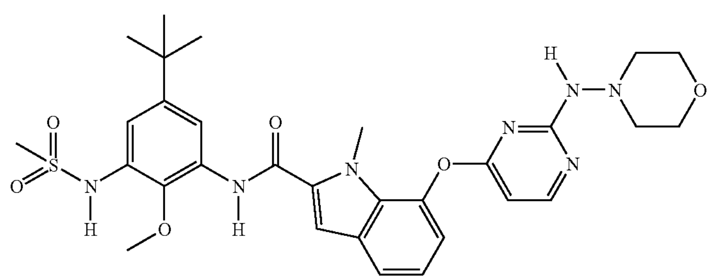 | 1-Methyl-7-[2-(morpholin-4-ylamino)-pyrimidin-4-yloxy]-1H-indole-2-carboxylic acid (5-tert-butyl-3-methanesulfonylamino-2-methoxy-phenyl)-amide |
| 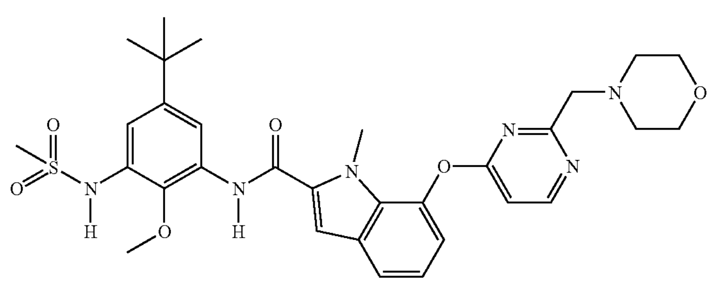 | 1-Methyl-7-(2-morpholin-4-ylmethyl-pyrimidin-4-yloxy)-1H-indole-2-carboxylic acid (5-tert-butyl-3-methanesulfonylamino-2-methoxy-phenyl)-amide |
| 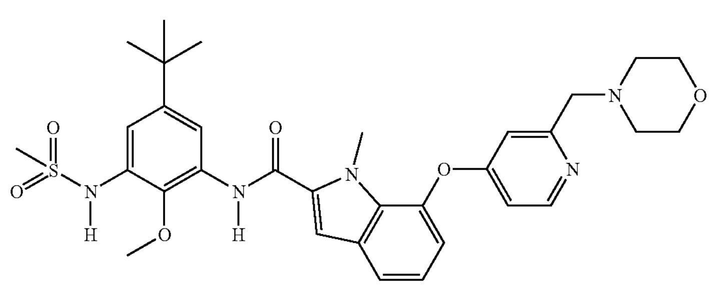 | 1-Methyl-7-(2-morpholin-4-ylmethyl-pyridin-4-yloxy)-1H-indole-2-carboxylic acid (5-tert-butyl-3-methanesulfonylamino-2-methoxy-phenyl)-amide |

TABLE I-continued

| Structure | Name |
|---|---|
| 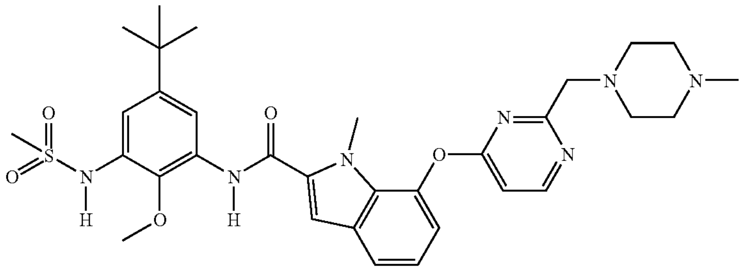 | 1-Methyl-7-[2-(4-methyl-piperazin-1-ylmethyl)-pyrimidin-4-yloxy]-1H-indole-2-carboxylic acid (5-tert-butyl-3-methanesulfonylamino-2-methoxy-phenyl)-amide |
| 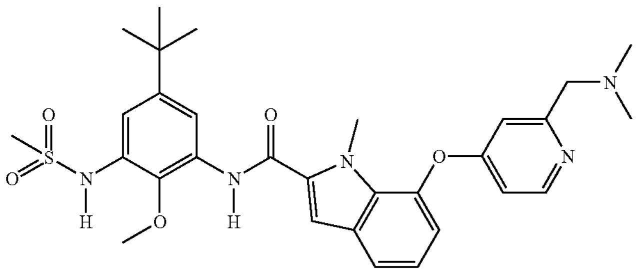 | 7-(2-Dimethylaminomethyl-pyridin-4-yloxy)-1-methyl-1H-indole-2-carboxylic acid (5-tert-butyl-3-methanesulfonylamino-2-methoxy-phenyl)-amide |
| 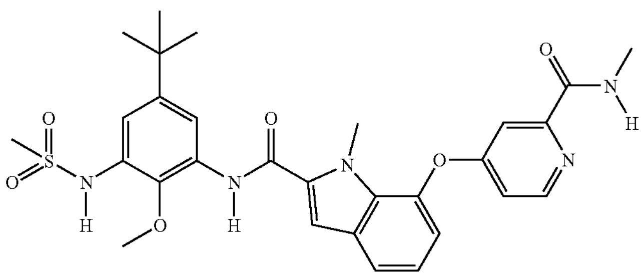 | 1-Methyl-7-(2-methylcarbamoyl-pyridin-4-yloxy)-1H-indole-2-carboxylic acid (5-tert-butyl-3-methanesulfonylamino-2-methoxy-phenyl)-amide |
| 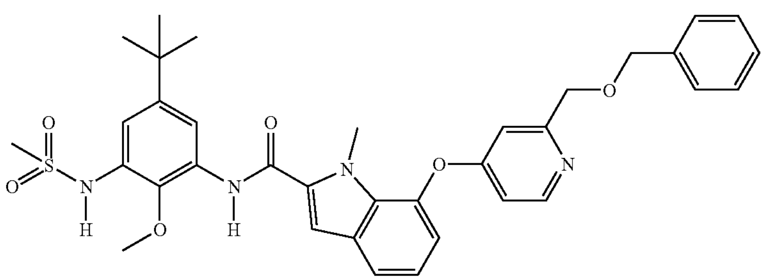 | 7-(2-Benzyloxymethyl-pyridin-4-yloxy)-1-methyl-1H-indole-2-carboxylic acid (5-tert-butyl-3-methanesulfonylamino-2-methoxy-phenyl)-amide |
| 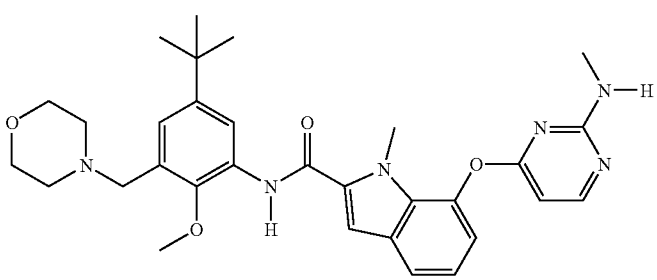 | 1-Methyl-7-(2-methylamino-pyrimidin-4-yloxy)-1H-indole-2-carboxylic acid (5-tert-butyl-2-methoxy-3-morpholin-4-ylmethyl-phenyl)-amide |

TABLE I-continued

| | |
|---|---|
| 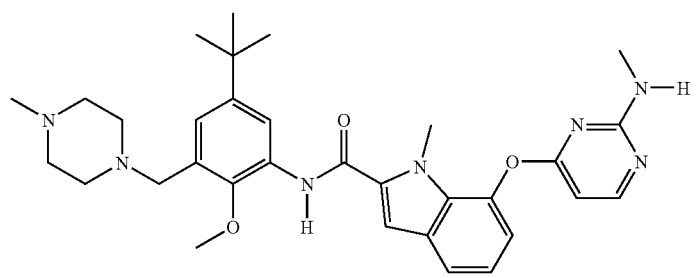 | 1-Methyl-7-(2-methylamino-pyrimidin-4-yloxy)-1H-indole-2-carboxylic acid [5-tert-butyl-2-methoxy-3-(4-methyl-piperazin-1-ylmethyl)-phenyl]-amide |
| 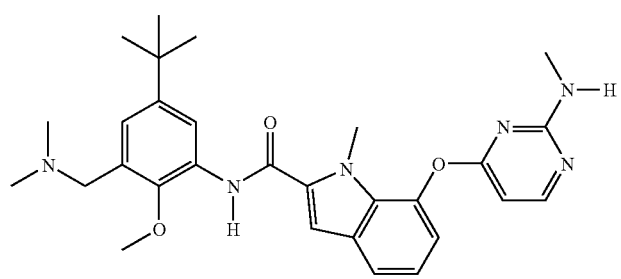 | 1-Methyl-7-(2-methylamino-pyrimidin-4-yloxy)-1H-indole-2-carboxylic acid (5-tert-butyl-3-dimethylaminomethyl-2-methoxy-phenyl)-amide |
| 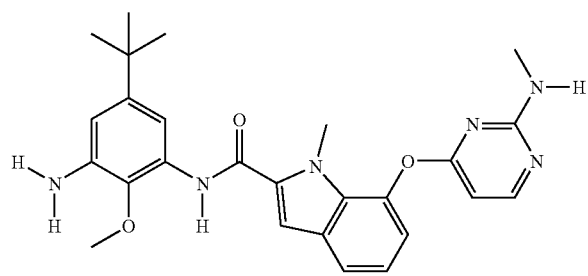 | 1-Methyl-7-(2-methylamino-pyrimidin-4-yloxy)-1H-indole-2-carboxylic acid (3-amino-5-tert-butyl-2-methoxy-phenyl)-amide |
| 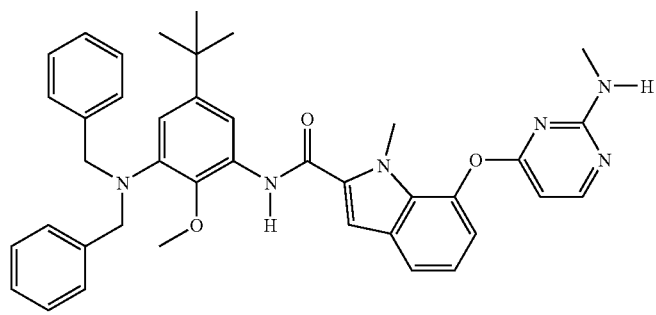 | 1-Methyl-7-(2-methylamino-pyrimidin-4-yloxy)-1H-indole-2-carboxylic acid (5-tert-butyl-3-dibenzylamino-2-methoxy-phenyl)-amide |
| 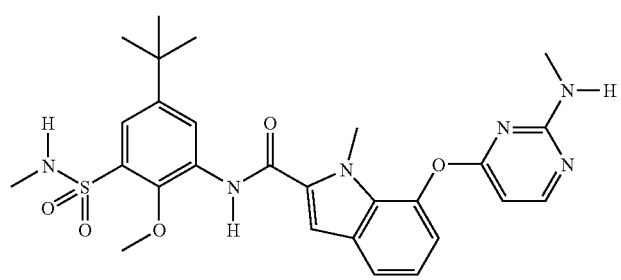 | 1-Methyl-7-(2-methylamino-pyrimidin-4-yloxy)-1H-indole-2-carboxylic acid (5-tert-butyl-2-methoxy-3-methylsulfamoyl-phenyl)-amide |

TABLE I-continued

| Structure | Name |
|---|---|
| | 7-[2-(2-Dimethylamino-ethylamino)-pyrimidin-4-yloxy]-1-methyl-1H-indole-2-carboxylic acid (5-tert-butyl-3-[1,3]dioxolan-2-yl-2-methoxy-phenyl)-amide |
| | 1-Methyl-7-[2-(4-methyl-piperazin-1-yl)-pyrimidin-4-yloxy]-1H-indole-2-carboxylic acid (5-tert-butyl-2-methoxy-3-methylaminomethyl-phenyl)-amide |
| | 1-Methyl-7-[2-(4-methyl-piperazin-1-yl)-pyrimidin-4-yloxy]-1H-indole-2-carboxylic acid (5-tert-butyl-2-methoxy-3-pyrrolidin-1-ylmethyl-phenyl)-amide |
| | 1-Methyl-7-{2-[methyl-(1-methyl-piperidin-4-yl)-amino]-pyrimidin-4-yloxy}-1H-indole-2-carboxylic acid (5-tert-butyl-3-methanesulfonylamino-2-methoxy-phenyl)-amide |
| | 7-(2-Hydroxymethyl-pyridin-4-yloxy)-1-methyl-1H-indole-2-carboxylic acid (5-tert-butyl-3-methanesulfonylamino-2-methoxy-phenyl)-amide and |

TABLE I-continued

| | |
|---|---|
| 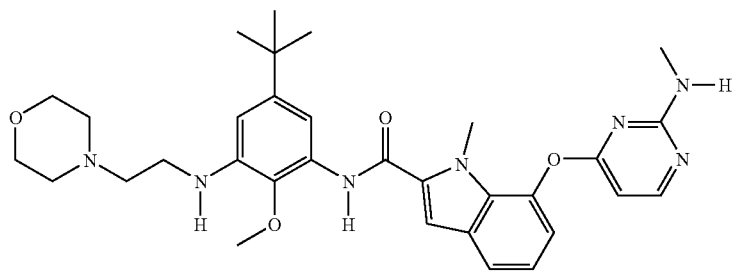 | 1-Methyl-7-(2-methylamino-pyrimidin-4-yloxy)-1H-indole-2-carboxylic acid [5-tert-butyl-2-methoxy-3-(2-morpholin-4-yl-ethylamino)-phenyl]-amide |
| 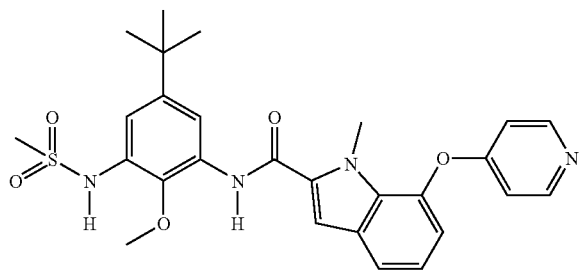 | 1-Methyl-7-(pyridin-4-yloxy)-1H-indole-2-carboxylic acid (5-tert-butyl-3-methanesulfonylamino-2-methoxy-phenyl)-amide |
| 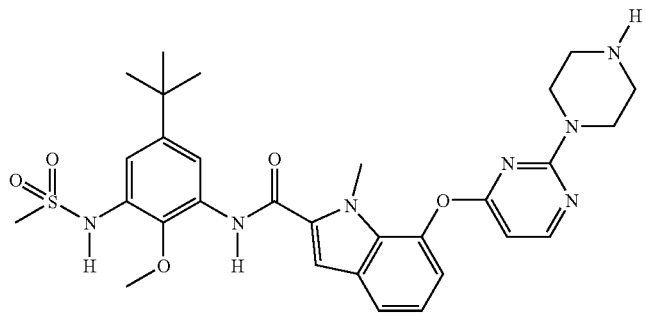 | 1-Methyl-7-(2-piperazin-1-yl-pyrimidin-4-yloxy)-1H-indole-2-carboxylic acid (5-tert-butyl-3-methanesulfonylamino-2-methoxy-phenyl)-amide |
| 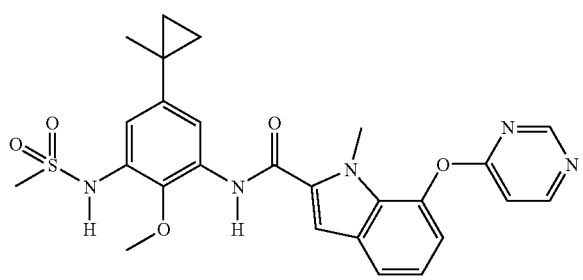 | 1-Methyl-7-(pyrimidin-4-yloxy)-1H-indole-2-carboxylic acid [3-methanesulfonylamino-2-methoxy-5-(1-methyl-cyclopropyl)-phenyl]-amide |
| 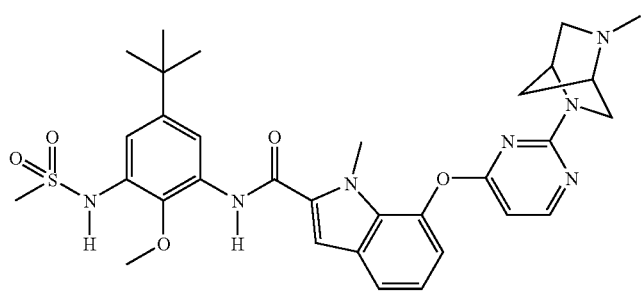 | 1-Methyl-7-[2-(5-methyl-2,5-diaza-bicyclo[2.2.1]hept-2-yl)-pyrimidin-4-yloxy]-1H-indole-2-carboxylic acid (5-tert-butyl-3-methanesulfonylamino-2-methoxy-phenyl)-amide |

TABLE I-continued

| | |
|---|---|
| 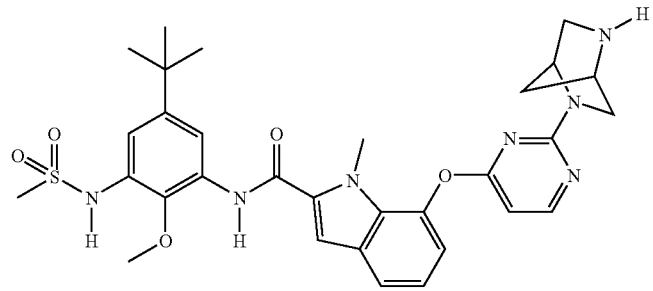 | 7-[2-(2,5-Diaza-bicyclo[2.2.1]hept-2-yl)-pyrimidin-4-yloxy]-1-methyl-1H-indole-2-carboxylic acid (5-tert-butyl-3-methanesulfonylamino-2-methoxy-phenyl)-amide |
| 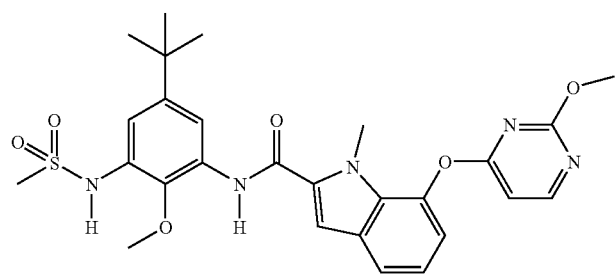 | 7-(2-Methoxy-pyrimidin-4-yloxy)-1-methyl-1H-indole-2-carboxylic acid (5-tert-butyl-3-methanesulfonylamino-2-methoxy-phenyl)-amide |
| 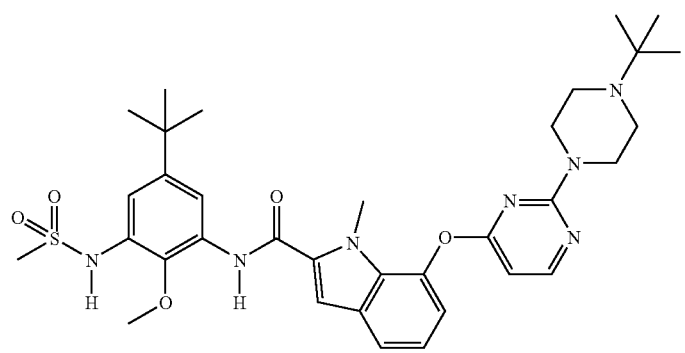 | 7-[2-(4-tert-Butyl-piperazin-1-yl)-pyrimidin-4-yloxy]-1-methyl-1H-indole-2-carboxylic acid (5-tert-butyl-3-methanesulfonylamino-2-methoxy-phenyl)-amide |
| 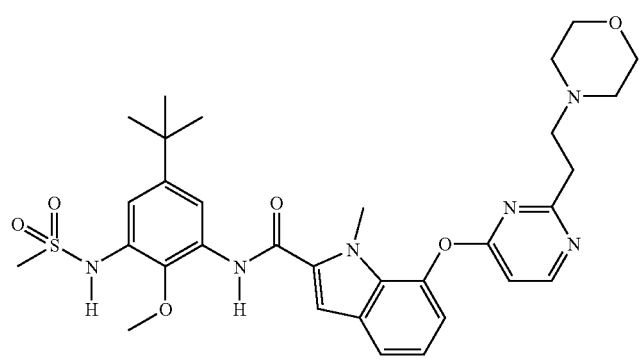 | 1-Methyl-7-[2-(2-morpholin-4-yl-ethyl)-pyrimidin-4-yloxy]-1H-indole-2-carboxylic acid (5-tert-butyl-3-methanesulfonylamino-2-methoxy-phenyl)-amide |

TABLE I-continued

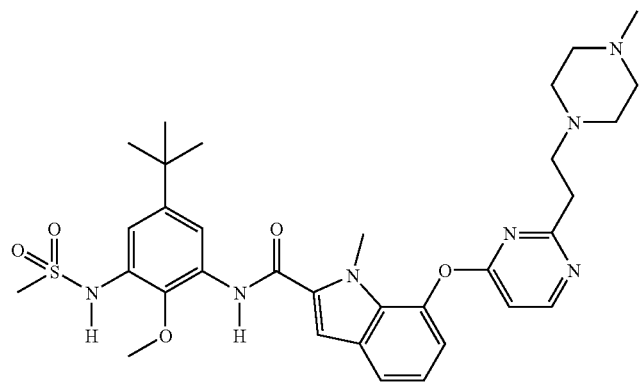

1-Methyl-7-{2-[2-(4-methyl-piperazin-1-yl)-ethyl]-pyrimidin-4-yloxy}-1H-indole-2-carboxylic acid (5-tert-butyl-3-methanesulfonylamino-2-methoxy-phenyl)-amide

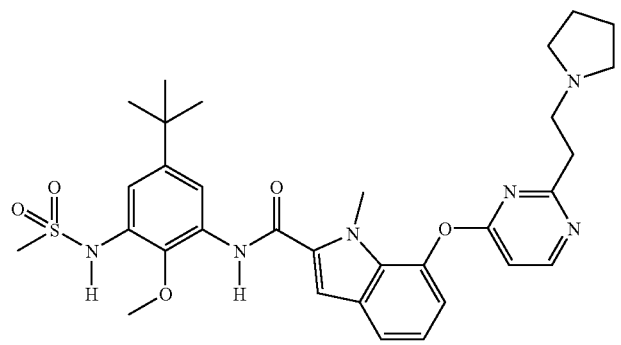

1-Methyl-7-[2-(2-pyrrolidin-1-yl-ethyl)-pyrimidin-4-yloxy]-1H-indole-2-carboxylic acid (5-tert-butyl-3-methanesulfonylamino-2-methoxy-phenyl)-amide

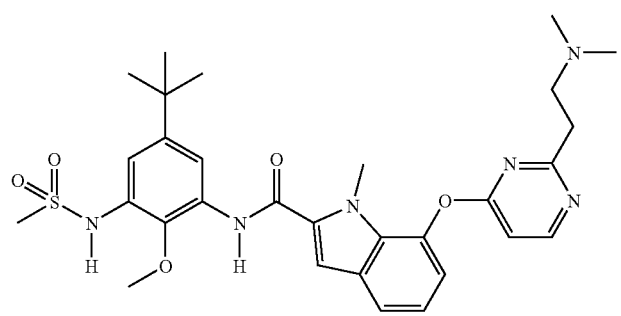

7-[2-(2-Dimethylamino-ethyl)-pyrimidin-4-yloxy]-1-methyl-1H-indole-2-carboxylic acid (5-tert-butyl-3-methanesulfonylamino-2-methoxy-phenyl)-amide

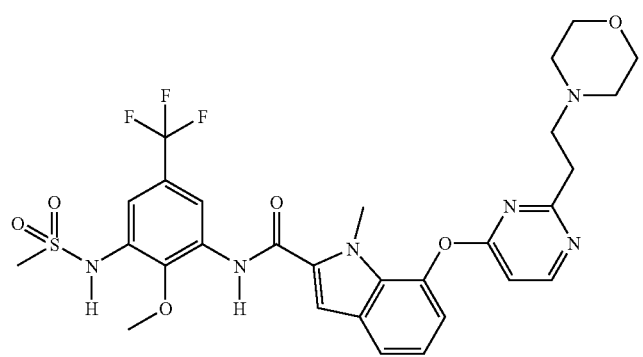

1-Methyl-7-[2-(2-morpholin-4-yl-ethyl)-pyrimidin-4-yloxy]-1H-indole-2-carboxylic acid (3-methanesulfonylamino-2-methoxy-5-trifluoromethyl-phenyl)-amide TABLE I-continued

| Structure | Name |
|---|---|
| (structure) | 1-Methyl-7-[2-(4-methyl-piperazin-1-yl)-pyrimidin-4-yloxy]-1H-indole-2-carboxylic acid (3-methanesulfonylamino-2-methoxy-5-trifluoromethyl-phenyl)-amide |
| (structure) | 7-{2-[2-(4-tert-Butyl-piperazin-1-yl)-ethyl]-pyrimidin-4-yloxy}-1-methyl-1H-indole-2-carboxylic acid (5-tert-butyl-3-methanesulfonylamino-2-methoxy-phenyl)-amide |
| (structure) | 7-[2-(4-tert-Butyl-piperazin-1-ylmethyl)-pyrimidin-4-yloxy]-1-methyl-1H-indole-2-carboxylic acid (5-tert-butyl-3-methanesulfonylamino-2-methoxy-phenyl)-amide |
| (structure) | 1-Methyl-7-(2-pyrrolidin-1-ylmethyl-pyrimidin-4-yloxy)-1H-indole-2-carboxylic acid (5-tert-butyl-3-methanesulfonylamino-2-methoxy-phenyl)-amide |
| (structure) | 7-(2,6-Dimethyl-pyridin-4-yloxy)-1-methyl-1H-indole-2-carboxylic acid (5-tert-butyl-3-methanesulfonylamino-2-methoxy-phenyl)-amide |

TABLE I-continued

| Structure | Name |
|---|---|
| (structure) | 7-(2-Ethyl-pyridin-4-yloxy)-1-methyl-1H-indole-2-carboxylic acid (5-tert-butyl-3-methanesulfonylamino-2-methoxy-phenyl)-amide |
| (structure) | 1-Methyl-7-[2-(1,2,3,6-tetrahydro-pyridin-4-yl)-pyrimidin-4-yloxy]-1H-indole-2-carboxylic acid (5-tert-butyl-3-methanesulfonylamino-2-methoxy-phenyl)-amide |
| (structure) | 7-(2-Amino-pyrimidin-4-yloxy)-1-methyl-1H-indole-2-carboxylic acid (5-tert-butyl-3-methanesulfonylamino-2-methoxy-phenyl)-amide |
| (structure) | 1-Methyl-7-(2-pyrrolidin-1-ylmethyl-pyridin-4-yloxy)-1H-indole-2-carboxylic acid (5-tert-butyl-3-methanesulfonylamino-2-methoxy-phenyl)-amide |
| (structure) | 1-Methyl-7-(2-piperidin-1-ylmethyl-pyridin-4-yloxy)-1H-indole-2-carboxylic acid (5-tert-butyl-3-methanesulfonylamino-2-methoxy-phenyl)-amide |

TABLE I-continued

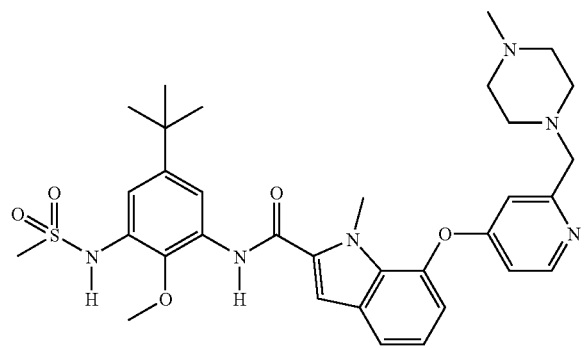

1-Methyl-7-[2-(4-methyl-piperazin-1-ylmethyl)-pyridin-4-yloxy]-1H-indole-2-carboxylic acid (5-tert-butyl-3-methanesulfonylamino-2-methoxy-phenyl)-amide

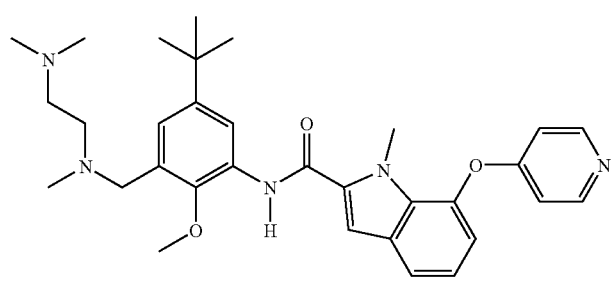

1-Methyl-7-(pyridin-4-yloxy)-1H-indole-2-carboxylic acid (5-tert-butyl-3-{[(2-dimethylamino-ethyl)-methyl-amino]-methyl}-2-methoxy-phenyl)-amide

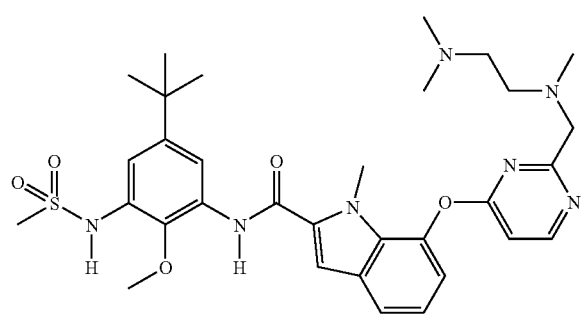

7-(2-{[(2-Dimethylamino-ethyl)-methyl-amino]-methyl}-pyrimidin-4-yloxy)-1-methyl-1H-indole-2-carboxylic acid (5-tert-butyl-3-methanesulfonylamino-2-methoxy-phenyl)-amide

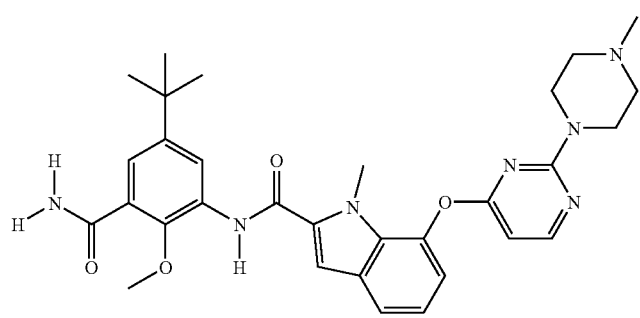

1-Methyl-7-[2-(4-methyl-piperazin-1-yl)-pyrimidin-4-yloxy]-1H-indole-2-carboxylic acid (5-tert-butyl-3-carbamoyl-2-methoxy-phenyl)-amide TABLE I-continued

| | |
|---|---|
| 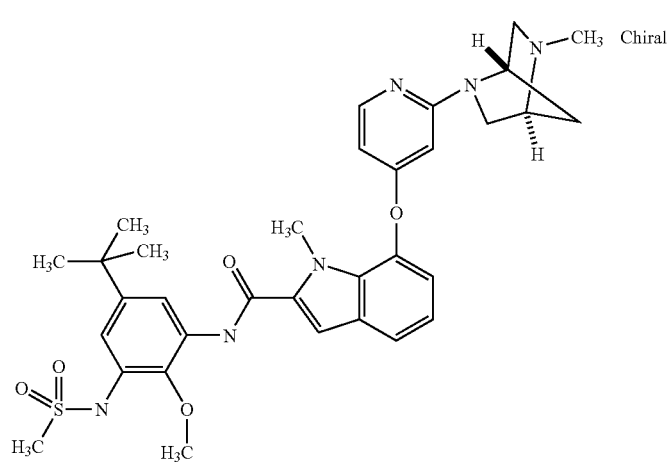 | 1-Methyl-7-[2-((1S,4S)-5-methyl-2,5-diaza-bicyclo[2.2.1]hept-2-yl)-pyridin-4-yloxy]-1H-indole-2-carboxylic acid (5-tert-butyl-3-methanesulfonylamino-2-methoxy-phenyl)-amide |
| 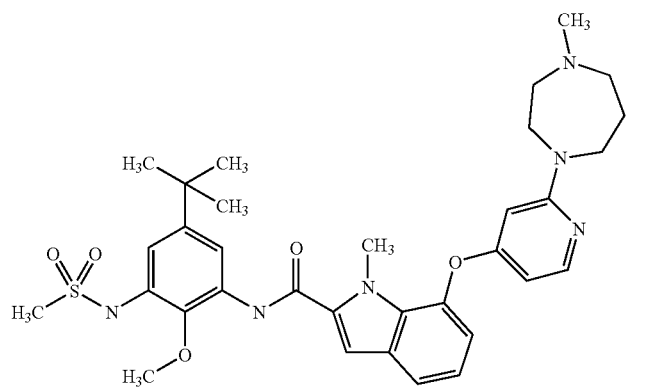 | 1-Methyl-7-[2-(4-methyl-[1,4]diazepan-1-yl)-pyridin-4-yloxy]-1H-indole-2-carboxylic acid (5-tert-butyl-3-methanesulfonylamino-2-methoxy-phenyl)-amide |
| 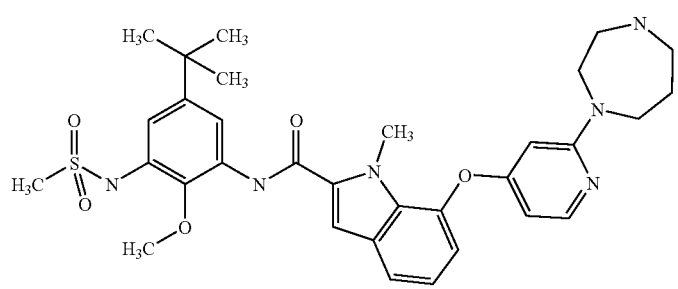 | 7-(2-[1,4]Diazepan-1-yl-pyridin-4-yloxy)-1-methyl-1-H-indole-2-carboxylic acid (5-tert-butyl-3-methanesulfonylamino-2-methoxy-phenyl)-amide |
| 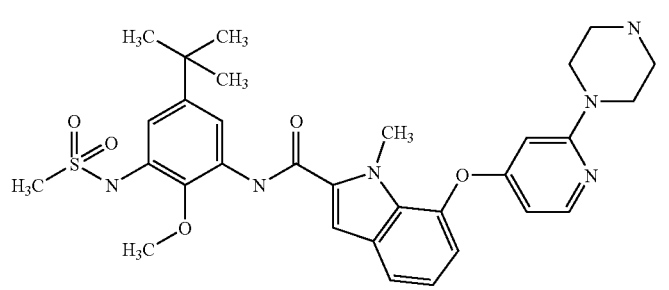 | 1-Methyl-7-(2-piperazin-1-yl-pyridin-4-yloxy)-1H-indole-2-carboxylic acid (5-tert-butyl-3-methanesulfonylamino-2-methoxy-phenyl)-amide |

TABLE I-continued

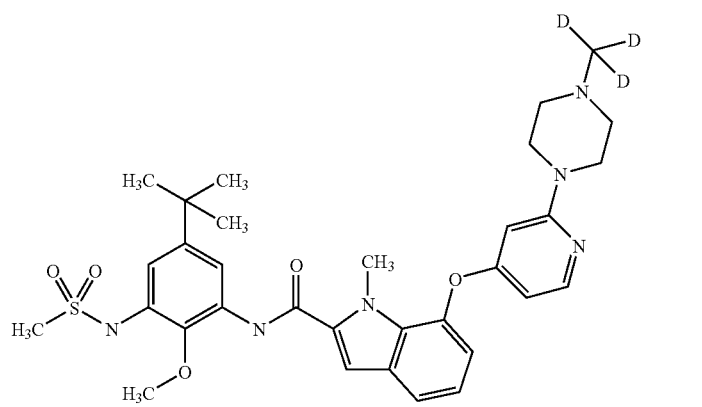

1-trideuterio-7-(2-piperazin-1-yl-pyridin-4-yloxy)-1H-indole-2-carboxylic acid (5-tert-butyl-3-methanesulfonylamino-2-methoxy-phenyl)-amide

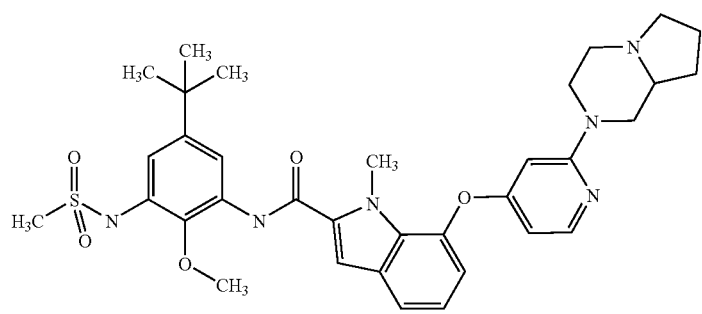

7-[2-(Hexahydro-pyrrolo[1,2-a]pyrazin-2-yl)-pyridin-4-yloxy]-1-methyl-1H-indole-2-carboxylic acid (5-tert-butyl-3-methanesulfonylamino-2-methoxy-phenyl)-amide

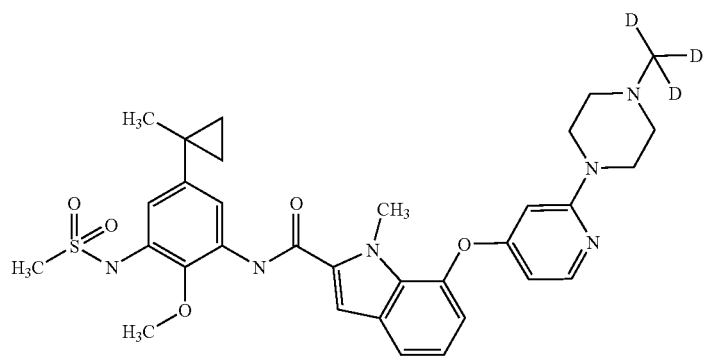

1-trideuterio-7-[2-(4-methyl-piperazin-1-yl)-pyridin-4-yloxy]-1H-indole-2-carboxylic acid [3-methanesulfonylamino-2-methoxy-5-(1-methyl-cyclopropyl)-phenyl]-amide

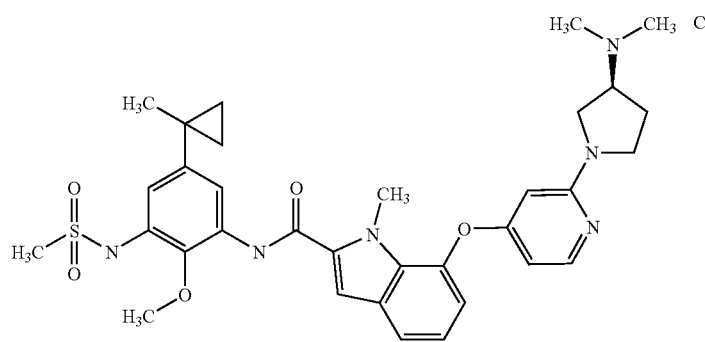

7-[2-((S)-3-Dimethylamino-pyrrolidin-1-yl)-pyridin-4-yloxy]-1-methyl-1H-indole-2-carboxylic acid [3-methanesulfonylamino-2-methoxy-5-(1-methyl-cyclopropyl)-phenyl]-amide TABLE I-continued

| Structure | Name |
|---|---|
| 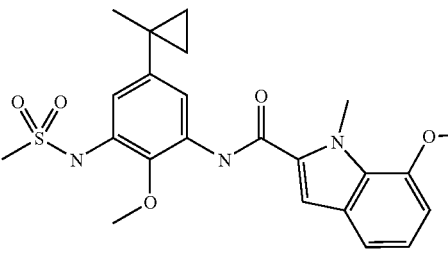 | 7-[2-((S)-3-Dimethylamino-pyrrolidin-1-yl)-pyridin-4-yloxy]-1-methyl-1H-indole-2-carboxylic acid [3-methanesulfonylamino-2-methoxy-5-(1-methyl-cyclopropyl)-phenyl]-amide |
| 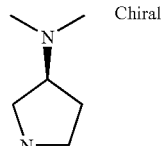 | 1-Methyl-7-[2-(4-methyl-piperazine-1-carbonyl)-pyridin-4-yloxy]-1H-indole-2-carboxylic acid (5-tert-butyl-3-methanesulfonylamino-2-methoxy-phenyl)-amide |
| 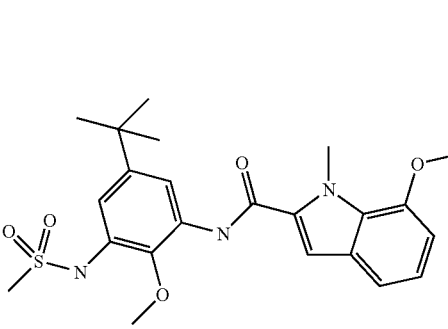 | 1-Methyl-7-[2-(piperazine-1-carbonyl)-pyridin-4-yloxy]-1H-indole-2-carboxylic acid (5-tert-butyl-3-methanesulfonylamino-2-methoxy-phenyl)-amide | or the pharmaceutically acceptable salts, acids, esters or isomers thereof.

Preferred compounds of the invention are listed in table II.

TABLE II

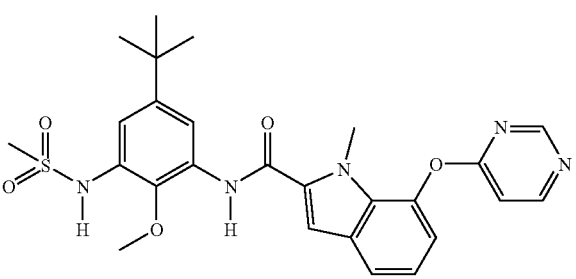

1-Methyl-7-(pyrimidin-4-yloxy)-1H-indole-2-carboxylic acid (5-tert-butyl-3-methanesulfonylamino-2-methoxy-phenyl)-amide

TABLE II-continued

| Structure | Name |
|---|---|
| (structure) | 1-Methyl-7-[2-(4-methyl-piperazin-1-yl)-pyrimidin-4-yloxy]-1H-indole-2-carboxylic acid (5-tert-butyl-3-carbamoyl-2-methoxy-phenyl)-amide |
| (structure) | 1-Methyl-7-(2-pyrrolidin-1-ylmethyl-pyrimidin-4-yloxy)-1H-indole-2-carboxylic acid (5-tert-butyl-3-methanesulfonylamino-2-methoxy-phenyl)-amide |
| (structure) | 7-(2-{[(2-Dimethylamino-ethyl)-methyl-amino]-methyl}-pyrimidin-4-yloxy)-1-methyl-1H-indole-2-carboxylic acid (5-tert-butyl-3-methanesulfonylamino-2-methoxy-phenyl)-amide |
| (structure) | 1-Methyl-7-(pyridin-4-yloxy)-1H-indole-2-carboxylic acid (5-tert-butyl-3-{[(2-dimethylamino-ethyl)-methyl-amino]-methyl}-2-methoxy-phenyl)-amide |
| (structure) | 7-[2-(4-tert-Butyl-piperazin-1-ylmethyl)-pyrimidin-4-yloxy]-1-methyl-1H-indole-2-carboxylic acid (5-tert-butyl-3-methanesulfonylamino-2-methoxy-phenyl)-amide |

TABLE II-continued

| | |
|---|---|
| 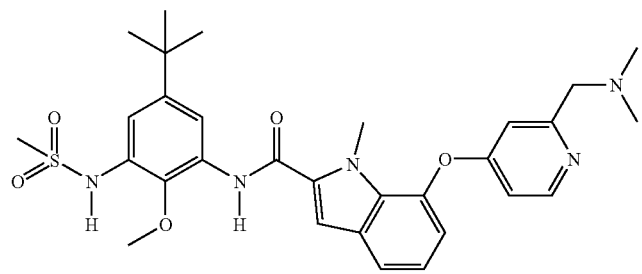 | 7-(2-Dimethylaminomethyl-pyridin-4-yloxy)-1-methyl-1H-indole-2-carboxylic acid (5-tert-butyl-3-methanesulfonylamino-2-methoxy-phenyl)-amide |
| 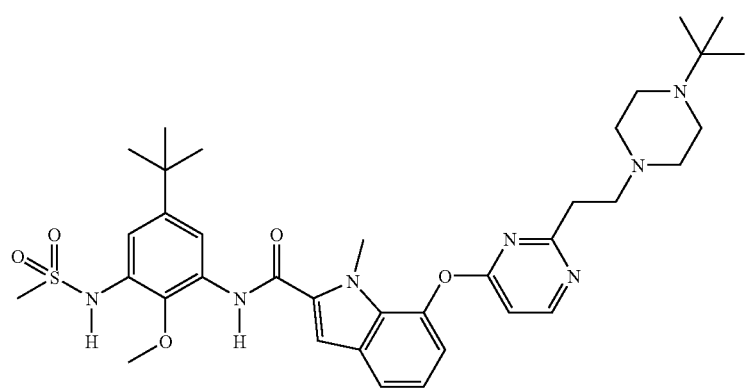 | 7-{2-[2-(4-tert-Butyl-piperazin-1-yl)-ethyl]-pyrimidin-4-yloxy}-1-methyl-1H-indole-2-carboxylic acid (5-tert-butyl-3-methanesulfonylamino-2-methoxy-phenyl)-amide |
| 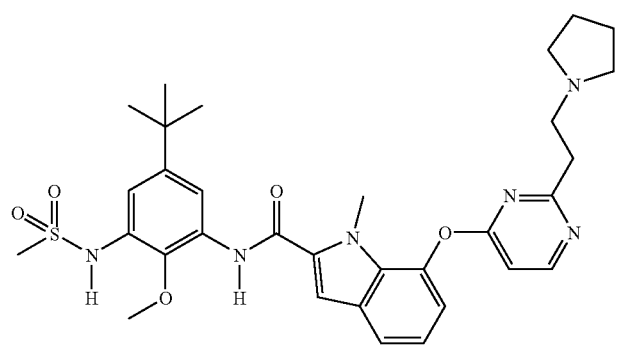 | 1-Methyl-7-[2-(2-pyrrolidin-1-yl-ethyl)-pyrimidin-4-yloxy]-1H-indole-2-carboxylic acid (5-tert-butyl-3-methanesulfonylamino-2-methoxy-phenyl)-amide |
| 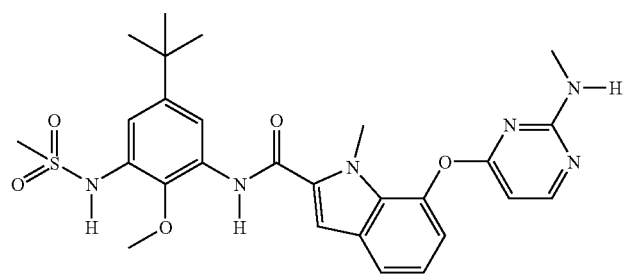 | 1-Methyl-7-(2-methylamino-pyrimidin-4-yloxy)-1H-indole-2-carboxylic acid (5-tert-butyl-3-methanesulfonylamino-2-methoxy-phenyl)-amide |
| 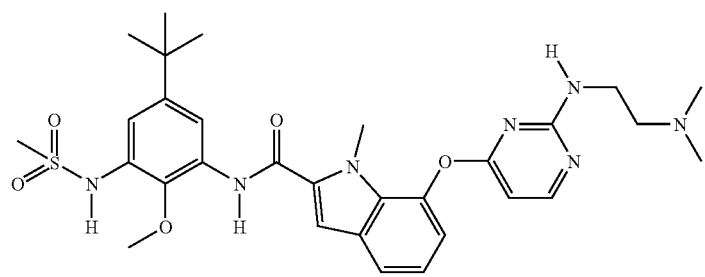 | 7-[2-(2-Dimethylamino-ethylamino)-pyrimidin-4-yloxy]-1-methyl-1H-indole-2-carboxylic acid (5-tert-butyl-3-methanesulfonylamino-2-methoxy-phenyl)-amide |

TABLE II-continued

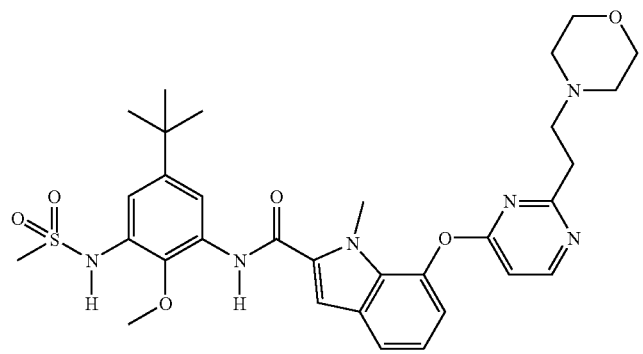

1-Methyl-7-[2-(2-morpholin-4-yl-ethyl)-pyrimidin-4-yloxy]-1H-indole-2-carboxylic acid (5-tert-butyl-3-methanesulfonylamino-2-methoxy-phenyl)-amide

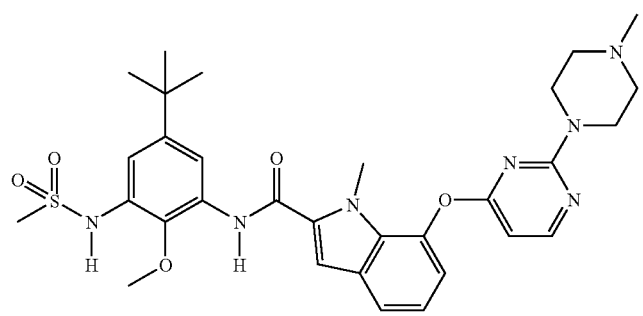

1-Methyl-7-[2-(4-methyl-piperazin-1-yl)-pyrimidin-4-yloxy]-1H-indole-2-carboxylic acid (5-tert-butyl-3-methanesulfonylamino-2-methoxy-phenyl)-amide

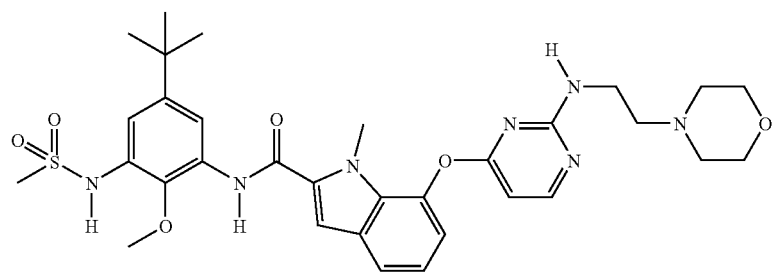

1-Methyl-7-[2-(2-morpholin-4-yl-ethylamino)-pyrimidin-4-yloxy]-1H-indole-2-carboxylic acid (5-tert-butyl-3-methanesulfonylamino-2-methoxy-phenyl)-amide

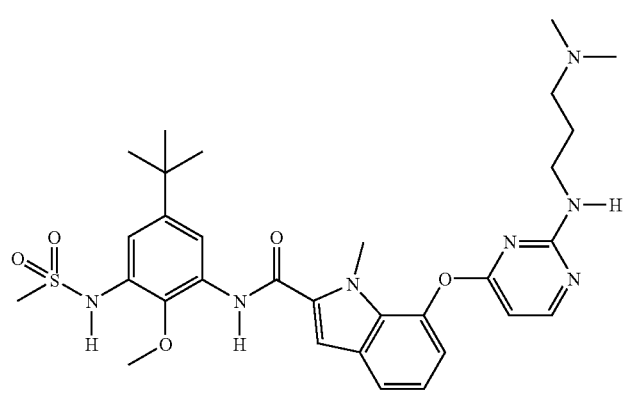

7-[2-(3-Dimethylamino-propylamino)-pyrimidin-4-yloxy]-1-methyl-1H-indole-2-carboxylic acid (5-tert-butyl-3-methanesulfonylamino-2-methoxy-phenyl)-amide TABLE II-continued

| Structure | Name |
|---|---|
| (structure) | 7-[2-(3-Dimethylamino-2,2-dimethyl-propylamino)-pyrimidin-4-yloxy]-1-methyl-1H-indole-2-carboxylic acid (5-tert-butyl-3-methanesulfonylamino-2-methoxy-phenyl)-amide |
| (structure) | 7-(2-Dimethylamino-pyrimidin-4-yloxy)-1-methyl-1H-indole-2-carboxylic acid (5-tert-butyl-3-methanesulfonylamino-2-methoxy-phenyl)-amide |
| (structure) | 1-Methyl-7-(6-methyl-2-methylamino-pyrimidin-4-yloxy)-1H-indole-2-carboxylic acid (5-tert-butyl-3-methanesulfonylamino-2-methoxy-phenyl)-amide |
| (structure) | 1-Methyl-7-[2-(2-pyrrolidin-1-yl-ethylamino)-pyrimidin-4-yloxy]-1H-indole-2-carboxylic acid (5-tert-butyl-3-methanesulfonylamino-2-methoxy-phenyl)-amide |
| (structure) | 1-Methyl-7-[2-(piperidin-4-ylamino)-pyrimidin-4-yloxy]-1H-indole-2-carboxylic acid (5-tert-butyl-3-methanesulfonylamino-2-methoxy-phenyl)-amide |

TABLE II-continued

| Structure | Name |
|---|---|
| 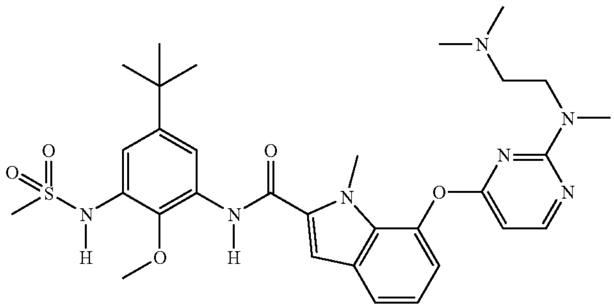 | 7-{2-[(2-Dimethylamino-ethyl)-methyl-amino]-pyrimidin-4-yloxy}-1-methyl-1H-indole-2-carboxylic acid (5-tert-butyl-3-methanesulfonylamino-2-methoxy-phenyl)-amide |
| 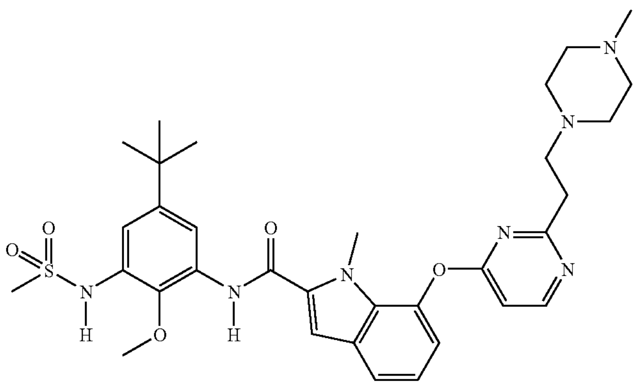 | 1-Methyl-7-{2-[2-(4-methyl-piperazin-1-yl)-ethyl]-pyrimidin-4-yloxy}-1H-indole-2-carboxylic acid (5-tert-butyl-3-methanesulfonylamino-2-methoxy-phenyl)-amide |
| 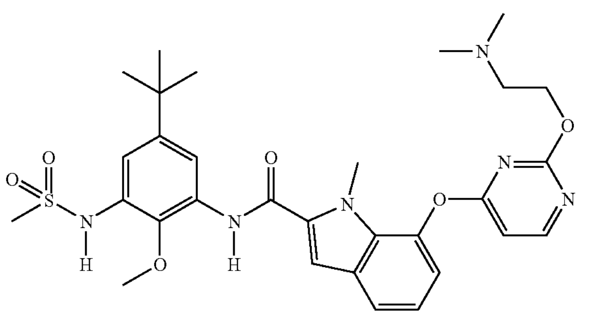 | 7-[2-(2-Dimethylamino-ethoxy)-pyrimidin-4-yloxy]-1-methyl-1H-indole-2-carboxylic acid (5-tert-butyl-3-methanesulfonylamino-2-methoxy-phenyl)-amide |
| 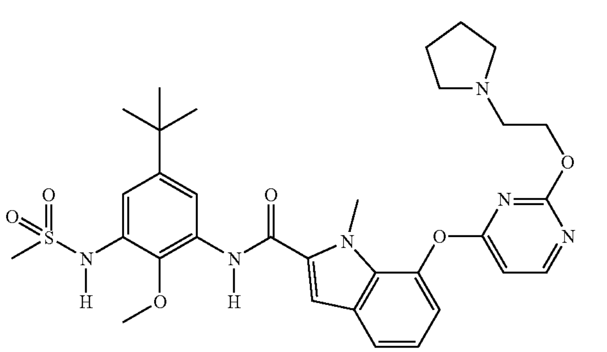 | 1-Methyl-7-[2-(2-pyrrolidin-1-yl-ethoxy)-pyrimidin-4-yloxy]-1H-indole-2-carboxylic acid (5-tert-butyl-3-methanesulfonylamino-2-methoxy-phenyl)-amide |

TABLE II-continued

| | |
|---|---|
| 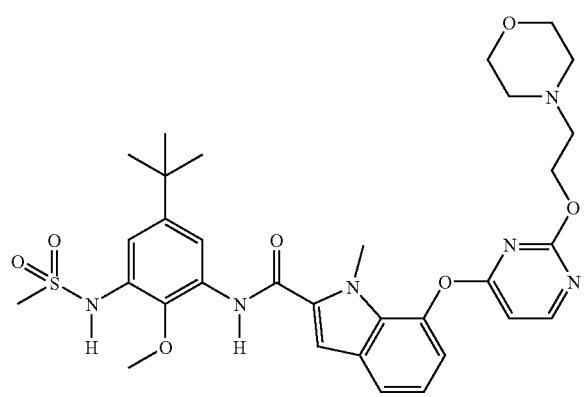 | 1-Methyl-7-[2-(2-morpholin-4-yl-ethoxy)-pyrimidin-4-yloxy]-1H-indole-2-carboxylic acid (5-tert-butyl-3-methanesulfonylamino-2-methoxy-phenyl)-amide |
| 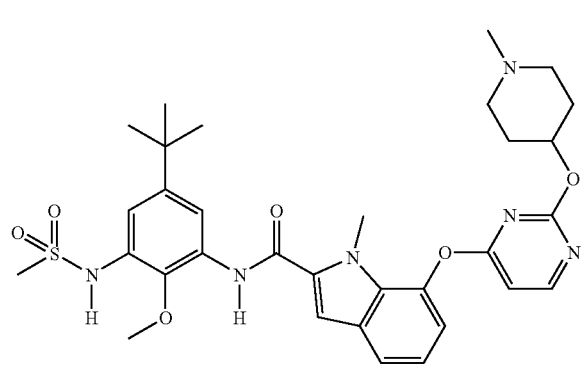 | 1-Methyl-7-[2-(1-methyl-piperidin-4-yloxy)-pyrimidin-4-yloxy]-1H-indole-2-carboxylic acid (5-tert-butyl-3-methanesulfonylamino-2-methoxy-phenyl)-amide |
| 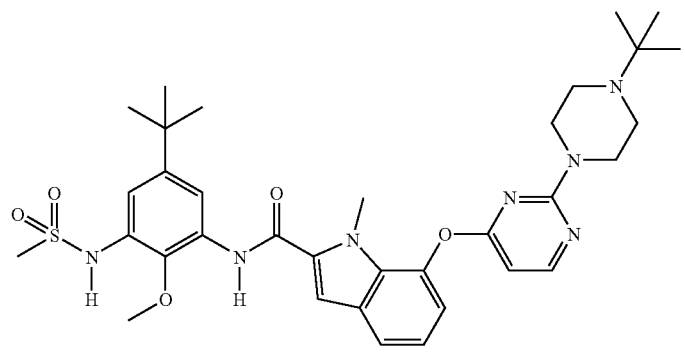 | 7-[2-(4-tert-Butyl-piperazin-1-yl)-pyrimidin-4-yloxy]-1-methyl-1H-indole-2-carboxylic acid (5-tert-butyl-3-methanesulfonylamino-2-methoxy-phenyl)-amide |
| 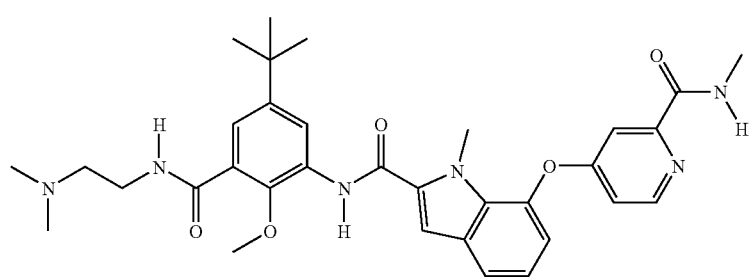 | 1-Methyl-7-(2-methylcarbamoyl-pyridin-4-yloxy)-1H-indole-2-carboxylic acid [5-tert-butyl-3-(2-dimethylamino-ethylcarbamoyl)-2-methoxy-phenyl]-amide |

TABLE II-continued

| Structure | Name |
|---|---|
| (structure) | 7-[2-(2-Dimethylamino-ethylcarbamoyl)-pyridin-4-yloxy]-1-methyl-1H-indole-2-carboxylic acid (5-tert-butyl-3-methanesulfonylamino-2-methoxy-phenyl)-amide |
| (structure) | 1-Methyl-7-(2-methylamino-pyrimidin-4-yloxy)-1H-indole-2-carboxylic acid [5-tert-butyl-3-(2-dimethylamino-ethylcarbamoyl)-2-methoxy-phenyl]-amide |
| (structure) | 1-Methyl-7-(2-methylamino-pyrimidin-4-yloxy)-1H-indole-2-carboxylic acid [5-tert-butyl-2-methoxy-3-(2-morpholin-4-yl-ethylcarbamoyl)-phenyl]-amide |
| (structure) | 1-Methyl-7-(2-methylamino-pyrimidin-4-yloxy)-1H-indole-2-carboxylic acid (5-tert-butyl-3-carbamoyl-2-methoxy-phenyl)-amide |
| (structure) | 1-Methyl-7-(2-methylamino-pyrimidin-4-yloxy)-1H-indole-2-carboxylic acid (5-tert-butyl-2-methoxy-3-methylcarbamoyl-phenyl)-amide |

TABLE II-continued

| Structure | Name |
|---|---|
| (structure) | 1-Methyl-7-(2-pyrrolidin-1-ylmethyl-pyridin-4-yloxy)-1H-indole-2-carboxylic acid (5-tert-butyl-3-methanesulfonylamino-2-methoxy-phenyl)-amide |
| (structure) | 7-[2-(1,2-Dihydroxy-ethyl)-pyrimidin-4-yloxy]-1-methyl-1H-indole-2-carboxylic acid (5-tert-butyl-3-methanesulfonylamino-2-methoxy-phenyl)-amide |
| (structure) | 1-Methyl-7-[2-(morpholin-4-ylamino)-pyrimidin-4-yloxy]-1H-indole-2-carboxylic acid (5-tert-butyl-3-methanesulfonylamino-2-methoxy-phenyl)-amide |
| (structure) | 1-Methyl-7-(2-morpholin-4-ylmethyl-pyrimidin-4-yloxy)-1H-indole-2-carboxylic acid (5-tert-butyl-3-methanesulfonylamino-2-methoxy-phenyl)-amide |
| (structure) | 1-Methyl-7-(2-morpholin-4-ylmethyl-pyridin-4-yloxy)-1H-indole-2-carboxylic acid (5-tert-butyl-3-methanesulfonylamino-2-methoxy-phenyl)-amide |

TABLE II-continued

| | |
|---|---|
| 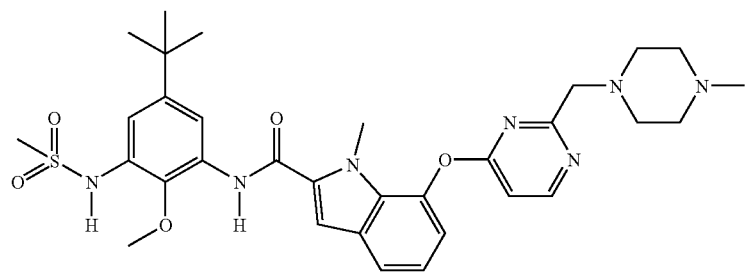 | 1-Methyl-7-[2-(4-methyl-piperazin-1-ylmethyl)-pyrimidin-4-yloxy]-1H-indole-2-carboxylic acid (5-tert-butyl-3-methanesulfonylamino-2-methoxy-phenyl)-amide |
| 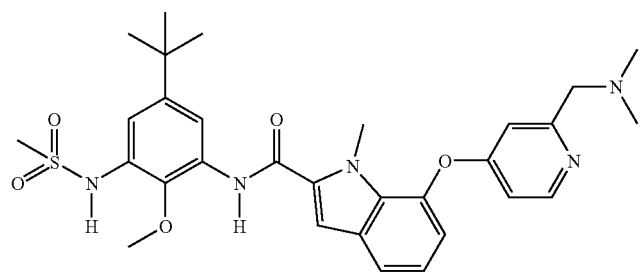 | 7-(2-Dimethylaminomethyl-pyridin-4-yloxy)-1-methyl-1H-indole-2-carboxylic acid (5-tert-butyl-3-methanesulfonylamino-2-methoxy-phenyl)-amide |
| 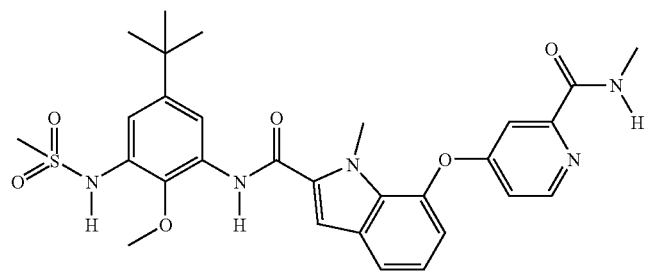 | 1-Methyl-7-(2-methylcarbamoyl-pyridin-4-yloxy)-1H-indole-2-carboxylic acid (5-tert-butyl-3-methanesulfonylamino-2-methoxy-phenyl)-amide |
| 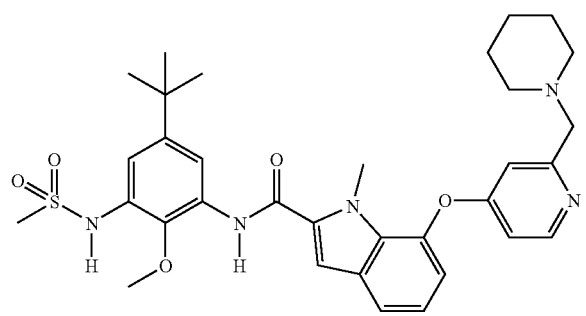 | 1-Methyl-7-(2-piperidin-1-ylmethyl-pyridin-4-yloxy)-1H-indole-2-carboxylic acid (5-tert-butyl-3-methanesulfonylamino-2-methoxy-phenyl)-amide |
| 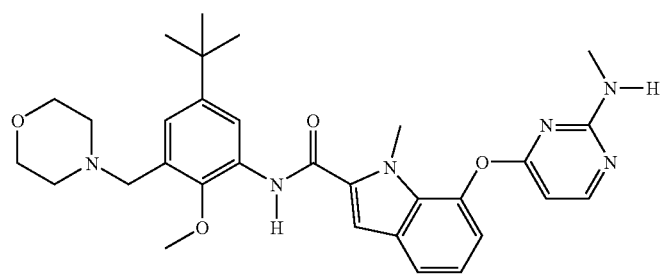 | 1-Methyl-7-(2-methylamino-pyrimidin-4-yloxy)-1H-indole-2-carboxylic acid (5-tert-butyl-2-methoxy-3-morpholin-4-ylmethyl-phenyl)-amide |

TABLE II-continued

| | |
|---|---|
| 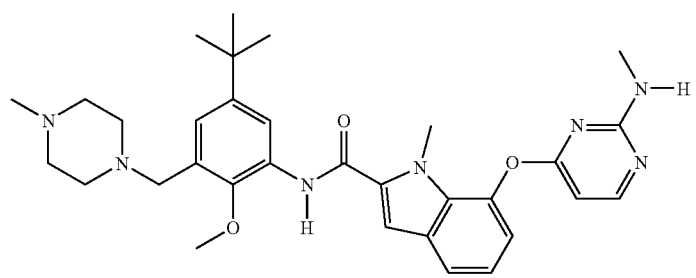 | 1-Methyl-7-(2-methylamino-pyrimidin-4-yloxy)-1H-indole-2-carboxylic acid [5-tert-butyl-2-methoxy-3-(4-methyl-piperazin-1-ylmethyl)-phenyl]-amide |
| 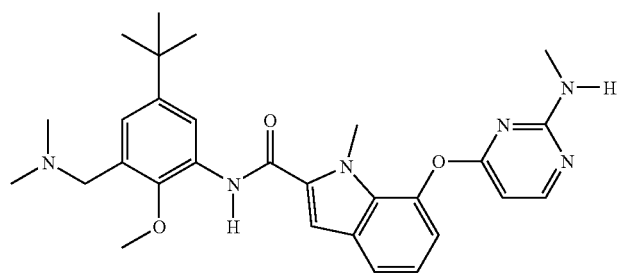 | 1-Methyl-7-(2-methylamino-pyrimidin-4-yloxy)-1H-indole-2-carboxylic acid (5-tert-butyl-3-dimethylaminomethyl-2-methoxy-phenyl)-amide |
| 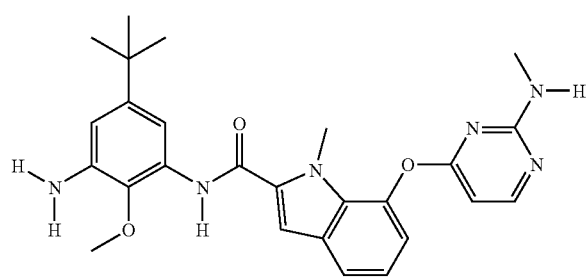 | 1-Methyl-7-(2-methylamino-pyrimidin-4-yloxy)-1H-indole-2-carboxylic acid (3-amino-5-tert-butyl-2-methoxy-phenyl)-amide |
| 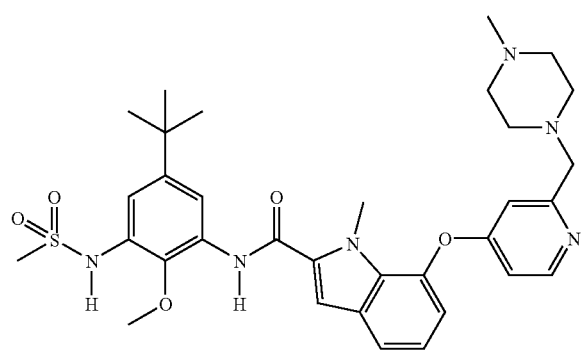 | 1-Methyl-7-[2-(4-methyl-piperazin-1-ylmethyl)-pyridin-4-yloxy]-1H-indole-2-carboxylic acid (5-tert-butyl-3-methanesulfonylamino-2-methoxy-phenyl)-amide |
| 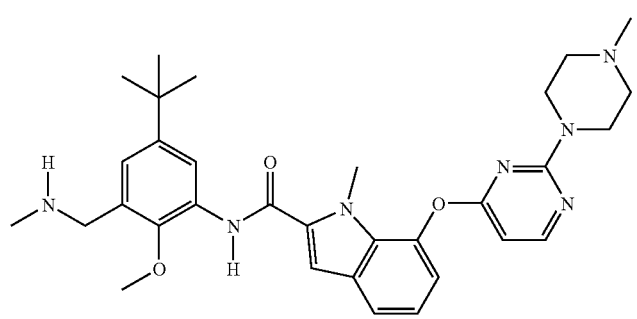 | 1-Methyl-7-[2-(4-methyl-piperazin-1-yl)-pyrimidin-4-yloxy]-1H-indole-2-carboxylic acid (5-tert-butyl-2-methoxy-3-methylaminomethyl-phenyl)-amide |

TABLE II-continued

| Structure | Name |
|---|---|
| (structure) | 1-Methyl-7-[2-(4-methyl-piperazin-1-yl)-pyrimidin-4-yloxy]-1H-indole-2-carboxylic acid (5-tert-butyl-2-methoxy-3-pyrrolidin-1-ylmethyl-phenyl)-amide |
| (structure) | 1-Methyl-7-{2-[methyl-(1-methyl-piperidin-4-yl)-amino]-pyrimidin-4-yloxy}-1H-indole-2-carboxylic acid (5-tert-butyl-3-methanesulfonylamino-2-methoxy-phenyl)-amide |
| (structure) | 7-(2-Hydroxymethyl-pyridin-4-yloxy)-1-methyl-1H-indole-2-carboxylic acid (5-tert-butyl-3-methanesulfonylamino-2-methoxy-phenyl)-amide |
| (structure) | 1-Methyl-7-(2-methylamino-pyrimidin-4-yloxy)-1H-indole-2-carboxylic acid [5-tert-butyl-2-methoxy-3-(2-morpholin-4-yl-ethylamino)-phenyl]-amide and |
| (structure) | 1-Methyl-7-(pyridin-4-yloxy)-1H-indole-2-carboxylic acid (5-tert-butyl-3-methanesulfonylamino-2-methoxy-phenyl)-amide | or the pharmaceutically acceptable salts, acids, esters or isomers thereof.

The following are representative compounds of the invention which can be made according to the general schemes and working examples below:

TABLE III

| Structure | Name |
|---|---|
| 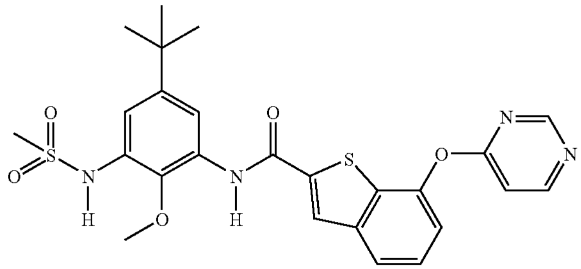 | 7-(Pyrimidin-4-yloxy)-benzo[b]thiophene-2-carboxylic acid (5-tert-butyl-3-methanesulfonylamino-2-methoxy-phenyl)-amide |
| 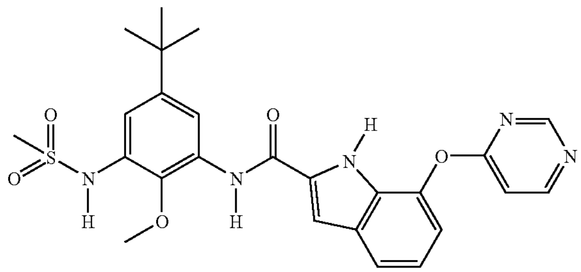 | 7-(Pyrimidin-4-yloxy)-1H-indole-2-carboxylic acid (5-tert-butyl-3-methanesulfonylamino-2-methoxy-phenyl)-amide |
| 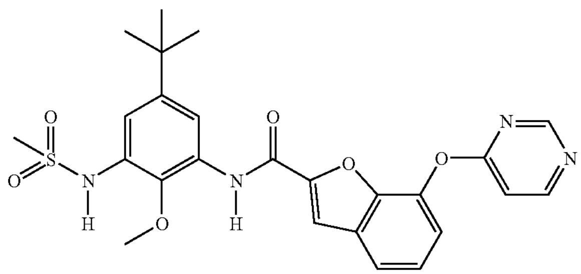 | 7-(Pyrimidin-4-yloxy)-benzofuran-2-carboxylic acid (5-tert-butyl-3-methanesulfonylamino-2-methoxy-phenyl)-amide |
| 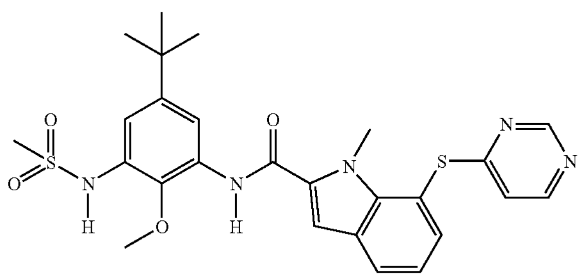 | 1-Methyl-7-(pyrimidin-4-ylsulfanyl)-1H-indole-2-carboxylic acid (5-tert-butyl-3-methanesulfonylamino-2-methoxy-phenyl)-amide |
| 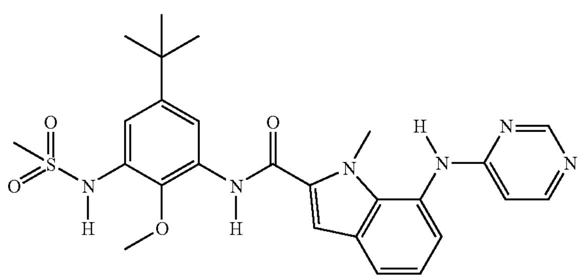 | 1-Methyl-7-(pyrimidin-4-ylamino)-1H-indole-2-carboxylic acid (5-tert-butyl-3-methanesulfonylamino-2-methoxy-phenyl)-amide |

TABLE III-continued

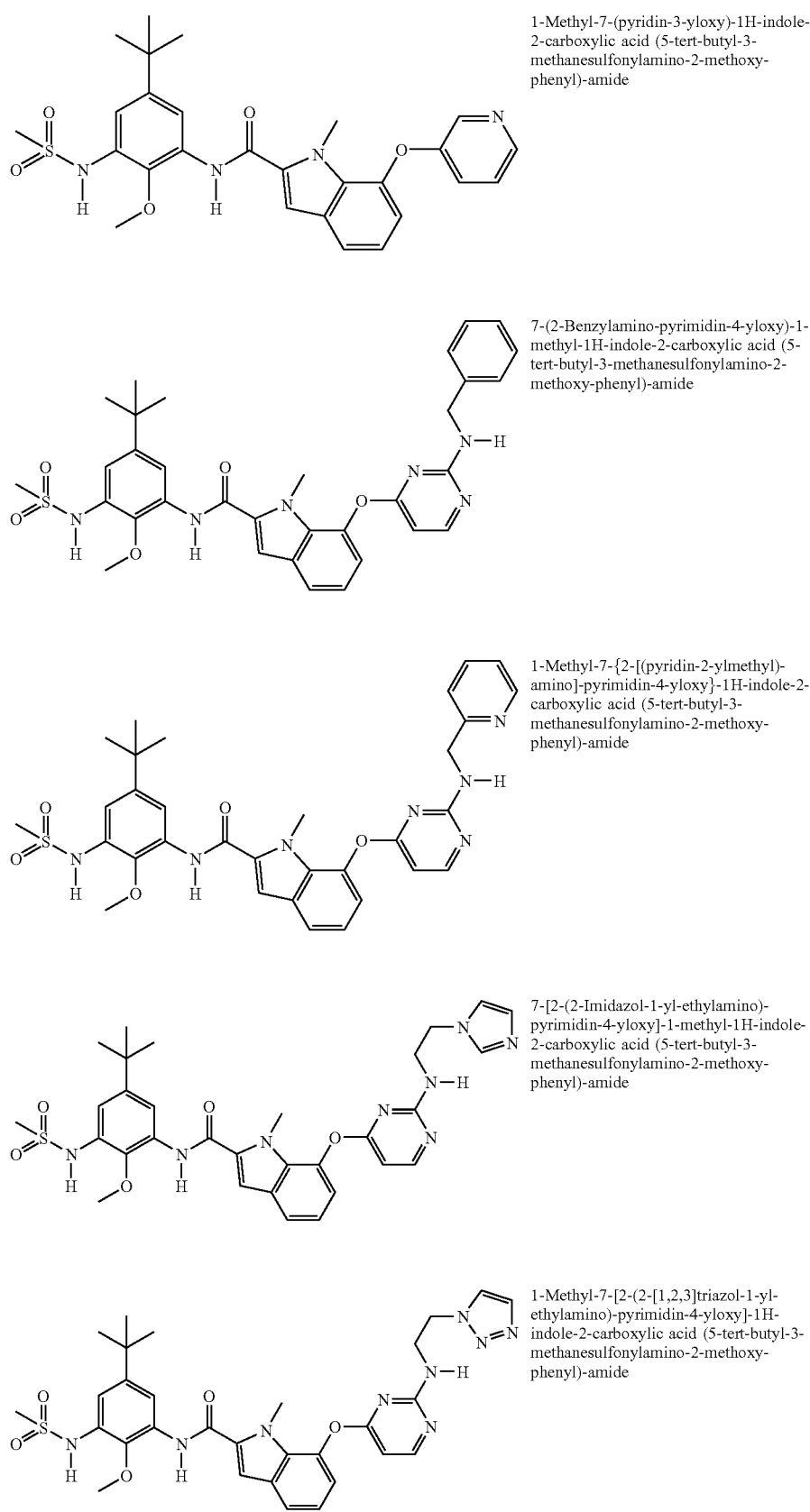

1-Methyl-7-(pyridin-3-yloxy)-1H-indole-2-carboxylic acid (5-tert-butyl-3-methanesulfonylamino-2-methoxy-phenyl)-amide 7-(2-Benzylamino-pyrimidin-4-yloxy)-1-methyl-1H-indole-2-carboxylic acid (5-tert-butyl-3-methanesulfonylamino-2-methoxy-phenyl)-amide 1-Methyl-7-{2-[(pyridin-2-ylmethyl)-amino]-pyrimidin-4-yloxy}-1H-indole-2-carboxylic acid (5-tert-butyl-3-methanesulfonylamino-2-methoxy-phenyl)-amide 7-[2-(2-Imidazol-1-yl-ethylamino)-pyrimidin-4-yloxy]-1-methyl-1H-indole-2-carboxylic acid (5-tert-butyl-3-methanesulfonylamino-2-methoxy-phenyl)-amide 1-Methyl-7-[2-(2-[1,2,3]triazol-1-yl-ethylamino)-pyrimidin-4-yloxy]-1H-indole-2-carboxylic acid (5-tert-butyl-3-methanesulfonylamino-2-methoxy-phenyl)-amide TABLE III-continued

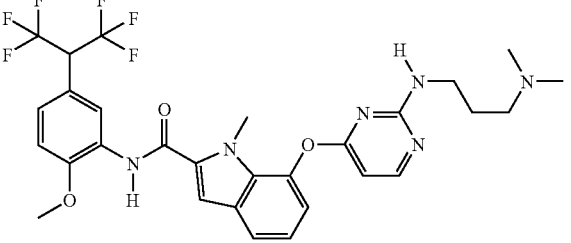

7-[2-(3-Dimethylamino-propylamino)-pyrimidin-4-yloxy]-1-methyl-1H-indole-2-carboxylic acid [2-methoxy-5-(2,2,2-trifluoro-1-trifluoromethyl-ethyl)-phenyl]-amide

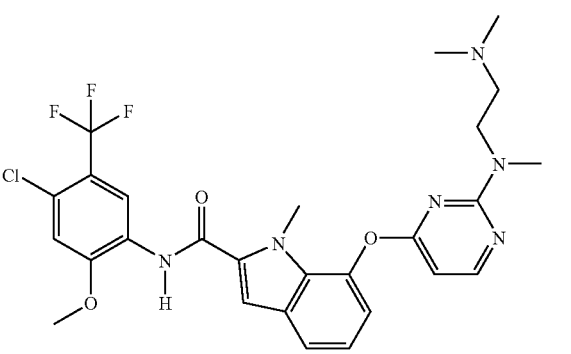

7-{2-[(2-Dimethylamino-ethyl)-methyl-amino]-pyrimidin-4-yloxy}-1-methyl-1H-indole-2-carboxylic acid (4-chloro-2-methoxy-5-trifluoromethyl-phenyl)-amide

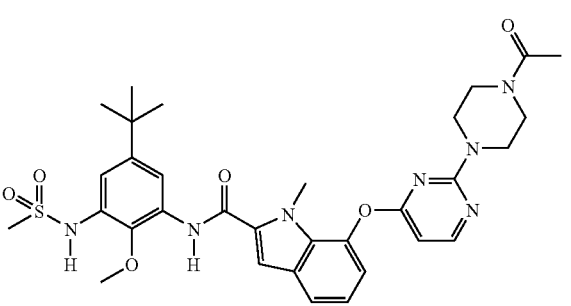

7-[2-(4-Acetyl-piperazin-1-yl)-pyrimidin-4-yloxy]-1-methyl-1H-indole-2-carboxylic acid (5-tert-butyl-3-methanesulfonylamino-2-methoxy-phenyl)-amide

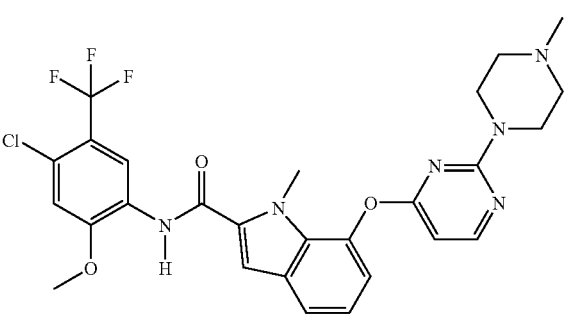

1-Methyl-7-[2-(4-methyl-piperazin-1-yl)-pyrimidin-4-yloxy]-1H-indole-2-carboxylic acid (4-chloro-2-methoxy-5-trifluoromethyl-phenyl)-amide

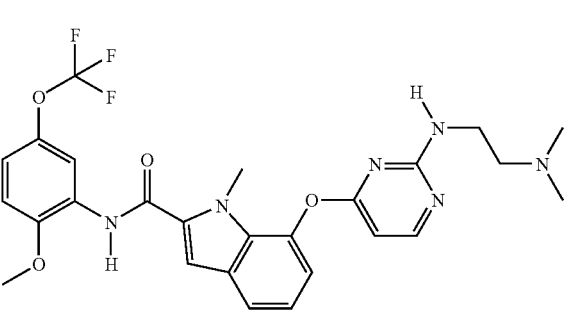

7-[2-(2-Dimethylamino-ethylamino)-pyrimidin-4-yloxy]-1-methyl-1H-indole-2-carboxylic acid (2-methoxy-5-trifluoromethoxy-phenyl)-amide TABLE III-continued

| Structure | Name |
|---|---|
| 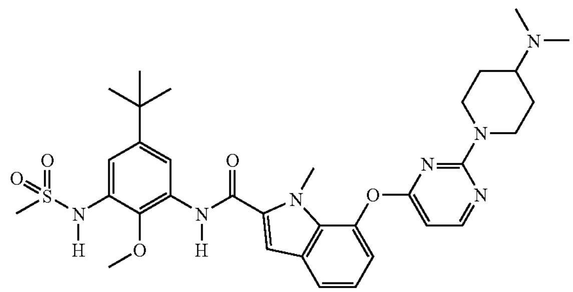 | 7-[2-(4-Dimethylamino-piperidin-1-yl)-pyrimidin-4-yloxy]-1-methyl-1H-indole-2-carboxylic acid (5-tert-butyl-3-methanesulfonylamino-2-methoxy-phenyl)-amide |
| 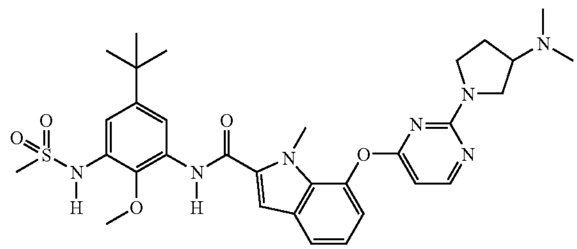 | 7-[2-(3-Dimethylamino-pyrrolidin-1-yl)-pyrimidin-4-yloxy]-1-methyl-1H-indole-2-carboxylic acid (5-tert-butyl-3-methanesulfonylamino-2-methoxy-phenyl)-amide |
| 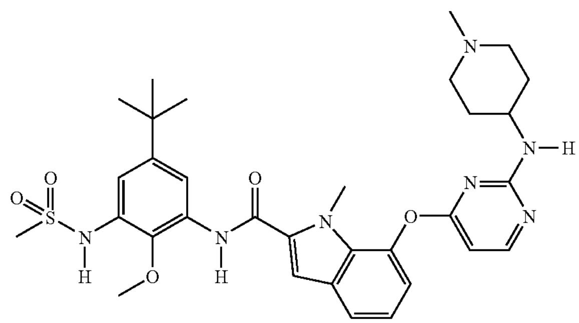 | 1-Methyl-7-[2-(1-methyl-piperidin-4-ylamino)-pyrimidin-4-yloxy]-1H-indole-2-carboxylic acid (5-tert-butyl-3-methanesulfonylamino-2-methoxy-phenyl)-amide |
| 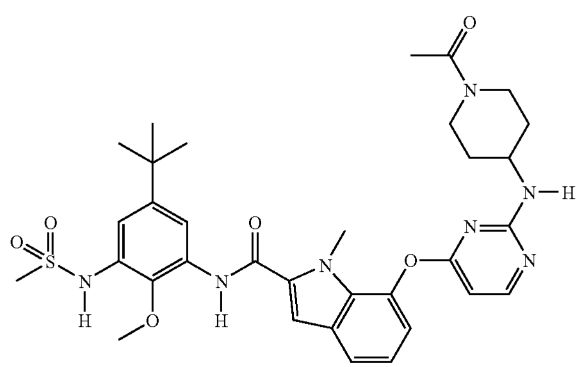 | 7-[2-(1-Acetyl-piperidin-4-ylamino)-pyrimidin-4-yloxy]-1-methyl-1H-indole-2-carboxylic acid (5-tert-butyl-3-methanesulfonylamino-2-methoxy-phenyl)-amide |
| 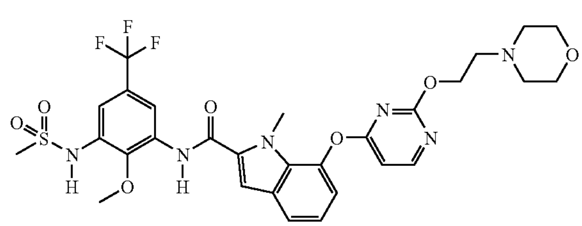 | 1-Methyl-7-[2-(2-morpholin-4-yl-ethoxy)-pyrimidin-4-yloxy]-1H-indole-2-carboxylic acid (3-methanesulfonylamino-2-methoxy-5-trifluoromethyl-phenyl)-amide |

TABLE III-continued

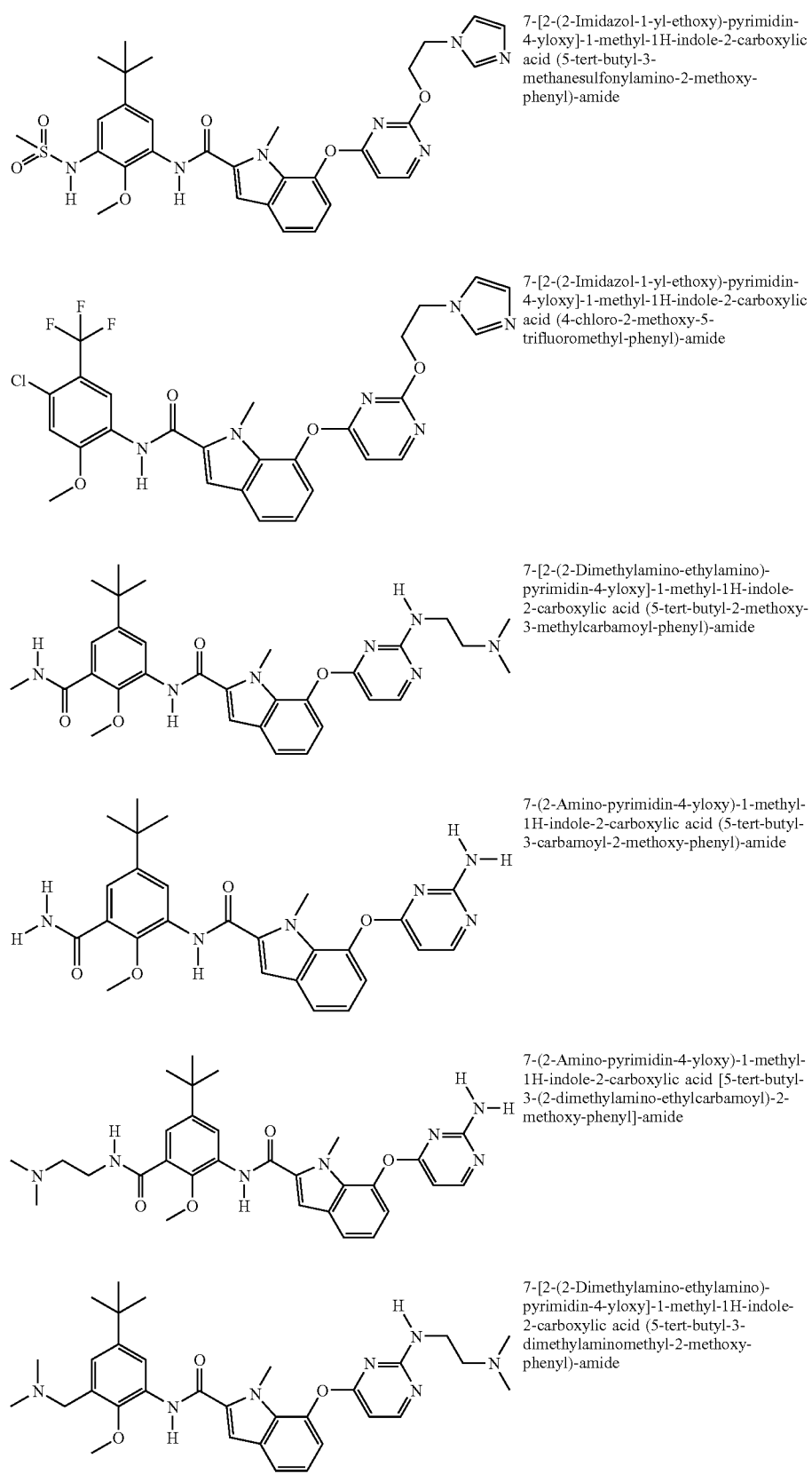

7-[2-(2-Imidazol-1-yl-ethoxy)-pyrimidin-4-yloxy]-1-methyl-1H-indole-2-carboxylic acid (5-tert-butyl-3-methanesulfonylamino-2-methoxy-phenyl)-amide 7-[2-(2-Imidazol-1-yl-ethoxy)-pyrimidin-4-yloxy]-1-methyl-1H-indole-2-carboxylic acid (4-chloro-2-methoxy-5-trifluoromethyl-phenyl)-amide 7-[2-(2-Dimethylamino-ethylamino)-pyrimidin-4-yloxy]-1-methyl-1H-indole-2-carboxylic acid (5-tert-butyl-2-methoxy-3-methylcarbamoyl-phenyl)-amide 7-(2-Amino-pyrimidin-4-yloxy)-1-methyl-1H-indole-2-carboxylic acid (5-tert-butyl-3-carbamoyl-2-methoxy-phenyl)-amide 7-(2-Amino-pyrimidin-4-yloxy)-1-methyl-1H-indole-2-carboxylic acid [5-tert-butyl-3-(2-dimethylamino-ethylcarbamoyl)-2-methoxy-phenyl]-amide 7-[2-(2-Dimethylamino-ethylamino)-pyrimidin-4-yloxy]-1-methyl-1H-indole-2-carboxylic acid (5-tert-butyl-3-dimethylaminomethyl-2-methoxy-phenyl)-amide TABLE III-continued

| Structure | Name |
|---|---|
| 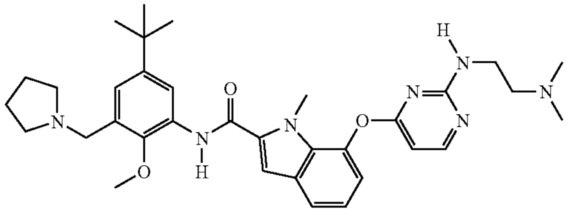 | 7-[2-(2-Dimethylamino-ethylamino)-pyrimidin-4-yloxy]-1-methyl-1H-indole-2-carboxylic acid (5-tert-butyl-2-methoxy-3-pyrrolidin-1-ylmethyl-phenyl)-amide |
| 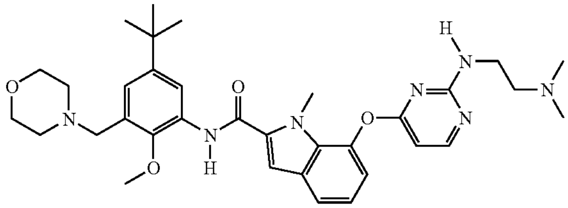 | 7-[2-(2-Dimethylamino-ethylamino)-pyrimidin-4-yloxy]-1-methyl-1H-indole-2-carboxylic acid (5-tert-butyl-2-methoxy-3-morpholin-4-ylmethyl-phenyl)-amide |
| 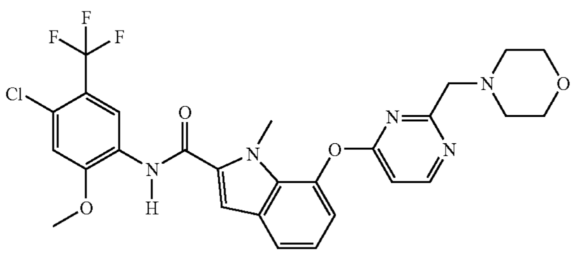 | 1-Methyl-7-(2-morpholin-4-ylmethyl-pyrimidin-4-yloxy)-1H-indole-2-carboxylic acid (4-chloro-2-methoxy-5-trifluoromethyl-phenyl)-amide |
| 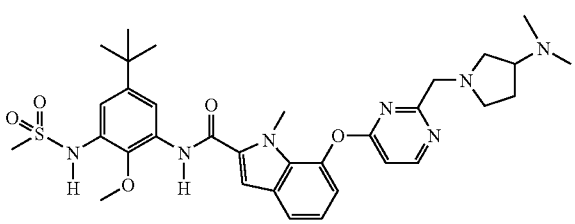 | 7-[2-(3-Dimethylamino-pyrrolidin-1-ylmethyl)-pyrimidin-4-yloxy]-1-methyl-1H-indole-2-carboxylic acid (5-tert-butyl-3-methanesulfonylamino-2-methoxy-phenyl)-amide |
| 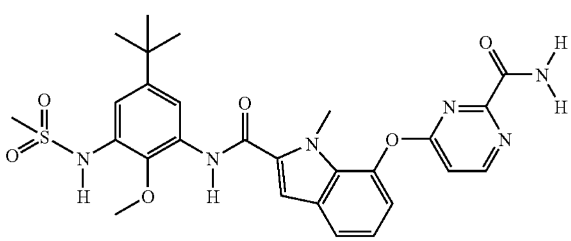 | 7-(2-Carbamoyl-pyrimidin-4-yloxy)-1-methyl-1H-indole-2-carboxylic acid (5-tert-butyl-3-methanesulfonylamino-2-methoxy-phenyl)-amide |
| 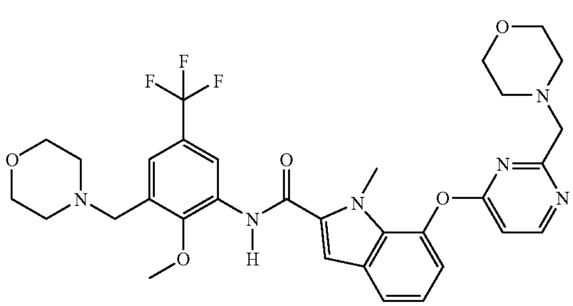 | 1-Methyl-7-(2-morpholin-4-ylmethyl-pyrimidin-4-yloxy)-1H-indole-2-carboxylic acid (2-methoxy-3-morpholin-4-ylmethyl-5-trifluoromethyl-phenyl)-amide |

TABLE III-continued

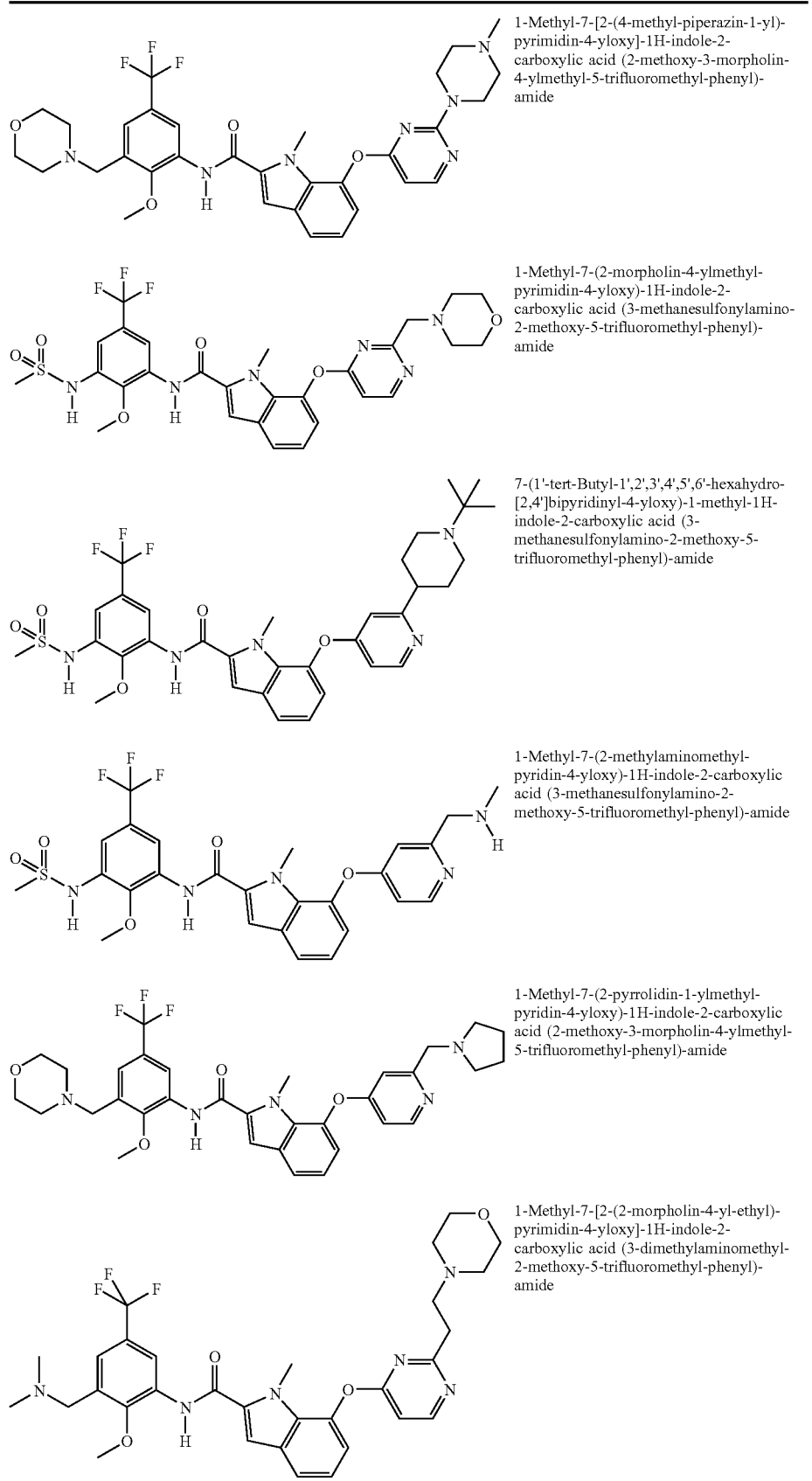

1-Methyl-7-[2-(4-methyl-piperazin-1-yl)-pyrimidin-4-yloxy]-1H-indole-2-carboxylic acid (2-methoxy-3-morpholin-4-ylmethyl-5-trifluoromethyl-phenyl)-amide 1-Methyl-7-(2-morpholin-4-ylmethyl-pyrimidin-4-yloxy)-1H-indole-2-carboxylic acid (3-methanesulfonylamino-2-methoxy-5-trifluoromethyl-phenyl)-amide 7-(1'-tert-Butyl-1',2',3',4',5',6'-hexahydro-[2,4']bipyridinyl-4-yloxy)-1-methyl-1H-indole-2-carboxylic acid (3-methanesulfonylamino-2-methoxy-5-trifluoromethyl-phenyl)-amide 1-Methyl-7-(2-methylaminomethyl-pyridin-4-yloxy)-1H-indole-2-carboxylic acid (3-methanesulfonylamino-2-methoxy-5-trifluoromethyl-phenyl)-amide 1-Methyl-7-(2-pyrrolidin-1-ylmethyl-pyridin-4-yloxy)-1H-indole-2-carboxylic acid (2-methoxy-3-morpholin-4-ylmethyl-5-trifluoromethyl-phenyl)-amide 1-Methyl-7-[2-(2-morpholin-4-yl-ethyl)-pyrimidin-4-yloxy]-1H-indole-2-carboxylic acid (3-dimethylaminomethyl-2-methoxy-5-trifluoromethyl-phenyl)-amide TABLE III-continued

| Structure | Name |
|---|---|
| 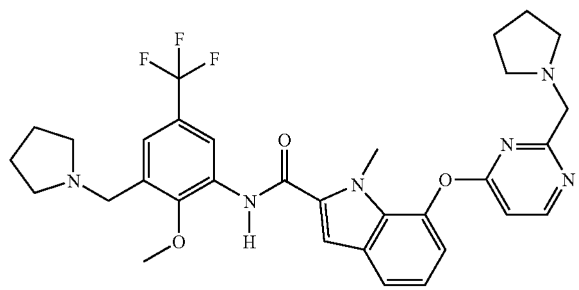 | 1-Methyl-7-(2-pyrrolidin-1-ylmethyl-pyrimidin-4-yloxy)-1H-indole-2-carboxylic acid (2-methoxy-3-pyrrolidin-1-ylmethyl-5-trifluoromethyl-phenyl)-amide |
| 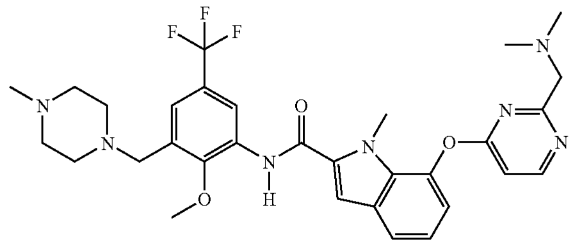 | 7-(2-Dimethylaminomethyl-pyrimidin-4-yloxy)-1-methyl-1H-indole-2-carboxylic acid [2-methoxy-3-(4-methyl-piperazin-1-ylmethyl)-5-trifluoromethyl-phenyl]-amide |
| 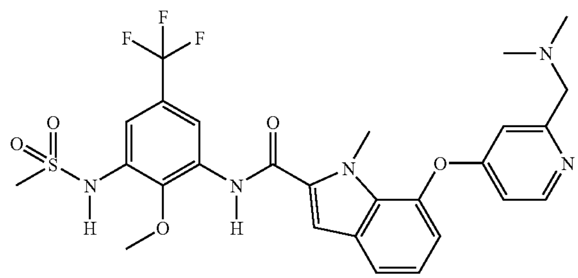 | 7-(2-Dimethylaminomethyl-pyridin-4-yloxy)-1-methyl-1H-indole-2-carboxylic acid (3-methanesulfonylamino-2-methoxy-5-trifluoromethyl-phenyl)-amide |
| | 7-(2-Dimethylaminomethyl-pyrimidin-4-yloxy)-1-methyl-1H-indole-2-carboxylic acid (3-methanesulfonylamino-2-methoxy-5-trifluoromethyl-phenyl)-amide |
| 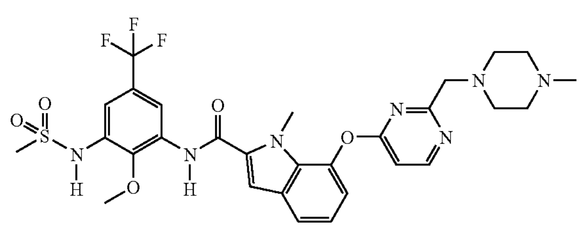 | 1-Methyl-7-[2-(4-methyl-piperazin-1-ylmethyl)-pyrimidin-4-yloxy]-1H-indole-2-carboxylic acid (3-methanesulfonylamino-2-methoxy-5-trifluoromethyl-phenyl)-amide |
| | 7-(2-Dimethylaminomethyl-pyrimidin-4-yloxy)-1-methyl-1H-indole-2-carboxylic acid (3-methanesulfonylamino-2-methoxy-5-trifluoromethyl-phenyl)-amide |

TABLE III-continued

| Structure | Name |
|---|---|
| 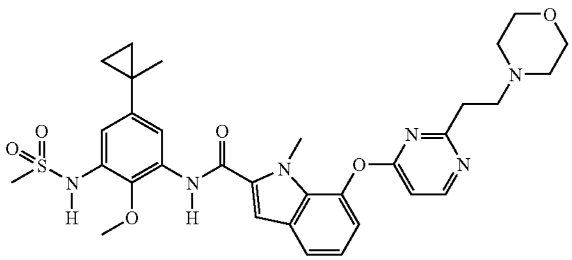 | 1-Methyl-7-[2-(2-morpholin-4-yl-ethyl)-pyrimidin-4-yloxy]-1H-indole-2-carboxylic acid [3-methanesulfonylamino-2-methoxy-5-(1-methyl-cyclopropyl)-phenyl]-amide |
| 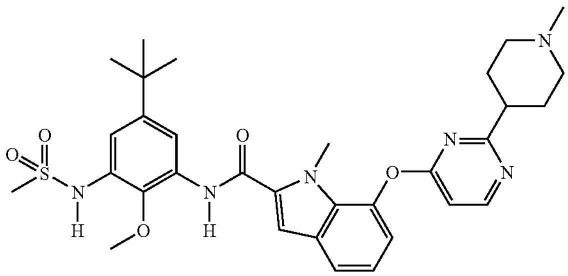 | 1-Methyl-7-[2-(1-methyl-piperidin-4-yl)-pyrimidin-4-yloxy]-1H-indole-2-carboxylic acid (5-tert-butyl-3-methanesulfonylamino-2-methoxy-phenyl)-amide |
| 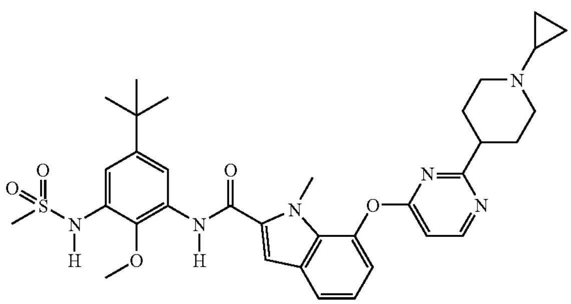 | 7-[2-(1-Cyclopropyl-piperidin-4-yl)-pyrimidin-4-yloxy]-1-methyl-1H-indole-2-carboxylic acid (5-tert-butyl-3-methanesulfonylamino-2-methoxy-phenyl)-amide |
| 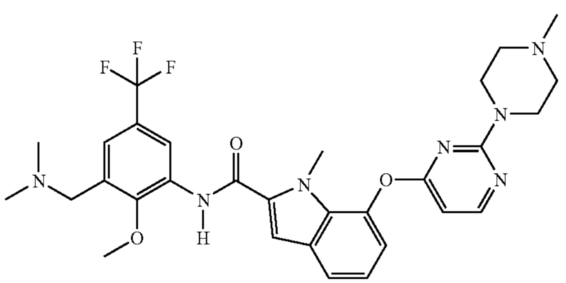 | 1-Methyl-7-[2-(4-methyl-piperazin-1-yl)-pyrimidin-4-yloxy]-1H-indole-2-carboxylic acid (3-dimethylaminomethyl-2-methoxy-5-trifluoromethyl-phenyl)-amide |
| | 1-Methyl-7-[2-(1-methyl-pyrrolidin-3-ylamino)-pyridin-4-yloxy]-1H-indole-2-carboxylic acid (5-tert-butyl-3-methanesulfonylamino-2-methoxy-phenyl)-amide | or the pharmaceutically acceptable salts, acids, esters or isomers thereof.

In all the compounds disclosed hereinabove in this application, in the event the nomenclature is in conflict with the structure, it shall be understood that the compound is defined by the structure.

Of particular importance according to the invention are compounds of formula (I), wherein $Ar^1$, X, Y, Q, W, $R^3$, $R^4$, $R^5$, $R^6$ and $R^y$ have the meaning indicated, for use as pharmaceutical compositions with an anti-cytokine activity.

The invention also relates to the use of a compound of formula (I), wherein $Ar_1$, X, Y, Q, W, $R^3$, $R^4$, $R^5$, $R^6$ and $R^y$ have the meaning indicated, for preparing a pharmaceutical composition for the treatment and/or prevention of a cytokine mediated disease or condition.

The invention also relates to pharmaceutical preparations, containing as active substance one or more compounds of formula (I), wherein $Ar_1$, X, Y, Q, W, $R^3$, $R^4$, $R^5$, $R^6$ and $R^y$ have the meanings indicated, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and $N-(C_1-C_4 \text{ alkyl})_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

GENERAL SYNTHETIC METHODS

The invention additionally provides for methods of making the compounds of the formula (I). The compounds of the invention may be prepared by the general methods and examples presented below, and methods known to those of ordinary skill in the art.

Further reference in this regard may be made to U.S. Pat. No. 6,358,945,U.S. application Ser. Nos. 09/714,539, 09/834,797, 10/120,028, 10/143,322 and 10/147,675. U.S. application Ser. No. 10/264,689 teaches additional methods for preparation of sulfonamide intermediates. Each of the aforementioned US cases are incorporated in their entirety. In all schemes, unless otherwise specified, $Ar^1$, X, Y, W and $R^3$-$R^6$ in the formulas shown below shall have the meanings defined for these groups in the definition of the formula (I) of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

Compounds of the invention where Q is a carbon atom, may be prepared as described in Schemes I and II. Compounds of the invention wherein Q is a nitrogen atom, may be prepared by analogous methods which will be apparent to one of ordinary skill in the art.

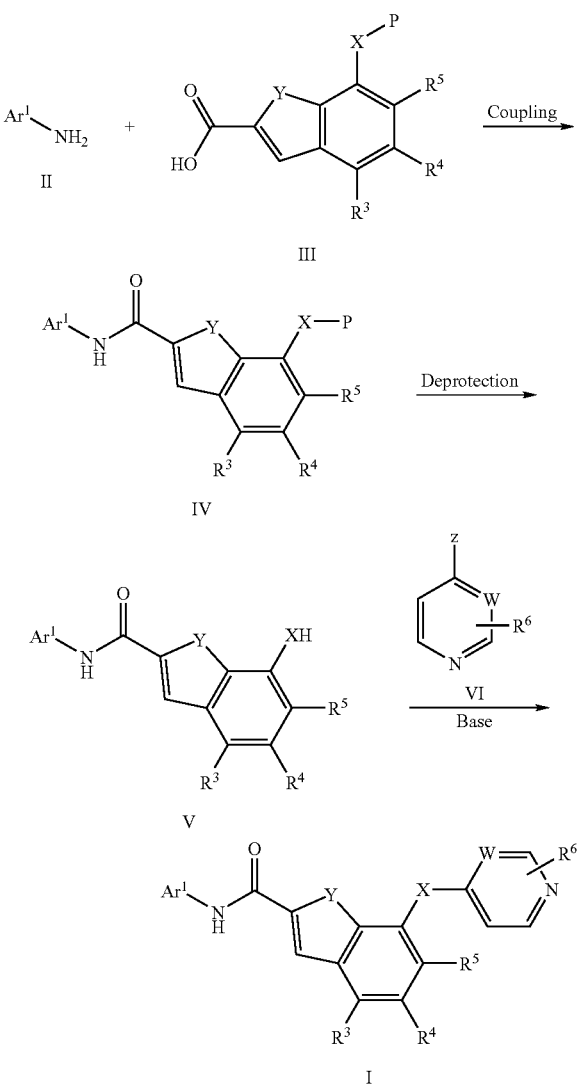

As illustrated in Scheme I an amine bearing $Ar^1$ is coupled with carboxylic acid III, where P is a protecting group, using standard coupling conditions known in the art (see for example M. Bodanszky, 1984,The Practice of Peptide Synthesis, Springer-Verlag). For example, one may couple III and II by treating with 1-[3-(dimethylamino)propyl]-3-ethylcarbodiimide hydrochloride (EDC) followed by 1-hydroxybenzotriazole hydrate (HOBT) in a suitable solvent such as DMF. Removal of the protecting group P to provide V may be achieved by standard procedures known in the art. For example, if P is a benzyl group, it may be removed by treatment of IV with hydrogen gas in the presence of a catalyst such as palladium on carbon in a suitable solvent such as EtOH. The resulting intermediate V may then be coupled with the desired halo heterocycle VI (Z=halogen) bearing $R^6$ in the presence of a suitable base to provide I. $Ar^1$ and $R^6$ may be further modified by standard synthetic methods known in the art to produce additional compounds of formula (I). Several examples are described in the Synthetic Examples section below.

In a modification of the above method, the order of coupling VI and Ar¹NH₂ with the central heterocycle may be reversed. This is illustrated in Scheme II.

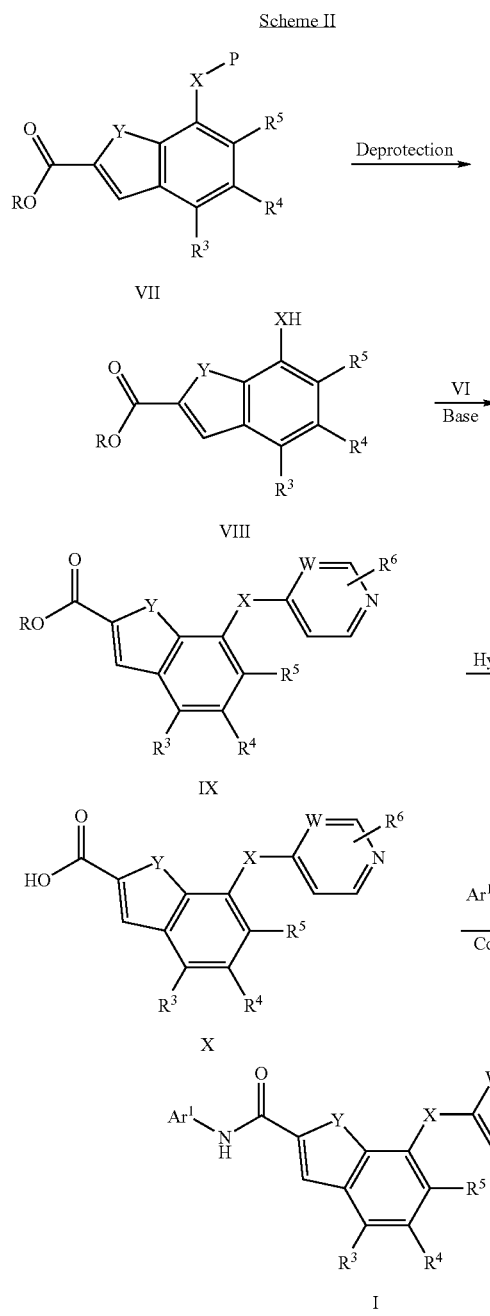

As illustrated above, the ester VII (R=lower alkyl such as methyl or ethyl, P=a protecting group) is deprotected as described above and the resulting intermediate VIII is coupled, as described above to provide ester IX. This is hydrolyzed using standard hydrolysis conditions and the resulting acid coupled with Ar¹NH₂ to provide I. As above, Ar¹ and R⁶ may be further modified by standard synthetic methods known in the art to produce additional compounds of formula (I). Several examples are described in the Synthetic Examples section below.

SYNTHETIC EXAMPLES

Example 1

Synthesis of 1-methyl-7-[2-(4-methyl-piperazin-1-yl)-pyrimidin-4-yloxy]-1H-indole-2-carboxylic acid (5-tert-butyl-3-methanesulfonylamino-2-methoxy-phenyl)-amide

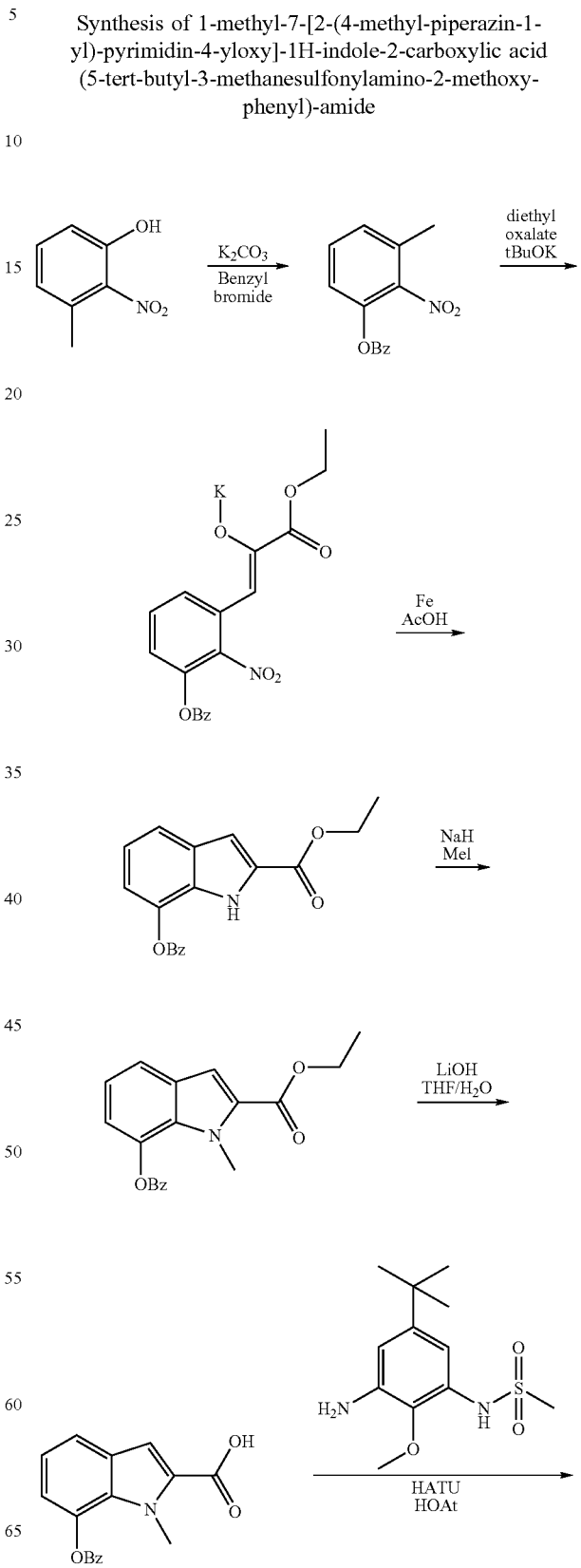

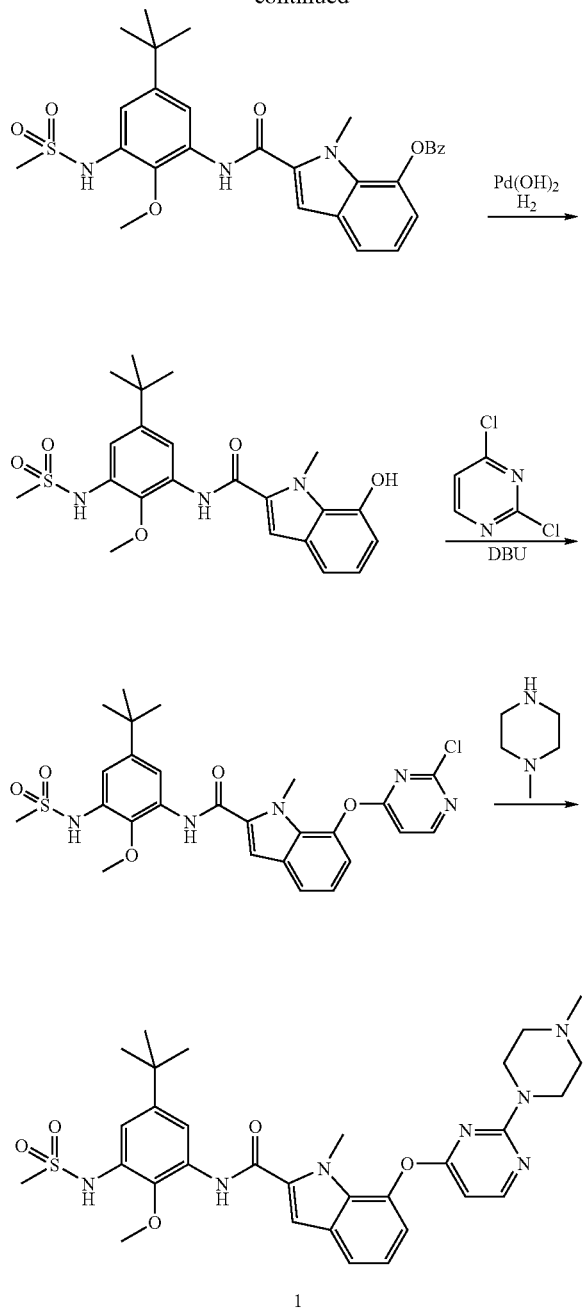

For a similar procedure to form the indole core, see R. Albrecht et al. *Eur. J. Med. Chem. Chim. Ther.* 1985, 20, 59-60.

In a 1 L 3-neck round-bottom flask equipped with a condenser and mechanical stirrer were placed the 2-nitro-3-methylphenol (50.8 g, 331.5 mmol), 500 mL anhydrous acetonitrile and potassium carbonate (57.3 g, 414.3 mmol). The yellow solution became orange. While stirring, benzyl bromide (39.4 mL, 331.5 mmol) was added slowly via syringe, then the mixture was heated to gentle reflux overnight and allowed to cool. An orange precipitates formed. The reaction was quenched with water and extracted with EtOAc three times. The combined organic extracts were washed with brine, dried ($Na_2SO_4$), filtered and concentrated in vacuo. The desired benzyl ether was obtained as a yellow oil, 80.7 g (quantitative).

Potassium tert-Butoxide solution (1.0 M in THF, 100 mL, 100 mmol) was placed in a 1000 mL round-bottom flask under inert atmosphere. Ether (370 mL) was then added causing the solution to become murky. This was followed by addition of diethyl oxalate (14.0 mL, 103.1 mmol). The solution became yellow. After stirring 10 min, the benzyl ether from above (24.3 g, 99.9 mmol) was added directly to the flask and the mixture was left standing overnight. The reaction was heated to a gentle reflux for 18 h then left at room temperature overnight. An orange precipitate had formed. The precipitated product was filtered through a Buchner funnel and washed ether providing 29.1 g of the desired condensation product as the potassium salt.

In a 1 L 3-neck round-bottom flask equipped with a condenser and mechanical stirrer were placed the potassium salt from above (29.1 g, 76.3 mmol) and 250 mL glacial acetic acid. Iron powder (25.6 g, 458.0 mmol) was added and the reaction was stirred at 100° C. for 1 h and then allowed to cool. EtOAc (800 mL) was added and the mixture was filtered through diatomaceous earth and left standing overnight. A saturated aqueous solution of $NaHCO_3$ was added slowly to the filtrate. A lot of bubbling was observed. The layers were separated and the organic phase was washed with water and brine, dried ($MgSO_4$), filtered and concentrated in vacuo. The resulting product was dried under high vacuum overnight. It was then decolorized with charcoal by heating in an EtOH/MeOH mixture, filtered and concentrated in vacuo, providing 7.5 g of the desired indole ester.

The indole ester (19.0 g, 64.3 mmol) was dissolved in 160 mL anhydrous DMF at room temperature and treated with sodium hydride (4.0 g, 100 mmol), added portionwise. Once the mixture cooled back to room temperature, iodomethane (6.2 mL, 100 mmol) was added. Vigorous heating was again observed. One extra equivalent of iodomethane was added. The mixture was left stirring overnight and was then partitioned between EtOAc and saturated aqueous ammonium chloride solution. The organic phase was washed with water twice, then brine, dried ($MgSO_4$), filtered and concentrated in vacuo leaving a brown oil. The product was purified by column chromatography on $SiO_2$ using 10, 20% EtOAc in hexanes as eluent. The 1-methyl indole ester (17.2 g, mixture of methyl and ethyl esters) was isolated as a pale yellow solid.

The above ester (4.01 g, 13.0 mmol) was placed in 100 mL THF and treated with LiOH hydrate (1.1 g, 26.0 mmol) dissolved in 15 mL water. The resulting slightly murky solution was left stirring vigorously at room temperature for 3 days. It was then acidified with dilute aqueous HCl to pH~1 and extracted with EtOAc twice. The extracts were washed with brine twice and dried ($MgSO_4$), filtered and concentrated in vacuo. The resulting carboxylic acid (3.75 g, quantitative) was obtained as a white solid.

The carboxylic acid (0.93 g, 3.31 mmol) in 10 mL anhydrous DMF at room temperature under $N_2$ was treated with O-(7-azabenzotriazol-1-yl)-N,N,N',N'-tetramethyluronium hexafluorophosphate (HATU) (1.71 g, 4.50 mmol), triethylamine (1.75 mL, 12.57 mmol) and catalytic 1-hydroxy-7-azabenzotriazole (HOAt) (231 mg, 1.70 mmol).

After 10 min at room temperature the aniline hydrochloride salt was added in one portion. The mixture was left to stir at room temperature overnight, then diluted with EtOAc, washed with water, dilute aqueous HCl, water again and finally brine. The solution was then dried ($MgSO_4$), filtered and concentrated in vacuo leaving a brown foam. The product was purified by $SiO_2$ column chromatography using EtOAc in hexane eluent mixtures providing the desired amide (1.05 g) as a white solid.

The above amide (1.00 g, 1.87 mmol) was dispersed in 25 mL absolute EtOH. A slurry of 20% $Pd(OH)_2$ in EtOH was added by pipet (230 mg). The mixture was stirred under an atmosphere of $H_2$. After 3 h the reaction was filtered through diatomaceous earth and concentrated in vacuo, providing the debenzylated hydroxy indole amide (843 mg) as a light yellow solid.

The hydroxy indole amide (824 mg, 1.85 mmol) was dissolved in 10 mL anhydrous acetonitrile. DBU (0.277 mL, 1.85 mmol) was added, followed by 2,4-dichloropyrimidine (276 mg, 1.85 mmol) and the reaction was left stirring at room temperature for 1.5 h, then concentrated in vacuo. The residue was loaded on a $SiO_2$ column and purified, eluting with EtOAc in hexanes mixtures. The 2-chloropyrimidinyl ether (367 mg) was isolated as a white solid.

The 2-chloropyrimidinyl ether (104 mg, 0.186 mmol) was placed in 1.5 mL anhydrous THF followed by 1-methylpiperazine (0.042 mL, 0.375 mmol). The mixture was stirred in a sealed tube overnight at 75° C. It was then allowed to cool, then water was added and the mixture was extracted with $CH_2Cl_2$ twice. The combined organic extracts were dried ($MgSO_4$), filtered and concentrated in vacuo, leaving an orange foam. This was dissolved in acetonitrile and heated until product precipitated as an off-white solid that was collected by filtration through vacuum Buchner funnel and air dried. The title compound (80 mg) was obtained as an off-white solid.

Example 2

Synthesis of 1-methyl-7-[2-(2-morpholin-4-yl-ethylamino)-pyrimidin-4-yloxy]-1H-indole-2-carboxylic acid (5-tert-butyl-3-methanesulfonylamino-2-methoxy-phenyl)-amide

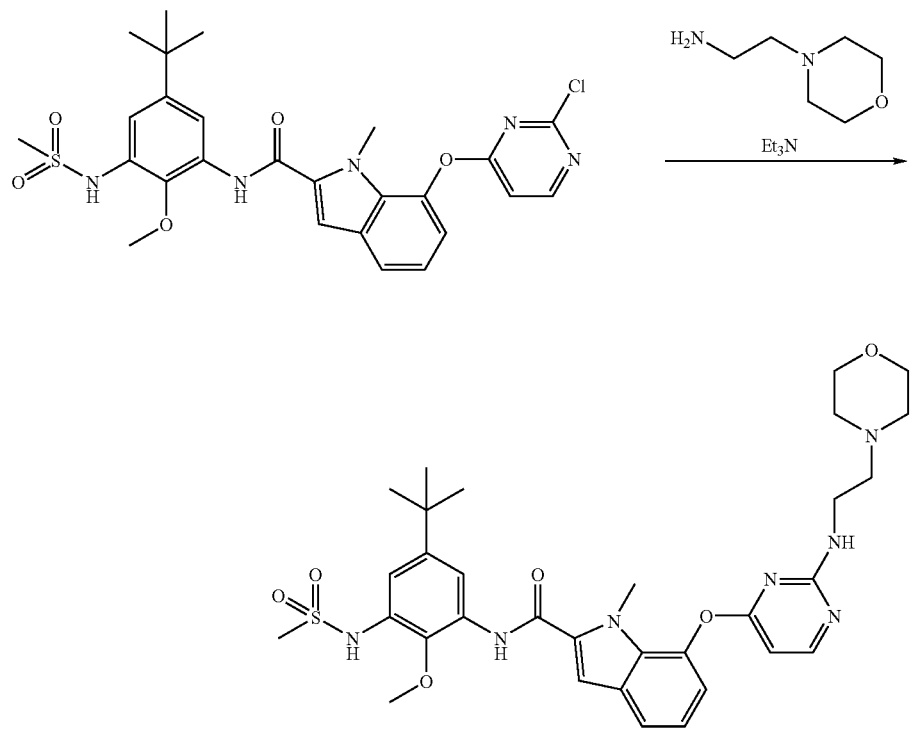

2

The 2-chloropyrimidinyl ether intermediate (75 mg, 0.13 mmol) (see Example 1) was dissolved in 1.0 mL anhydrous THF, treated with triethylamine (21 uL, 0.15 mmol) and 4-aminoethylmorpholine (18 uL, 0.13 mmol). The solution was placed in a sealed tube and stirred in a 75° C. bath overnight. The reaction was then allowed to cool, partitioned between water and EtOAc, and the aqueous phase was extracted with more EtOAc. The combined organic extracts were dried ($MgSO_4$), filtered, and concentrated in vacuo leaving a yellow foam (92 mg). The product was purified by $SiO_2$ column chromatography, using MeOH in dichloromethane eluent. The resulting white foam was suspended in a little acetonitrile and heated to boiling until it dissolved. Upon cooling slowly cool to room temperature, crystals of the desired amino-pyriminyl ether precipitated out. These were collected by vacuum filtration with a Buchner funnel providing the title compound (57 mg), mp: 201-202° C.

Example 3

Synthesis of 1-methyl-7-(2-morpholin-4-ylmethyl-pyrimidin-4-yloxy)-1H-indole-2-carboxylic acid (5-tert-butyl-3-methanesulfonylamino-2-methoxyphenyl)-amide

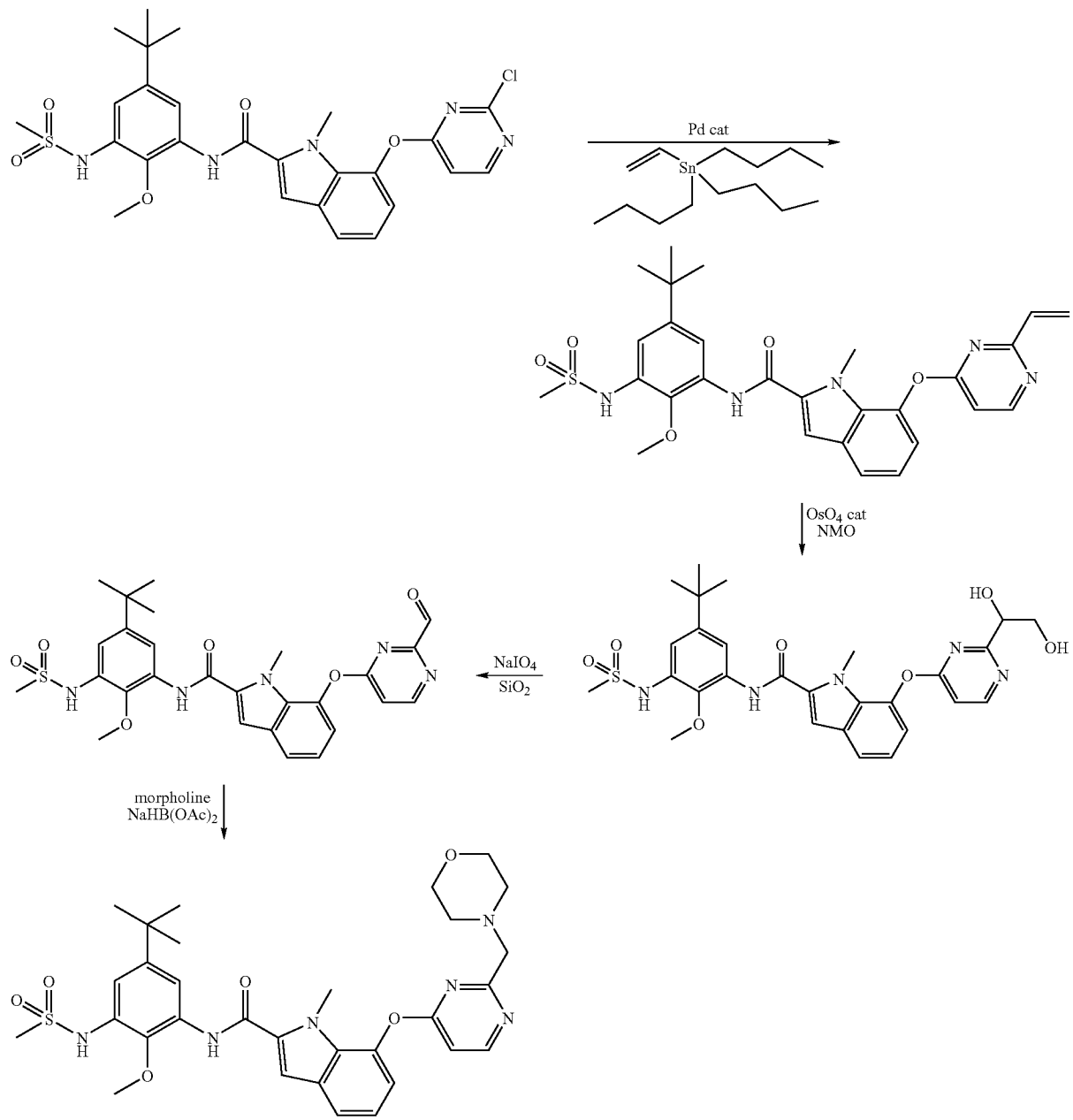

3

The 2-chloropyrimidinyl ether intermediate (500 mg, 0.896 mmol) (see Example 1), vinyltributyltin (600 mg, 1.89 mmol), BHT (20 mg), and (PPh$_3$)$_4$Pd (50 mg, 0.045 mmol) were suspended in degassed toluene (10 mL) under argon and heated to 115° C. for 3 h. The reaction mixture was cooled, diluted with EtOAc (100 mL), washed with brine (10 mL), and dried over MgSO$_4$. Silica gel chromatography (gradient elution, 0% to 80% EtOAc in hexanes) provided the desired 2-vinylpyrimidinyl ether intermediate (302 mg, 61%) as a pale yellow solid.

The 2-vinylpyrimidinyl ether (152 mg, 0.277 mmol) was dissolved in 8:1 acetone/water (10 mL). N-methylmorpholine-N-oxide (150 mg, 1.28 mmol) and OsO$_4$ (50 μL of a 2.5 wt % solution in tert-butanol) were added and the reaction was stirred at room temperature for 6 h. Sodium sulfite (250 mg) in water (20 mL) was added, and the solution was stirred at room temperature for 15 min. The reaction mixture was extracted with dichloromethane (4×20 mL), and the combined organic extracts dried over Na$_2$SO$_4$ and concentrated. Recrystallization from dichloromethane/hexanes provided the desired diol as a white powder (105 mg, 65%).

To a vigorously stirred suspension of silica gel (20 g) in dichloromethane (80 mL) was added a solution of sodium periodate (1.40 g, 6.55 mmol) in water (10 mL) over two min. A solution of the diol (1.25 g, 2.14 mmol) in dichloromethane (10 mL) was then added in one portion. After stirring at room temperature for 2 h, the mixture was filtered through a sintered glass frit with copious dichloromethane and EtOAc washings. The filtrate was dried over $MgSO_4$ and concentrated to provide the desired aldehyde as a pale brown solid (1.08 g, 91%).

To a vigorously stirred solution of the aldehyde (52 mg, 0.094 mmol), morpholine (200 μL), and acetic acid (150 μL) in 1,2-dichloroethane (4 mL) was added sodium triacetoxyborohydride (100 mg, 0.472 mmol). The resulting mixture was stirred at room temperature for 16 h. Saturated $NaHCO_3$ (1 mL) and brine (3 mL) were added and the mixture was stirred for a further 10 min. Extraction with dichloromethane (3×20 mL) was followed by drying ($MgSO_4$), and removal of the solvent. Silica gel chromatography (gradient elution, 0 to 10% MeOH in dichloromethane, 0.3% $NH_4OH$) provided the title compound as an off-white solid (40 mg, 68%).

Example 4

Synthesis of 1-methyl-7-(pyrimidin-4-yloxy)-1H-indole-2-carboxylic acid (5-tert-butyl-3-methanesulfonylamino-2-methoxy-phenyl)-amide

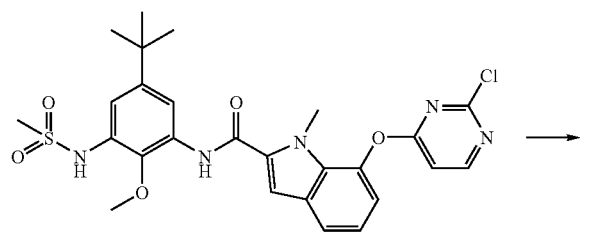

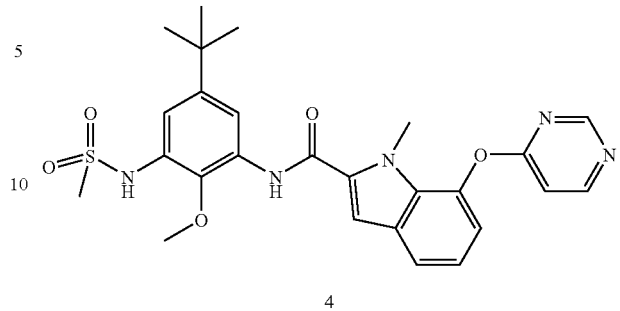

4

The 2-chloropyrimidinyl ether intermediate (100 mg, 0.179 mmol) (see Example 1) was dissolved in a mixture of EtOH and $CH_3CN$ (4:1, total 10 mL, using heat gun to complete dissolution). The reaction was cooled to room temperature under $N_2$ then 10% palladium-on-carbon (35 mg) was added and the reaction vessel was purged with $H_2$ several times. The reaction was stirred under $H_2$ (balloon). After stirring at room temperature for 4 h the reaction was filtered through diatomaceous earth and washed with $CH_3CN$. The solvents were removed in vacuo and the residue dissolved in $CH_2Cl_2$ (not totally soluble) and purified by flash column chromatography using EtOAc/hexanes as eluent mixtures, providing 24 mg of the title compound.

Example 5

Synthesis of 1-methyl-7-[2-(2-morpholin-4-yl-ethoxy)-pyrimidin-4-yloxy]-1H-indole-2-carboxylic acid (5-tert-butyl-3-methanesulfonylamino-2-methoxy-phenyl)-amide

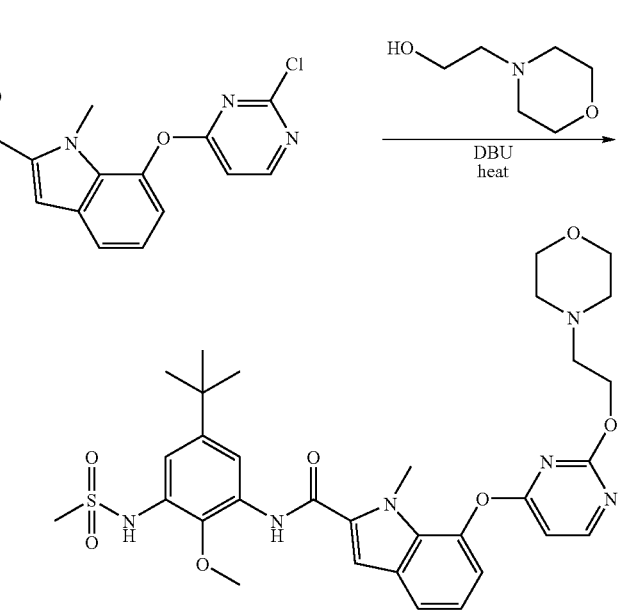

5

The chloropyrimidinyl ether intermediate (see Example 1) (0.250 g, 0.448 mmol) was dissolved in 5 mL CH$_3$CN in a 15 mL pressure tube. In a single portion, a mixture of 4-(2-hydroxyethyl)morpholine (0.080 g, 0.61 mmol) and DBU (0.11 g, 0.73 mmol) were added. The tube was washed down with 5 mL CH$_3$CN, sealed, and heated to about 95° C. (oil bath temp) for 48 h. The oil bath was raised to 110° C. and heating continued another 18 h. The reaction was allowed to cool, stripped to an amber oil and partitioned between EtOAc and water. The organic phase was washed with water, then brine, and dried over MgSO$_4$. The organic layer was stripped again to approximately 300 mg of amber oil, absorbed onto silica, and the product purified by flash column chromatography on SiO$_2$ using 5-25% iPrOH in CH$_2$Cl$_2$ as eluents. Concentration of the product-rich fractions afforded 40 mg of the title compound.

Example 6

Synthesis of 1-methyl-7-(2-methylcarbamoyl-pyridin-4-yloxy)-1H-indole-2-carboxylic acid (5-tert-butyl-3-methanesulfonylamino-2-methoxy-phenyl)-amide

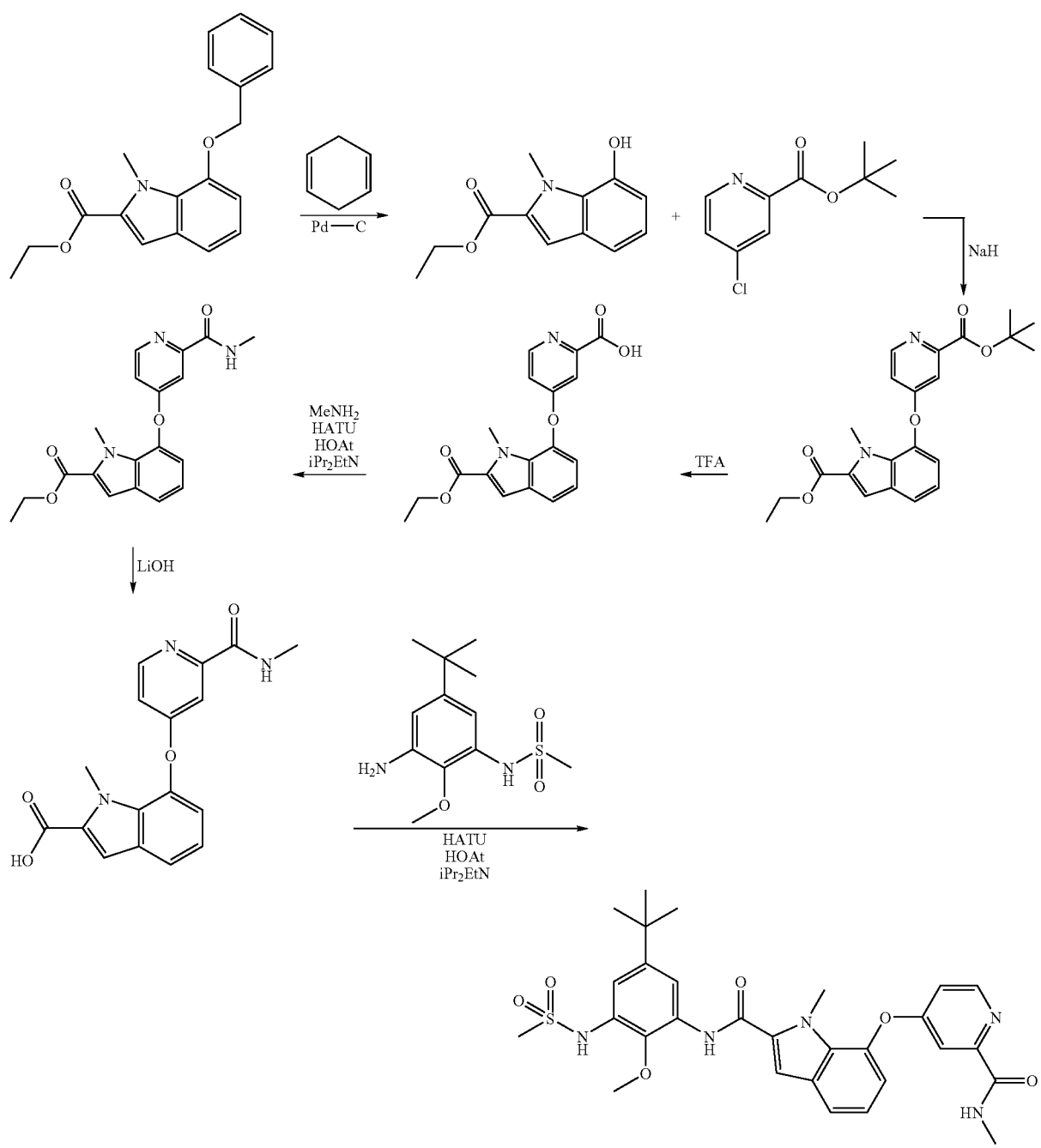

To a solution of the indole ester intermediate (see Example 1) (1.26 g, ~4 mmol) in 25 mL of EtOAc was added 10% Pd/C (250 mg). The reaction vessel was purged with N$_2$. and 1,4-cyclohexadiene (1.92 mL, 20.5 mmol) was added via syringe. The reaction mixture was heated to reflux for 5 h, then cooled to room temperature, filtered through a pad of diatomaceous earth, and rinsed with EtOAc. The resulting solution was evaporated to afford a pink solid which was purified by column chromatography on SiO$_2$ (4:1 hexanes-EtOAc) to give 740 mg of the desired 7-hydroxy-indole intermediate.

To a solution of the 7-hydroxyindole (200 mg, 0.912 mmol) in 2 mL of dry THF was added NaH (40 mg of a 60% dispersion in mineral oil) resulting in a deep blue solution. A solution of 4chloropyridine-2carboxylic acid t-butyl ester (256 mg, 1.20 mmol) in 1 mL of DMF was added and the mixture was heated to 120° C. under N$_2$ for 5 h. After cooling down, the reaction mixture was diluted with EtOAc, washed with water, brine, dried (Na$_2$SO$_4$) and filtered. After removal of solvents, the residue was purified by column chromatography on silica gel, eluting with 4:1 hexanes-EtOAc to give 50 mg of the desired diester.

The above diester (170 mg, 0.43 mmol) was dissolved in 4 mL CH$_2$Cl$_2$, and 1,3-dimethoxybenzene and 1 mL of TFA were added and the reaction was stirred overnight. After removal of the solvents, water was added to the oily residue and the pH adjusted to 3-4 with NaHCO$_3$ and extracted with CH$_2$Cl$_2$. The extracts were washed with brine, dried (Na$_2$SO$_4$) and filtered. After removal of the solvents, the desired carboxylic acid was used in next step without further purification.

To a solution of the carboxylic acid (160 mg, 0.47 mmol) in 2 mL of DMF were added Hunig's base (200 uL, 1.15 mmol), HATU (226 mg, 0.576 mmol), HOAt (8.2 mg, 0.06 mmol) and MeNH$_2$ (0.5 mL of a 2.0 M solution in THF, 1 mmol) successively. The reaction was stirred overnight, then diluted with EtOAc, washed with water, brine, and dried (Na$_2$SO$_4$). After removal of the solvent, the residue was purified by column chromatography on SiO$_2$ (3:1 hexanes-EtOAc) to give 120 mg of the desired methylamide.

The above methylamide (110 mg, 0.311 mmol) was dissolved in 3 mL of THF and LiOH (26 mg, 0.62 mmol) was added as a solution in 1 mL water. The mixture was stirred at room temperature overnight. The reaction mixture was partitioned between CH$_2$Cl$_2$ and water, and the water was separated and adjusted to pH to 3-4 with HCl and extracted again with CH$_2$Cl$_2$. The combined organic layers were washed with brine, dried (Na$_2$SO$_4$) and filtered. After removal of the solvent, the carboxylic acid was obtained as a solid which was used in next step without any purification.

To a suspension of the above carboxylic acid (60 mg, 0.185 mmol) in 1.5 mL of DMF was added Hunig's base (87 uL, 0.50 mmol). After 5 min, HATU (90.2 mg, 0.23 mmol) and HOAt (5.0 mg, 0.037 mmol) were added followed by N-(3-amino-5-tert-butyl-2-methoxy-phenyl)-methane-sulfonamide (51.8 mg, 0.190 mmol). The mixture was stirred overnight and was then diluted with EtOAc, washed with water, brine, dried (Na$_2$SO$_4$) and concentrated in vacuo. The crude product was purifed twice by flash column chromatography (3-5% MeOH in CH$_2$Cl$_2$) to give 85 mg of the desired product with some impurities. Final purification by reverse-phase HPLC (water:acetonitrile) gave 45 mg of the title compound.

Example 7

Synthesis of 1-methyl-7-(2-morpholin-4-ylmethyl-pyridin-4-yloxy)-1H-indole-2-carboxylic acid (5-tert-butyl-3-methanesulfonylamino-2-methoxy-phenyl)-amide

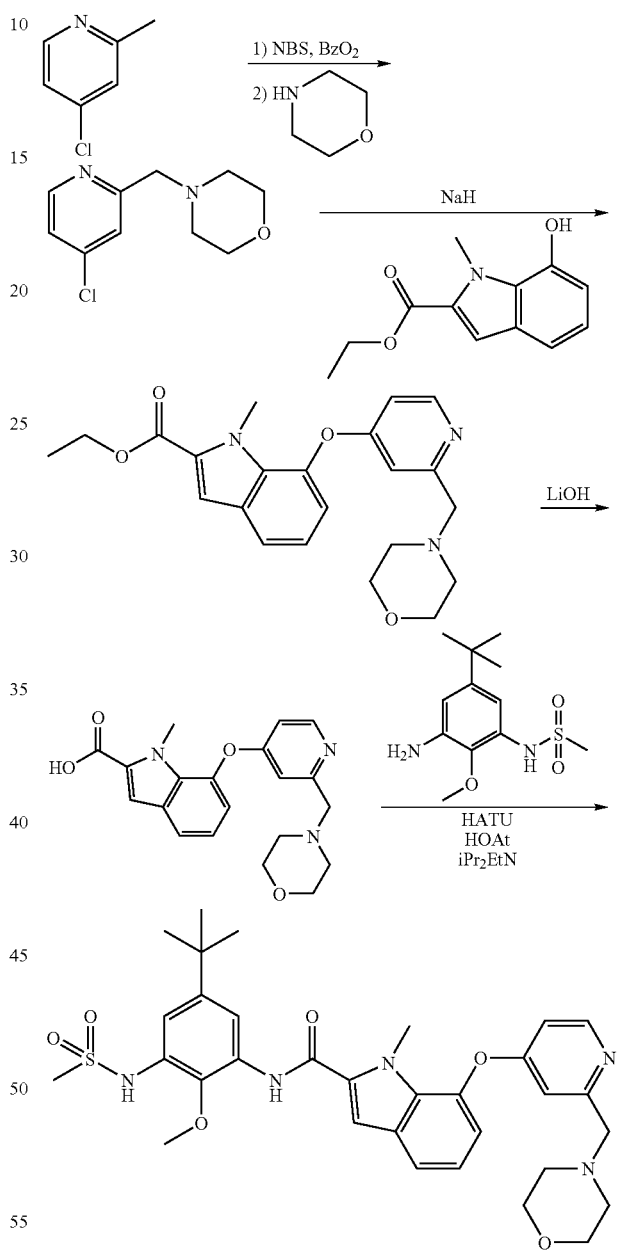

7

A mixture of the 2-methyl-4-chloropyridine (1.00 g, 7.84 mmol), NBS (1.42 g, 8.00 mmol) and benzoyl peroxide (~10 mg) in 10 mL of CCl$_4$ was heated at reflux for 5 h. After cooling down, the reaction mixture was filtered and filtrate was concentrated to give the crude products mixture, which was dissolved in DMF and treated with morpholine (1.00 mL) and K$_2$CO$_3$ (1 g). The mixture was stirred overnight. The mixture was then diluted with EtOAc, washed with water, brine, dried over Na$_2$SO$_4$, filtered and concentrated in vacuo. The crude product was purified by column chromatography on SiO$_2$ to give 400 mg of the desired 2-morpholinomethyl-4-chloropyridine.

To a solution of the 7-hydroxyindole ester (see Example 6) (473.6 mg, 2.16 mmol) in 10 mL of dry DMF was added NaH (86.4 mg of a 60% dispersion in mineral oil, 2.16 mmol), resulting in a deep blue solution. A solution of the 4-chloropyridine intermediate from above (380 mg, 1.79 mmol) in 3 mL of DMF was added and the mixture was heated to 140° C. in a sealed tube for 4.5 h. After cooling down, the reaction mixture was diluted with EtOAc, washed with water, brine, dried (Na$_2$SO$_4$) and filtered. After removal of solvent, the residue was purified by column chromatography on silica gel eluting with 1-4% MeOH in CH$_2$Cl$_2$ to give 240 mg of a mixture of unreacted chloropyridine and the desired ether intermediate, which was used in next step without further purification.

The mixture of the above ether and unreacted chloropyridine was dissolved in 3 mL of THF and was treated with 1 mL of aqueous LiOH (60 mg) solution. The reaction mixture was stirred overnight and then was concentrated in vacuo. The residue was diluted with 1 M NaOH and extracted with ether to remove unreacted 7-hydroxyindole ester and chloropyridine. The aqueous layer was then acidified with 2 M HCl to pH 4-5 and extracted with CH$_2$Cl$_2$ 6 times. The combined organic extracts were dried (Na$_2$SO$_4$), filtered and concentrated to give 68 mg of the desired indole acid.

To a solution of the indole acid (65.0 mg, 0.177 mmol) in 2 mL of DMF was added Hunig's base (87 uL, 0.50 mmol). After 5 min, HATU (90.2 mg, 0.23 mmol) and HOAt (5 mg, 0.037 mmol) were added, and then N-(3-amino-5-tert-butyl-2-methoxy-phenyl)-methanesulfonamide (49 mg, 0.180 mmol). The mixture was stirred overnight. The reaction mixture was diluted with EtOAc, washed with water, brine, dried (Na$_2$SO$_4$), filtered and concentrated in vacuo. The crude product was purified by preparative TLC (10% MeOH in DCM) to give 35 mg of product, which was purified by reverse-phase HPLC to give 20 mg of the title compound.

Example 8

Synthesis of 7-(2-dimethylaminomethyl-pyridin-4-yloxy)-1-methyl-1H-indole-2-carboxylic acid (5-tert-butyl-3-methanesulfonylamino-2-methoxy-phenyl)-amide

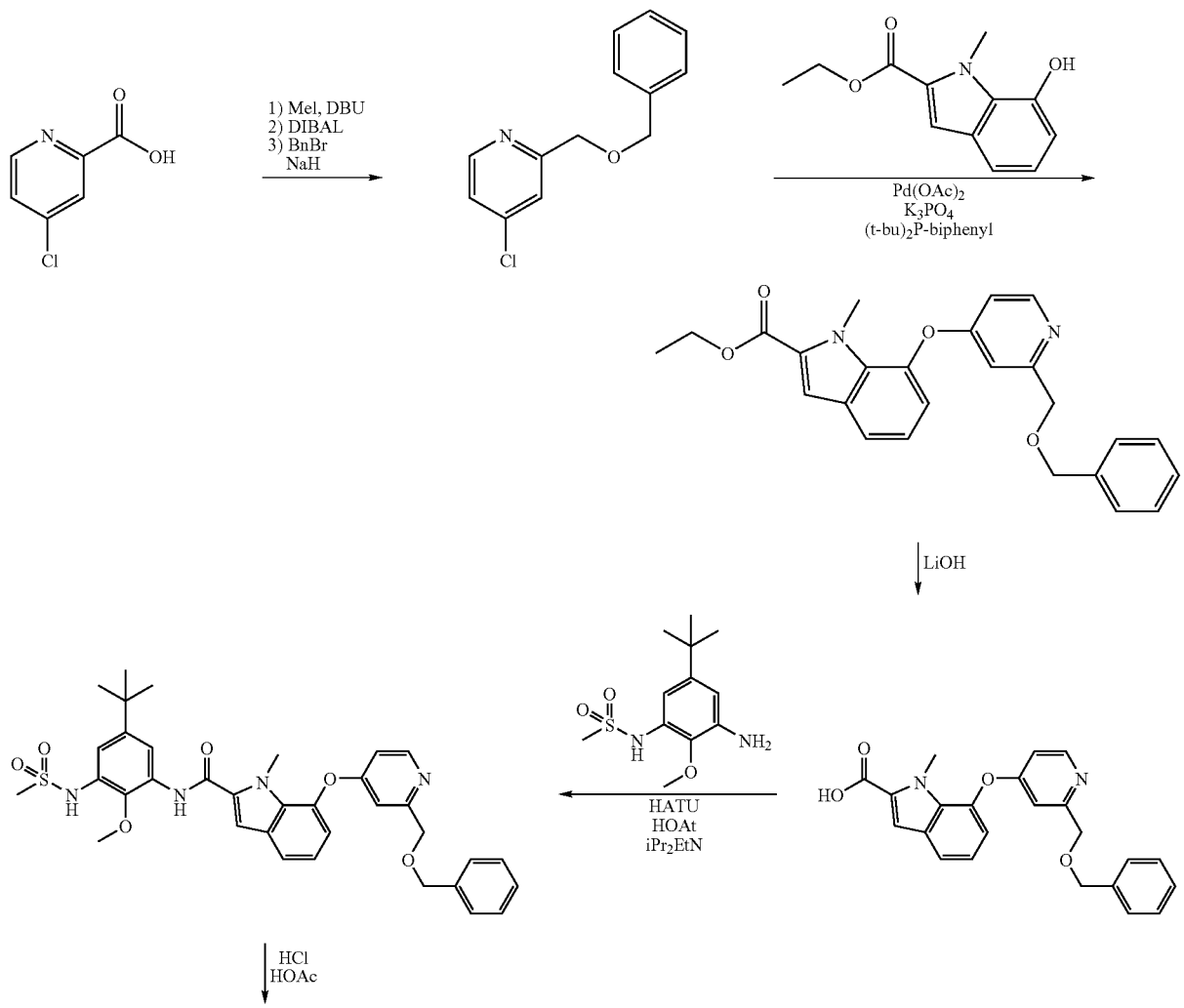

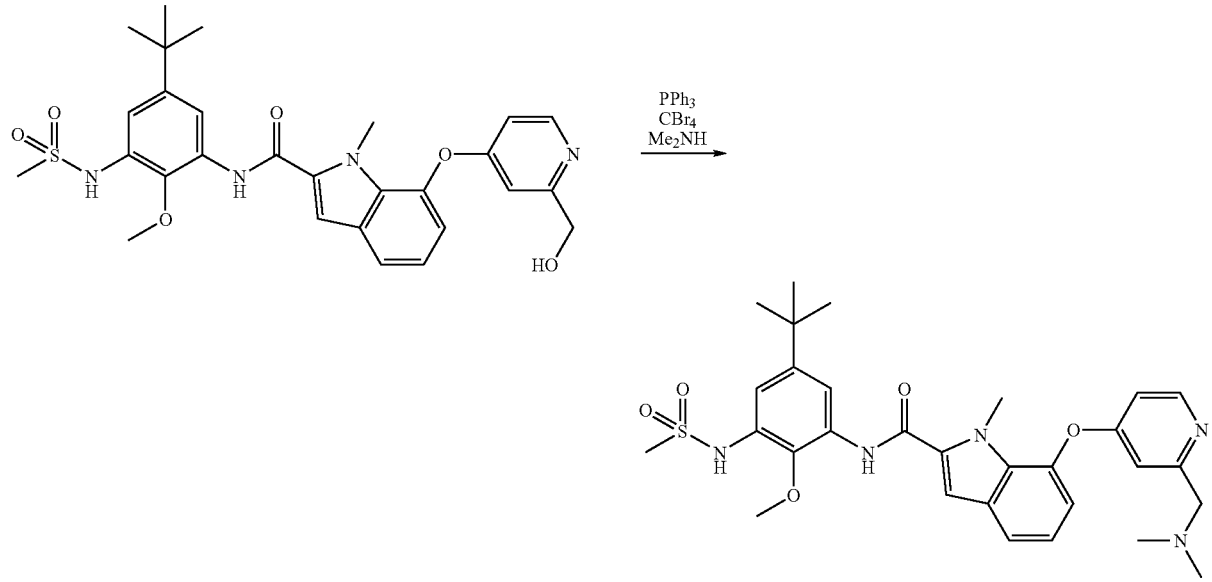

8

A mixture of 4-chloropyridine-2-carboxylic acid (2.00 g, 12.69 mmol), methyl iodide (1.25 mL, 20.0 mmol) and DBU (3.34 mL, 22.0 mmol) in 20 mL of dry acetonitrile was stirred over 2 days. The reaction mixture was diluted with ether, washed with water, brine, dried over $Na_2SO_4$ and concentrated. The residue was purified by chromatography on silica gel to give 1.6 g of the desired methyl ester.

To a solution of DIBAL in toluene (1 M, 12.3 mL, 12.3 mmol) and THF (1:1) in an ice-salt bath, was added a solution of the above ester (700 mg, 4.10 mmol) in 10 mL of THF. After addition, the reaction mixture was allowed to warm up to room temperature and stir for 3 h. The mixture was then poured into crushed ice with 5 mL of 4M NaOH, extracted with EtOAc, dried over $Na_2SO_4$ and concentrated in vacuo to give 450 mg of the desired alcohol, which was used in next step without purification.

To a solution of the above alcohol (430 mg, 3.0 mmol) in DMF (10 mL) was added NaH (144 mg of a 60% dispersion in mineral oil, 3.60 mmol) and the mixture was then cooled in an ice bath. Benzyl bromide (437 uL, 3.60 mmol) was then added and the mixture was stirred at room temperature for 3 h. After normal aqueous work-up and short column chromatographic purification, 600 mg of desired benzyl ether was obtained.

A Schlenk tube was charged with $Pd(OAc)_2$ (16 mg, 0.07 mmol), $K_3PO_4$ (525 mg, 2.40 mmol), di-t-butylbiphenylphosphine (42 mg, 0.14 mmol) and the 7-hydroxyindole ester (see Example 6) (307 mg, 1.4 mmol), and capped with a septum and purged with argon. A solution of the benzyl ether from above (270 mg, 1.16 mmol) in 3 mL of toluene was then added via syringe. The mixture was heated at 100° C. with stirring under argon for 6 h. The reaction mixture was filtered through a layer of diatomaceous earth and the solid residue was rinsed with $CH_2Cl_2$. The combined filtrate was concentrated. The crude product was purified by column chromatography to give 61% yield of the desire indole ether.

To a solution of the indole ether (400 mg, 0.96 mmol) in 8 mL THF was added a solution of LiOH (120 mg, 2.86 mmol) in 2.5 mL of $H_2O$. The mixture was stirred overnight, then was diluted with water, acidified with 2 N HCl to pH 4-5, and extracted with $CH_2Cl_2$. The combined extracts were washed with brine, dried over $Na_2SO_4$, and concentrated in vacuo to give 360 mg of desired carboxylic acid, which was pure enough for the next step without purification.

To a solution of the indole carboxylic acid (360 mg, 0.93 mmol) in 4 mL of DMF was added Hunig's base (418 uL, 2.4 mmol). After 5 min, HATU (439 mg, 1.12 mmol) and HOAt (12 mg, 0.09 mmol) were added and then N-(3-amino-5-tert-butyl-2-methoxyphenyl)-methanesulfonamide (253 mg, 0.93 mmol). The mixture was stirred overnight. The reaction mixture was diluted with EtOAc, washed with water, brine, dried ($Na_2SO_4$) and concentrated in vacuo. The crude product was purified by column chromatography (1:2 hexanes-EtOAc) to give 390 mg of the desired amide.

To a solution of the amide (390 mg, 0.61 mmol) in 4 mL of HOAc was added 2 mL of concentrated HCl and the mixture was heated at 100° C. for 3 h. After cooling down, the reaction mixture was poured into crushed ice, adjusted to pH to 5-6, extracted with EtOAc, washed with saturated aqueousd $NaHCO_3$, brine, and dried over $Na_2SO_4$. After removal of the solvent, the residue was purified by column chromatography (3-5% MeOH in $CH_2Cl_2$) to give 180 mg of the desired debenzylated pyridine-methanol.

To a solution of the pyridine-methanol (63 mg, 0.11 mmol) and $CBr_4$ (76 mg, 0.23 mmol) in 2 mL of $CH_2Cl_2$ was added $Ph_3P$ (36 mg, 0.14 mmol) at 0° C. and the mixture was stirred at 0° C. for 1 h. The reaction mixture was concentrated in vacuo and the resulting yellow foam was dissolved in 2 mL DMF, to which was added 1 mL of 2 M $Me_2NH$ in THF and solid $K_2CO_3$. The mixture was stirred at room temperature for 3 h. The reaction mixture was diluted with EtOAc, washed with water, brine, dried ($Na_2SO_4$) and concentrated in vacuo. The crude product was purified by column chromatography to give 15 mg of the title compound.

Example 9

Synthesis of 1-methyl-7-(2-methylamino-pyrimidin-4-yloxy)-1H-indole-2-carboxylic acid (5-tert-butyl-2-methoxy-3-methylcarbamoyl-phenyl)-amide

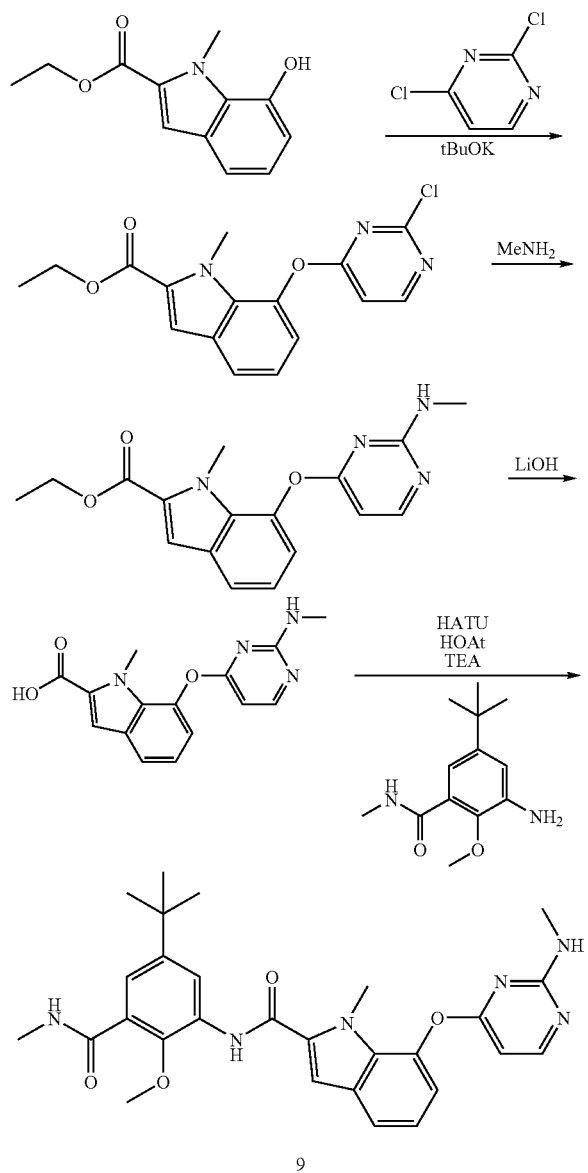

To a solution of 7-hydroxyindole ester (see Example 6) (2.10 g, 10 mmol) in DMSO (25 mL) was added t-BuOK solution in THF (1.0 M, 10 mL, 10 mmol) at room temperature. The reaction color changed from red to green. 2,4-Dichloropyrimidine (1.50 g, 10 mmol) was then added. The reaction mixture was heated to 70° C. for 3 h. The reaction was cooled, diluted with H$_2$O and extracted with EtOAc. The combined organics were washed with water and brine, dried over MgSO$_4$, filtered and concentrated to give a crude solid. The solid was triturated with 30% EtOAc/hexanes and filtered to give 1.4 g of the desired ether. The filtrate was concentrated down and purified by column chromatography on SiO$_2$ (15%-40% EtOAc/hexanes eluent) to give an additional 1.2 g of the ether intermediate as a white solid, for a combined yield of 2.6 g (78%).

To a solution of the above chloro-pyrimidinyl ether (1.00 g, 3.01 mmol) in 15 mL anhydrous THF in a sealed tube was added 6.0 eq of MeNH$_2$ solution in THF. The reaction was heated at 70° C. overnight. It was then cooled down to room temperature, diluted with water and extracted with EtOAc. The organics were washed with brine, dried, filtered and concentrated to give a foam, which was purified by flash column chromatography on SiO$_2$ (20%-50% EtOAc/hexanes eluent) to give 812 mg of desired methylamino-pyrimidine intermediate.

To a solution of the above intermediate (812 mg, 2.49 mmol) in MeOH/THF (15 mL/15 mL) was added LiOH as an aqueous solution (313 mg in 2 mL of H$_2$O). The reaction color changed to light green. The reaction was sitrred at room temperature for 6 h, then concentrated in vacuo. Water was added, the mixture was washed with Et$_2$O and the organic layer was discarded. The aqueous phase was acidified to pH 3-4 with 3N HCl and extracted with EtOAc. The combined organic extracts were dried, filtered (MgSO$_4$) and concentrated down to give 580 mg of the indole carboxylic acid as a pale pink solid.

To a solution of the above indole carboxylic acid (122 mg, 0.41 mmol) in DMF were added HATU (141 mg, 0.37 mmol), TEA (104 uL, 0.74 mmol) and HOAt (25 mg, 0.19 mmol). After 10 min, the aniline intermediate (88 mg, 0.37 mmol) was added in one portion. The mixture was stirred at room temperature for 8 h. The reaction was then diluted with EtOAc and washed with water. Most starting aniline was removed by washing with 0.5 N aqueous HCl. The resulting organics were dried (MgSO$_4$), filtered and concentrated to give an oil which was purified by column chromatography on SiO$_2$ (3%-10% MeOH/CH$_2$Cl$_2$ eluents) followed by preparative TLC to give 110 mg of the title compound.

Example 10

Synthesis of 1-methyl-7-[2-(2-morpholin-4-yl-ethyl)-pyrimidin-4-yloxy]-1H-indole-2-carboxylic acid (5-tert-butyl-3-methanesulfonylamino-2-methoxy-phenyl)-amide

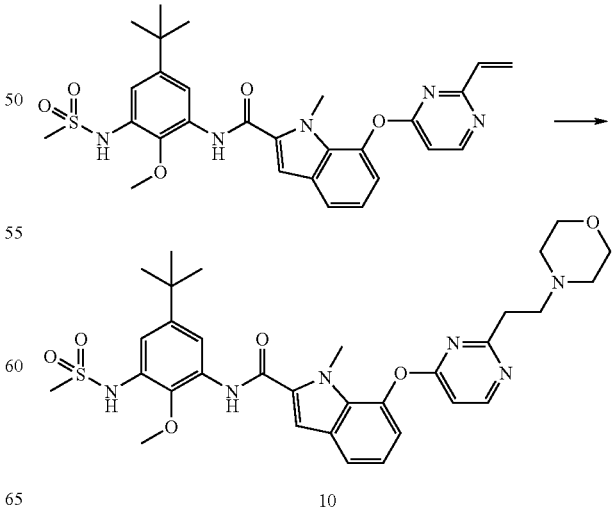

To a suspension in EtOH (3 mL) of the olefin illustrated above (200 mg, 0.364 mmol) was added morpholine (65 µL, 0.75 mmol) and acetic acid (35 µL, 0.61 mmol). The mixture was heated to 80° C. under nitrogen for 4 h, after which time a homogeneous solution was obtained. The reaction was diluted with dichloromethane (10 mL) and stirred over anhydrous K₂CO₃ for 30 min. The solution was then filtered and concentrated. Trituration of the residue with Et₂O provided the product (221 mg, 95%) as a tan powder.

Example 11

Synthesis of 1-methyl-7-[2-(4-methyl-piperazin-1-yl)-pyrimidin-4-yloxy]-1H-indole-2-carboxylic acid (3-methanesulfonylamino-2-methoxy-5-trifluoromethyl-phenyl)-amide

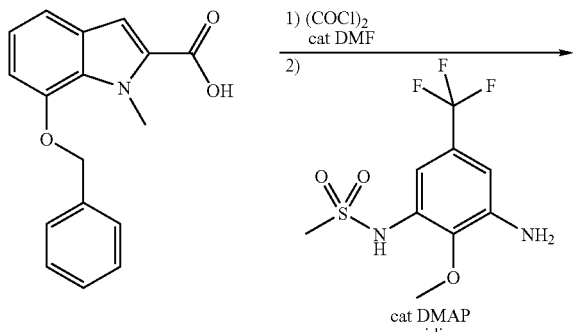

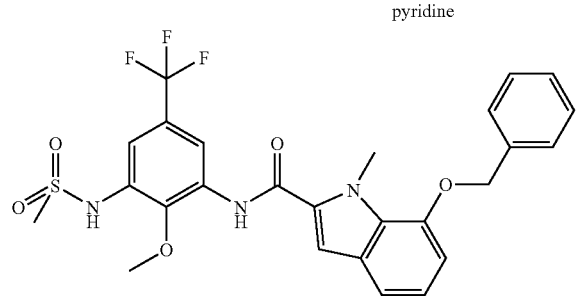

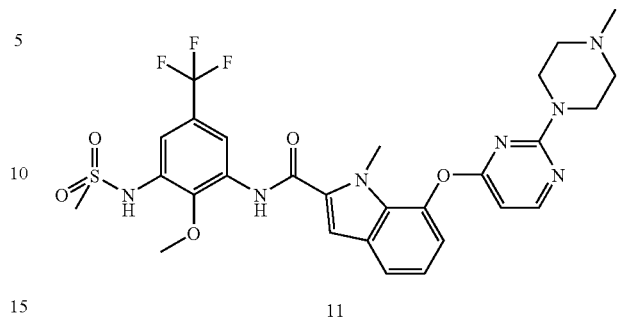

To a suspension of the indole carboxylic acid (2.10 g, 7.47 mmol) in dichloromethane (40 mL) was added oxalyl chloride (6.0 mL of a 2.0 M solution in dichloromethane, 12 mmol) and DMF (10 µL) under an atmosphere of dry N₂. After stirring at ambient temperature for 1.5 h, the resulting yellow solution was concentrated in vacuo to provide the crude acid chloride as a yellow powder. This material was dissolved in THF (50 mL), and to this solution was added N-(3-amino-5-tert-butyl-2-methoxy-phenyl)-methanesulfonamide (2.13 g, 7.50 mmol), pyridine (971 µL, 12.0 mmol) and DMAP (50 mg). The reaction was stirred at ambient temperature for 4 days, then taken up in dichloromethane (300 mL), washed with saturated NaHCO₃ (40 mL), and concentrated in vacuo. The resulting solids were triturated with ether to provide the product (2.94 g, 72%) as an analytically pure white powder.

O-de-benzylation and further transformation to the title compound were performed as previously described (Example 1) to afford the title compound.

Example 12

Synthesis of N-[3-amino-2-methoxy-5-(1-methylcyclopropyl)-phenyl]methanesulfonamide

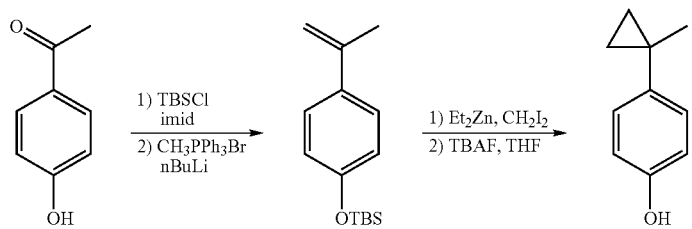

-continued

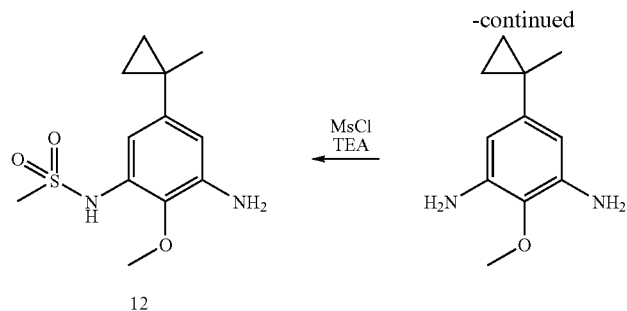

12

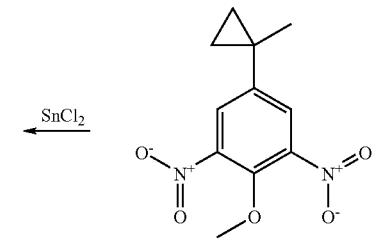

To a solution of 4-hydroxyacetophenone (10.0 g, 73.5 mmol) in DMF (74 mL) was added imidazole (12.0 g, 176.3 mmol) and tert-butyldimethylsilyl chloride (13.3 g, 88.1 mmol). The colorless solution was stirred for 0.75 h at room temperature then quenched with saturated aqueous NaHCO$_3$. The aqueous phase was extracted with hexanes and the combined organic layers were washed with saturated aqueous NaHCO$_3$. The organic layers were dried over sodium sulfate, filtered, and concentrated to provide the silyl ether (18.0 g, 98%) as a white solid which was utilized without further purification.

Methyl(triphenylphosphonium) bromide (17.1 g, 48.0 mmol) was suspended in THF (96 mL) and cooled to 0° C. n-Butyllithium (2.5 M in hexane, 19.2 mL, 48.0 mmol) was added dropwise to the mixture. The red solution was stirred at room temperature for 0.5 h. The acetophenone silyl ether (10.0 g, 40.0 mmol) from above was added. The solution turned bright yellow and a white precipitate formed. The mixture was stirred for 1 h at room temperature and then the solution was quenched with saturated aqueous NaHCO$_3$. The aqueous phase was extracted with diethyl ether and the combined organic layers were washed with saturated aqueous NaHCO$_3$. The organic layers were dried over sodium sulfate, filtered and concentrated. The resulting mixture was eluted through a plug of silica gel (hexanes) and the filtrate was concentrated to provide the styrene (8.36 g, 84%) as a colorless oil.

Diethylzinc (1.0 M in hexanes, 69 mL, 69 mmol) was added to a solution of the above styrene intermediate (6.85 g, 27.6 mmol) in dichloroethane at 0° C. Diiodomethane (11.2 mL, 138 mmol) was then added dropwise to the solution and the resulting mixture was stirred at 0° C. for 0.5 h and allowed to warm to room temperature for 2 h. The opaque mixture was quenched with saturated aqueous NH$_4$Cl. The aqueous phase was extracted with methylene chloride and the combined organic layers were washed with saturated aqueous NaHCO$_3$. The organic layers were dried over sodium sulfate, filtered through diatomaceous earth, and concentrated. The crude residue was dissolved in THF (50 mL) and TBAF (1.0 M in THF, 28 mL, 28 mmol) was added at room temperature. The solution was stirred for 2 h and then quenched with aqueous 1.0 M HCl. The aqueous phase was extracted with EtOAc and the combined organic layers were washed with saturated aqueous NaHCO$_3$. The organic layers were dried over sodium sulfate, filtered and concentrated. Purification by silica-gel chromatography (1% 2-propanol/12% EtOAc in hexanes) provided the phenol (2.77 g, 68%) as a white solid:

(NO)18-crown-6. H(NO$_3$)$_2$[1] (18.0 g, 43.0 mmol) was added to a solution of phenol (2.77 g, 18.7 mmol) in EtOAc. The reaction mixture was heated to reflux for 5 min and then cooled to room temperature. The mixture was poured onto aqueous 1.0 M HCl.

The aqueous phase was extracted with diethyl ether. The combined organic layers were dried over sodium sulfate, filtered and concentrated. The residue was dissolved in acetonitrile/MeOH (9:1, 62 mL), cooled to 0° C. and N,N-diisopropylethylamine (13 mL, 74.8 mmol) was added slowly. The deep red solution was warmed to room temperature and trimethylsilyldiazomethane (2.0 M in hexane, 18.7 mL, 37.4 mmol) was added slowly to control nitrogen evolution. After stirring at room temperature for 0.5 h, the mixture was concentrated and partitioned between methylene chloride and saturated aqueous NH$_4$Cl. The aqueous layer was extracted with methylene chloride and the combined extracts were dried over sodium sulfate, filtered and concentrated. Purification by silica-gel chromatography (6% EtOAc in hexanes) provided the dinitroanisole (2.21 g, 47%) as a red oil.

Tin(II)chloride dihydrate (11.9 g, 52.6 mmol) was added to a solution of the above dinitroanisole (2.21 g, 8.76 mmol) in EtOAc (30 mL). The mixture was heated to reflux for 0.25 h upon which the solution became red in color. The solution was cooled to room temperature and poured onto aqueous 2.0 M NaOH. The aqueous phase was extracted with EtOAc and the combined organic layers were washed with saturated aqueous NaHCO$_3$. The organic layers were dried over sodium sulfate, eluted through a plug of silica gel (1% ammonium hydroxide in methylene chloride), and the filtrate was concentrated. The residue was dissolved in diethyl ether and extracted (3×) with 1.0 M HCl. The pH of the combined aqueous layers was adjusted to pH=12 with 2.0M NaOH and extracted with methylene chloride. The combined organic layers were dried over sodium sulfate, filtered and concentrated to provide diaminoanisole (860 mg, 52%) as a red oil.

Triethylamine (521 μL, 3.74 mmol) was added to a solution of the above diaminoanisole (718 mg, 3.74 mmol) in methylene chloride at −10° C. Methanesulfonyl chloride (290 μL, 3.74 mmol) was then added dropwise over a 10 min period and the resulting solution was allowed to slowly warm to room temperature over 2 h. The mixture was quenched with saturated aqueous NaHCO$_3$ and the aqueous layer was extracted with methylene chloride. The combined organic layers were dried over sodium sulfate, filtered and concentrated. Purification by silica gel chromatography (1% ammonium hydroxide/35% EtOAc in hexanes to 1% ammonium hydroxide/50% EtOAc in hexanes) provided a red solid which was triturated with a diethyl ether/hexanes (1:1) to yield the title compound (510 mg, 51%) as a pale brown solid, mp 144-146° C.

This intermediate can then be coupled to the indole core and reacted further by the procedures described in the examples above, to form desired analogous indole amides.

For example, the product of Example 12 was used to prepare the following compound:

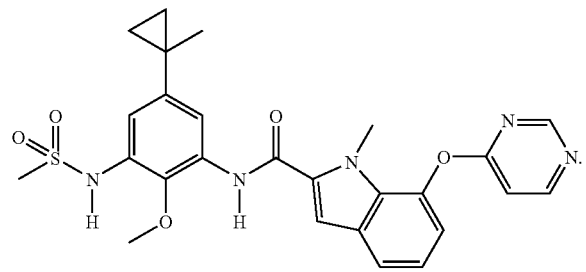

Example 13

Synthesis of
7-mercapto-1-methyl-1H-indole-2-carboxylic acid
ethyl ester

7-Hydroxy-1-methylindole-2-carboxylic acid ethyl ester (1.06 g; 0.005 mol) was dissolved in 8 mL DMF in a 3-neck round bottom flask under nitrogen purge. Diazabicyclo[2.2.2.]octane (DABCO) (1.12 g, 0.010 mol) and $Me_2NC$ (=S)Cl (1.236 g, 0.010 mol) were added sequentially, each in a single portion. The mixture was left stirring at room temperature overnight. A suspension formed. The reaction mixture was poured onto water and extracted 3× with EtOAc. The combined organic layers were washed 3× with water, then brine, then dried over $MgSO_4$, concentrated to a semi-solid, ca 1.6 g.

The above residue was taken up in hot i-PrOH (about 30 mL) and treated with charcoal. The solution was cooled overnight in a freezer, then the resulting beige solid was filtered off and washed with cold i-PrOH, then petroleum ether providing the desired thiocarbamate (0.92 g).

The above thiocarbamate (31 mg; 0.0001 mol) was added into a pressure tube, along with $Me_2NPh$ (0.63 mL; 0.005 mol) and a magnetic stir bar. The tube was heated in a microwave oven to 250° C. for 10 min. The reaction mixture was then poured onto 4 N aqueous HCl and the gummy precipitate was extracted with EtOAc. The solution was allowed to evaporate providing the desired isomerized intermediate.

The resulting intermediate can be hydrolyzed to form the desired thiol, which can then be further reacted by the methods described above for the analogous 7-hydroxyindole intermediate to form the desired thioether derivatives.

For example, the following compound may be prepared from the above thiol using the methods described in the above examples:

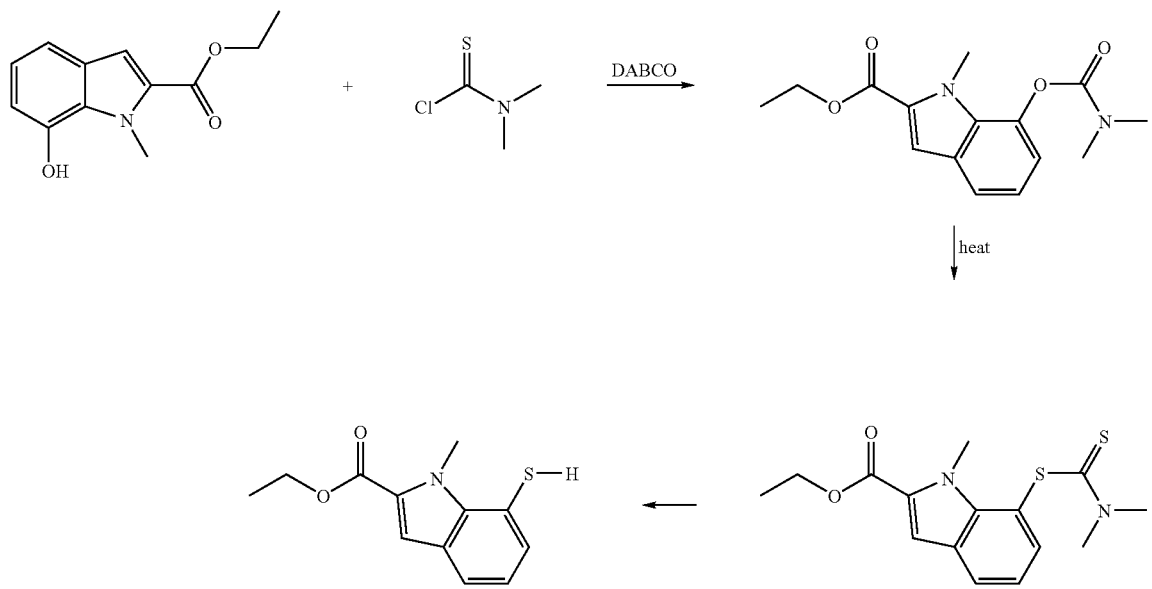

123

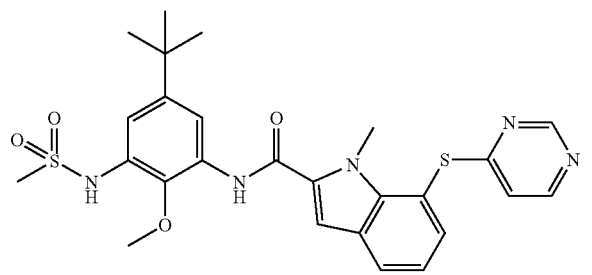

Example 14

Synthesis of
7-hydroxy-benzo[b]thiophene-2-carboxylic acid
methyl ester

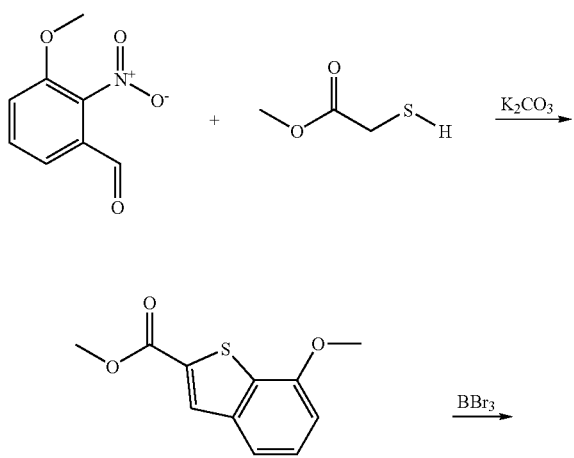

124

-continued

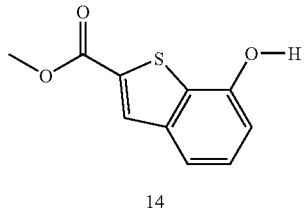

To a 150 mL heating flask was added 1 g (5.52 mmol) of 3-methoxy-2-nitro-benzaldehyde, 0.5 mL (5.7 mmol) of mercapto-acetic acid methyl ester, 1.8 g (13 mmol) of potassium carbonate and 50 mL of anhydrous DMF. The opaque, gold solution was stirred overnight at 60° C. in a sealed tube. After 14 h the reaction was poured into 200 mL of water, stirred 2 h, and extracted with EtOAc to provide 1 g (81%) of the desired intermediate, which was used without further purification.

Dissolved 1 g (4.5 mmol) of the above intermediate in about 50 mL $CH_2Cl_2$ in a 500 mL 3-neck round-bottom flask under nitrogen purge and cooled in an ice/acetone bath. Placed the $BBr_3/CH_2Cl_2$ solution (3 eq) in addition funnel, and added dropwise at such a rate that the temperature was maintained <5° C. throughout. Allowed to warm to room temperature and continued stirring overnight. The reaction was cooled back down in an ice/acetone bath and added 50 mL MeOH dropwise; initially very slowly, since it was exothermic. After the addition of MeOH was complete, the reaction was allowed to warm to room temperature and then concentrated in vacuo to obtain the title compound (900 mg, 93%).

The 7-hydroxybenzothiophene intermediate can then be reacted further as described in Examples above for 7-hydroxyindole to produce compounds of formula I Example 15

Synthesis of 1-methyl-7-(2-pyrrolidin-1-ylmethyl-pyridin-4-yloxy)-1H-indole-2-carboxylic acid (5-tert-butyl-3-methanesulfonylamino-2-methoxyphenyl)-amide

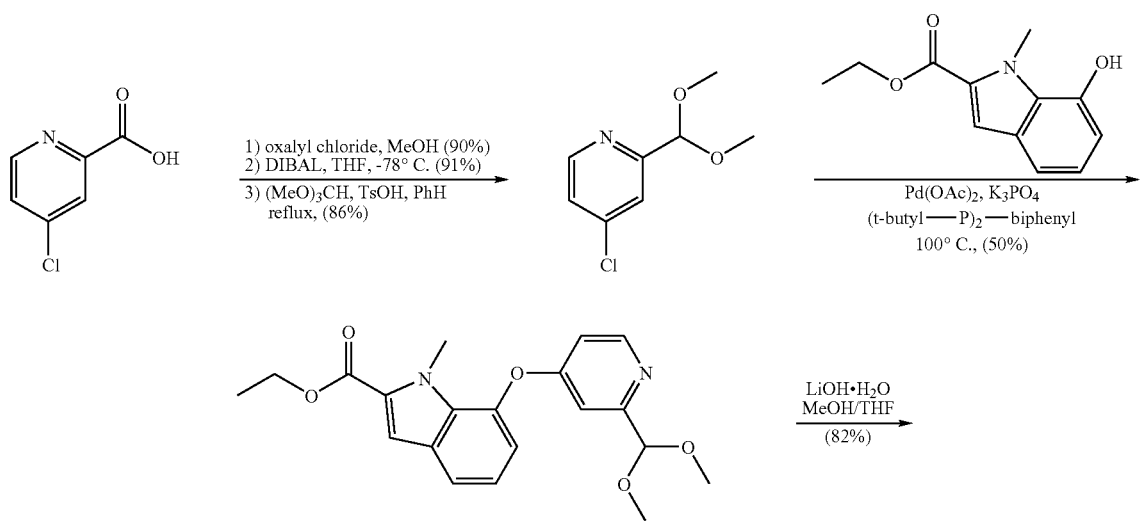

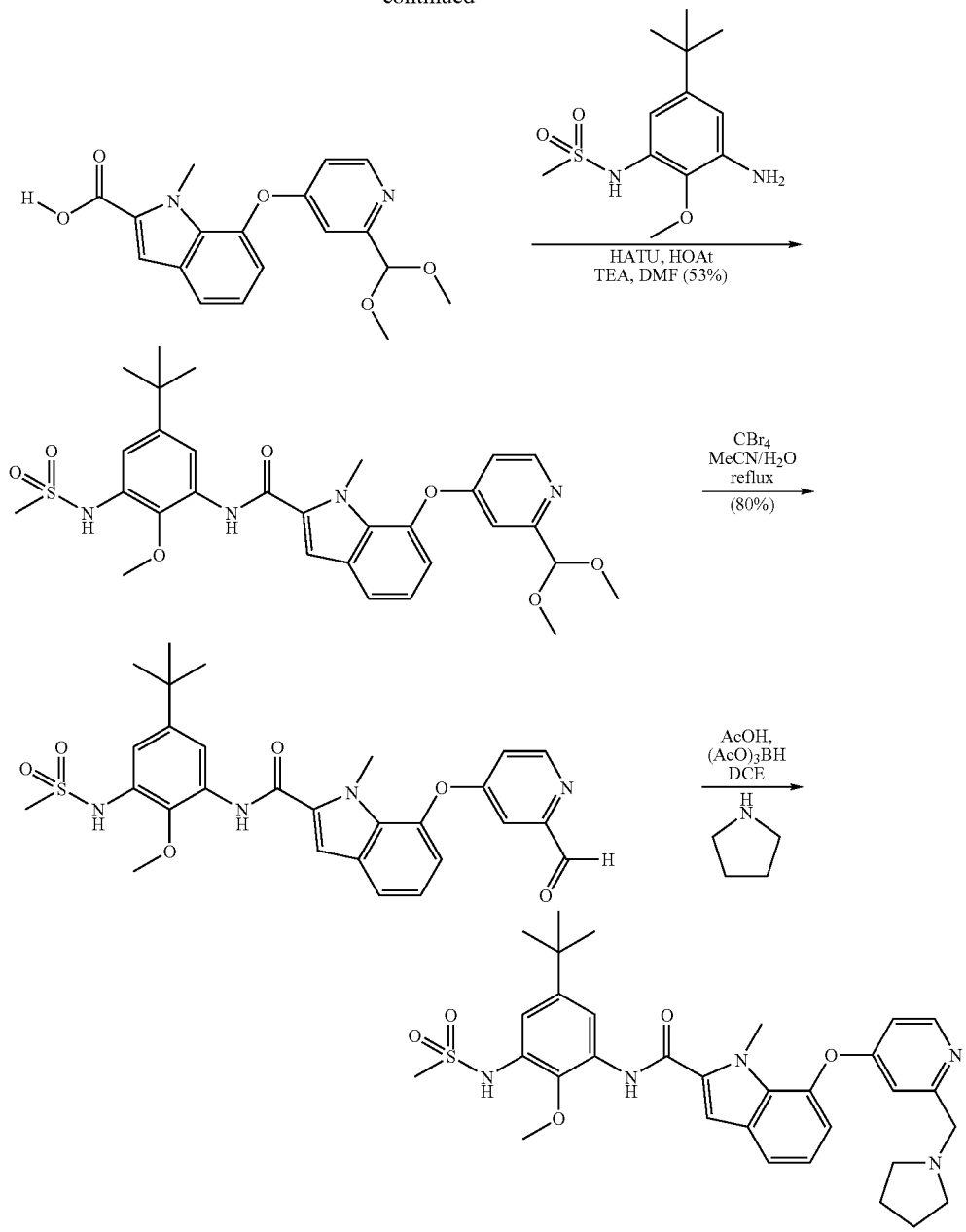

To a suspension of 4-chloropyridine-2-carboxylic acid (4.5 g, 29.0 mmol) in methylene chloride (120 mL) was added oxalyl chloride (3.0 mL, 1.2 eq) under $Ar_2$. The reaction was cooled to 0° C., added 500 uL of DMF. A large amount of gas was generated in situ. The reaction was stirred at room temperature for 1.5 h then concentrated. Dry MeOH (50 mL) was added to the crude acyl chloride residue. The reaction was stirred at room temperature for 0.5 h then quenched with $NaHCO_3$ (5%) to neutral, extracted with EtOAc, and washed with brine. The combined organics were dried over $MgSO_4$, filtered and concentrated in vacuo to give 5.0 g of crude solid which was triturated with 5% EtOAc/hexane to give the desired intermediate methyl ester as a light yellow solid (4.5 g, 90%).

To a solution of the above methyl ester (2.5 g, 14.6 mmol) in 100 mL of dry THF at −78° C. was added diisobutylaluminum hydride dropwise (1.0 M in THF, 29.1 mmol) and the reaction mixture was stirred at that temperature under $Ar_2$ for 2 h. The reaction was quenched with MeOH at −78° C. and then sodium potassium tartrate solution (~1.0 M, 180 mL) was added and the mixture was stirred and warmed up to room temperature over 1 h. The slurry was diluted with EtOAc (60 mL) and the organic layer was separated and washed with brine and dried with sodium sulfate. The solvent was removed under mild vacuum at room temperature (volatile compound) to give the desired aldehyde (1.87 g, 91%) which solidified as a light yellow crystal by standing at room temperature.

To a solution of the above aldehyde (1.6 g, 11.3 mmol) in 50 mL of MeOH (dry) was added TsOH.H₂O (363 mg, 0.17 eq) and (MeO)₃CH (5 mL). The reaction was heated up to reflux for 2 h then partitioned between EtOAc and water. The organic phase was then washed with NaHCO₃ solution and brine. The combined organics were dried over MgSO₄, filtered and concentrated in vacuo to give the desired 4-chloro-2-dimethoxymethyl-pyridine as a light yellow oil (1.83 g, 86%).

A sealed tube was charged with Pd(OAc)₂ (57.47 mg, 0.06 eq), K₃PO₄ (1.904 g, 2.0 eq), di-tert butyl phosphine biphenyl (152.7 mg, 0.12 eq) and 7-hydroxy-methylindole-2-carboxylic acid methyl ester (934.8 mg, 4.26 mmol) and toluene (20 mL), and capped with a septum. The system was degased and charged with argon, repeated for a couple of times. Then a solution of the 4-chloro-2-dimethoxymethyl-pyridine (800 mg, 4.26 mmol) from above in 4 mL of toluene was added via syringe. The mixture was heated at 100° C. with stirring under argon for 3 h. The reaction was cooled to room temperature, and the reaction mixture was filtered through a pad of diatomaceous earth and rinsed with methylene chloride. The combined filtrates were concentrated in vacuo. The crude products were purified by silica gel chromatography (30%-70% EtOAc/hex) to give the desired ether (790 mg, 50%) as a brown oil.

To a solution of the above ether (770 mg, 2.1 mmol) in THF/MeOH (25 mL/10 mL) was added LiOH.H₂O (218.1 mg, 2.50 eq) dissolved in 3 mL of water. The clear reaction solution was stirred at room temperature for 5 h, then concentrated in vacuo. The residual aqueous solution was diluted with water (15 mL), and extracted with ether. The organic layer was disgarded. The aqueous layer was acidified to pH 5 with 1.4 N HCl (~2.5 mL). A large amount of white precipitates were extracted with 200 mL of EtOAc and washed with brine. The combined organics were dried over MgSO₄, filtered and concentrated in vacuo to give the desired indole-2-carboxylic acid intermediate (644 mg, 90.5%) as a white foam.

To a soultion of the above carboxylic acid (651 mg, 1.9 mmol) in DMF (20 mL) were added HATU (723.2 mg, 1.0 eq) diisopropylethylamine (662.6 uL, 2.0 eq) and HOAt (129.4 mg, 0.5 eq). After 10 min, N-(3-amino-5-tert-butyl-2-methoxy-phenyl)-methanesulfonamide was added in one portion. After stirring at room temperature overnight, the reaction was worked up with EtOAc, washed with water and brine. The combined organics were dried over MgSO₄, filtered and concentrated in vacuo to give an oil which was purified by silica gel Chromatography (50% EtOAc/hexanes) to give the desired amide (1.03 g, 91%) as a white foam.

To a solution of the above amide (1.08 g, 1.81 mmol) in acetonitrile and water (20 mL/20 mL) was added CBr₄ (905 mg, 2.0 eq). The reaction was refluxed (oil bath temperature: 80° C.) overnight. The reaction was cooled to room temperature, adjusted to pH 7 with NaHCO₃ solution, extracted with EtOAc until no desired product was left in the aqueous layer. The combined organics were dried over MgSO₄, filtered and concentrated to give 1.5 g (>100%) of a light brown colored foam which was purified by silica gel chromatography (20%-70% EtOAc/hexanes) to provide the desired aldehyde intermediate as a yellow foam.

To a solution of the above aldehyde (80 mg, 0.145 mmol) in dichloroethane (10 mL) were added glacial HOAc (273 uL) and pyrrolidine (375 uL). The reaction was stirred at room temperature for 20 min. The reaction solution became cloudy. Triacetoxyborohydride (245 mg) was added to the reaction mixture. The reaction was stirred at room temperature for 1 h, then NaHCO₃ (saturated solution) was added, the mixture stirred for 10 min, then extracted with methylene chloride. The combined organics were washed with brine, dried over MgSO₄, filtered and concentrated down to give 85 mg of foam which was >97% pure by HPLC and 1HNMR. The foam was further purified by silica gel chromatography (5%-8% MeOH/methylene chloride) to provide the title compound (75 mg, 85%).

Example 16

Synthesis of 1-methyl-7-(pyridin-4-yloxy)-1H-indole-2-carboxylic acid (5-tert-butyl-3-{[(2-dimethylamino-ethyl)-methyl-amino]-methyl}-2-methoxyphenyl)-amide

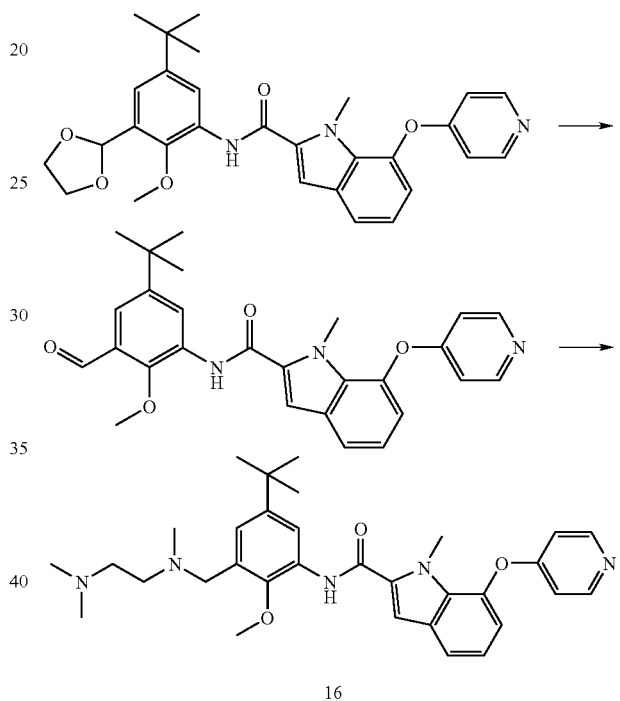

16

To a solution of 1-methyl-7-(pyridin-4-yloxy)-1H-indole-2-carboxylic acid (5-tert-butyl-3-[1,3]dioxolan-2-yl-2-methoxy-phenyl)-amide (0.20 g, 0.40 mmol) in THF (3.00 mL) was added 2.0 N HCl (2 mL). The solution was allowed to stir at room temperature and under an ambient atmosphere for 17.5 h. The solution was diluted in EtOAc (20 mL) and transferred to a separatory funnel. The aqueous layer was separated and the organic layer was washed with saturated NaHCO₃ solution (2×10 mL), water (1×10 mL), brine (1×10 mL), dried over MgSO₄, filtered and the solvent was evaporated to give the desired aldehyde as a yellow foam (0.16 g, 90%).

To a solution of the above aldehyde (0.04 g, 0.09 mmol) in dichloroethane (2.00 mL) was added acetic acid (0.06 mL, 1.06 mmol) followed by the dropwise addition of N,N,N'-trimethylethylenediamine (0.28 mL, 2.18 mmol) at 0° C. The solution was allowed to warm to room temperature and was stirred for 30 min., followed by the batchwise addition of sodium triacetoxyborohydride (0.05 g, 0.22 mmol). The reaction was allowed to stir for 17.5 h under an ambient atmosphere and at room temperature. The solution was diluted with EtOAc (10 mL) and quenched with 3% NH$_4$OH (1 mL). The biphasic system was transferred to a separatory funnel and the aqueous layer was separated. The organic layer was washed with 3% NH$_4$OH (2×2.0 mL), water (2×10 mL), brine (2×10 mL), dried over MgSO$_4$, filtered and the solvent was evaporated. The resulting residue was dissolved in CH$_2$Cl$_2$ and flash chromatographed (7% MeOH/CH$_2$Cl$_2$, 0.5% NH$_4$OH) to give the crude product as a yellow oil. The material was again flash chromatographed (8% MeOH/CH$_2$Cl$_2$, 0.5% NH$_4$OH) to give the title compound as a colorless foam (0.02 g, 41%).

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anticoagulant or fibrinolytic therapy (and the diseases or conditions related to such therapy) as described in U.S. application Ser. No. 10/630,599 and PCT/US03/23841.

The compounds of the invention are also p38 MAP kinase inhibitors. Methods for screening p38 MAP kinase inhibitors are known in the art. As disclosed in the Background of the Invention, the compounds of the invention will therefore be useful for treating oncological diseases. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822,PCT/US 01/21860 and U.S. application Ser. No. 10/214,782,each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to U.S. application Ser. No. 10/313,667. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Biological Assays

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2\times10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630,from *E. coli* serotype 0111.B4; stored as 1 mg/ml stock in endotoxin screened distilled $H_2O$ at −80° C.). Blanks (unstimulated) received $H_2O$ vehicle; final incubation volume was 250 μl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

Preferred compounds have an $IC_{50}<1$ uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

All publications, patent publications and patent applications cited in this application are incorporated herein by reference in their entirety.

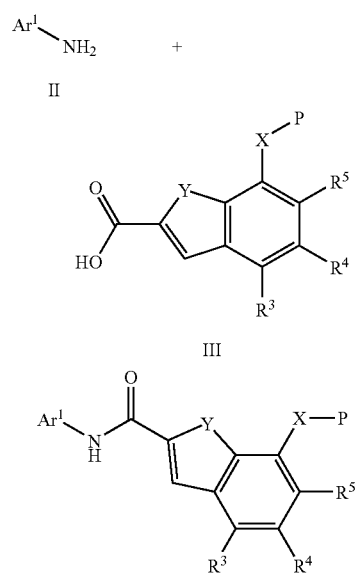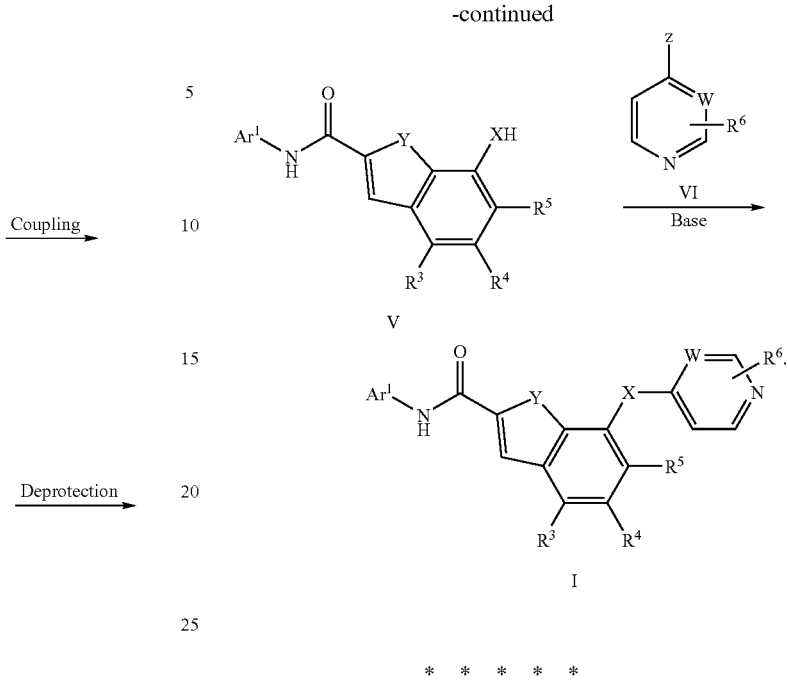

What is claimed is:
1. A compound of the formula (I)

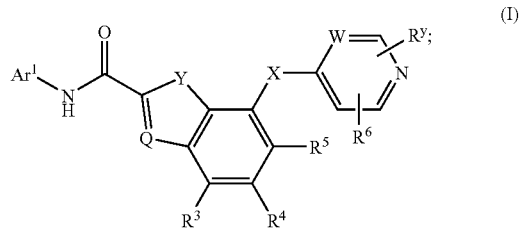

wherein:
Ar$^1$ is an aromatic carbocycle substituted with one R$^1$, and wherein Ar$^1$ is independently substituted with two R$^2$ groups and wherein one R$^1$ and one R$^2$ on adjacent ring atoms optionally form a 5- or 6-membered carbocyclic or heterocyclic ring;
R$^1$ is halogen, NO$_2$, NH$_2$, J-N(R$^a$)—(CH$_2$)$_m$—, N(J)$_2$—(CH$_2$)$_m$—, NH$_2$C(O)—, J-N(R$^a$)—C(O)—, J-S(O)$_m$—N(R$^a$)—, J-N(R$^a$)—S(O)$_m$— or heterocycle-(CH$_2$)$_m$— wherein the heterocyclic group is optionally substituted by C$_{1-5}$ alkyl;
Q is a N or CR$^p$;
Y is >CR$^p$R$^v$, —CR$^p$=C(R$^v$)—, —O—, —N(R$^x$)— or >S(O)$_m$;
wherein R$^a$, R$^p$, R$^v$, R$^x$ and R$^y$ are each independently hydrogen or C$_{1-5}$ alkyl;
X is —CH$_2$— or —O—;
W is N or CH;
each m is independently 0,1 or 2;

J is chosen from C1-10 alkyl and carbocycle each optionally substituted by $R^b$;

$R^2$ is chosen from C1-6 alkyl, C3-7 cycloalkyl optionally substituted by C1-5 alkyl, C1-4 acyl, aroyl, C1-4 alkoxy, each being optionally partially or fully halogenated, halogen, C1-6 alkoxycarbonyl, carbocyclesulfonyl and —SO$_2$—CF$_3$;

each $R^3$, $R^4$ and $R^5$ are independently chosen from hydrogen, C1-6 alkyl and halogen;

$R^6$ is optionally attached at a position ortho or meta to the N atom of the indicated ring, and is chosen from a bond, —O—, —O—(CH$_2$)$_{1-5}$—, >C(O), —NH—, —C(O)—NH—, —S—, C$_{1-5}$ alkyl branched or unbranched, C$_{2-5}$ alkenyl, C$_{1-3}$ acyl, C$_{1-3}$ alkyl(OH), heterocycle selected from morpholinyl, piperazinyl, piperidinyl, pyrrolidinyl and tetrahydrofuranyl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl and isothiazolyl or aryl each alkyl, alkenyl, acyl, heterocycle, heteroaryl and aryl are optionally substituted by one to three hydroxy, oxo, C$_{1-3}$ alkyl, C$_{1-3}$ alkoxy, C$_{1-5}$ alkoxycarbonyl, —NR$_7$R$_8$ or NR$_7$R$_8$—C(O)—;

wherein each $R_6$ is further optionally covalently attached to groups chosen from:
  hydrogen, —NR$_7$R$_8$, C$_{1-3}$ alkyl, C$_{3-6}$ cycloalkylC$_{0-2}$ alkyl, hydroxy, C$_{1-3}$ alkoxy, phenoxy, benzyloxy, arylC$_{0-4}$ alkyl, heteroaryl C$_{0-4}$ alkyl and heterocycle C$_{0-4}$alkyl, each above-listed heterocycle, heteroaryl and aryl group is optionally substituted by one to three hydroxy, oxo, C$_{1-4}$ alkyl, C$_{1-3}$ alkoxy, C$_{1-5}$ alkoxycarbonyl, NR$_7$R$_8$—C(O)— or C$_{1-4}$ acyl;

each $R_7$ and $R_8$ are independently hydrogen, phenylC$_{0-3}$ alkyl optionally subtituted by halogen, C$_{1-3}$ alkyl or diC$_{1-5}$ alkyl amino, or $R_7$ and $R_8$ are C$_{1-2}$ acyl, benzoyl or C$_{1-5}$ branched or unbranched alkyl optionally substituted by C$_{1-4}$ alkoxy, hydroxy or mono or diC$_{1-3}$ alkyl amino; and $R^b$ is chosen from hydrogen, C1-5 alkyl, hydroxyC1-5 alkyl, C2-5 alkenyl, C2-5 alkynyl, carbocycle, heterocycle, heteroaryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, or $R^b$ is chosen from C1-5 alkylsulphonylamino, hydroxy, oxo, halogen, nitro and nitrile;

or the pharmaceutically acceptable salts or acids thereof.

2. The compound according to claim 1 and wherein:
Y is —O—, —S—, —NH—, —N(CH$_2$CH$_3$)— or —N(CH$_3$)—;
X is —O—;
Q is CH;
J is chosen from C1-10 alkyl, aryl or C3-7 cycloalkyl each optionally substituted by $R^b$;
$R_2$ is independently chosen from C1-6 alkyl, C3-6 cycloalkyl optionally substituted by C1-3 alkyl, acetyl, aroyl, C1-5 alkoxy, each being optionally partially or fully halogenated, halogen, methoxycarbonyl, phenylsulfonyl and —SO$_2$—CF$_3$;
each $R^3$, $R^4$ and $R^5$ are hydrogen;
$R^b$ is chosen from hydrogen, C1-5 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, C1-5 sulphonylamino, hydroxy, halogen, trifluoromethyl, nitro, nitrile or $R^b$ is chosen from; heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone and heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

3. The compound according to claim 2 and wherein:
$Ar^1$ is chosen from phenyl, naphthyl, tetrahydronaphthyl, indanyl and indenyl, each $Ar^1$ is optionally substituted with one $R^1$, and independently substituted with two $R^2$ groups;
Y is —O—, —S— or —N(CH$_3$)—;
$R^6$ is present, and is chosen from a bond, —O—, —O—(CH$_2$)$_{1-5}$—, —NH—, —C(O)—NH—, C$_{1-5}$ alkyl branched or unbranched, C$_{2-5}$ alkenyl, C$_{1-3}$ alkyl(OH), heterocycle selected from morpholinyl, piperazinyl, piperidinyl, pyrrolidinyl and tetrahydrofuranyl, or aryl chosen from phenyl and naphthyl, each alkyl, alkenyl, heterocycle and aryl are optionally substituted by one to three hydroxy, C$_{1-3}$ alkyl, C$_{1-3}$ alkoxy, mono or diC$_{1-3}$ alkyl amino, amino or C$_{1-5}$ alkoxycarbonyl;
wherein each $R_6$ is further optionally covalently attached to groups chosen from: hydrogen, —NR$_7$R$_8$, C$_{1-3}$ alkyl, C$_{3-6}$ cycloalkylC$_{0-2}$alkyl, hydroxy, C$_{1-3}$ alkoxy, phenoxy, benzyloxy, phenylC$_{0-4}$ alkyl, piperazinylC$_{0-4}$ alkyl, piperidinyl C$_{0-4}$alkyl, pyrrolidinylC$_{0-4}$ alkyl, morpholinylC$_{0-4}$ alkyl, tetrahydrofuranylC$_{0-4}$ alkyl, triazolyl C$_{0-4}$alkyl, imidazolyl C$_{0-4}$alkyl and pyridinyl C$_{0-4}$alkyl, each abovelisted heterocycle, heteroaryl and phenyl group is optionally substituted by one to three hydroxy, oxo, C$_{1-4}$ alkyl, C$_{1-3}$ alkoxy, C$_{1-5}$ alkoxycarbonyl, —NR$_7$R$_8$, NR$_7$R$_8$—C(O)— or C$_{1-4}$ acyl;
each $R_7$ and $R_8$ are independently hydrogen, phenylC$_{0-3}$ alkyl optionally subtituted by halogen, C$_{1-3}$ alkyl or diC$_{1-5}$ alkyl amino, or $R_7$ and $R_8$ are C$_{1-2}$ acyl, benzoyl or C$_{1-5}$ branched or unbranched alkyl optionally substituted by C$_{1-4}$ alkoxy, hydroxy or mono or diC$_{1-3}$ alkyl amino.

4. The compound according to claim 3 and wherein:
Y is —N(CH$_3$)—;
J is C1-10 alkyl optionally substituted by $R^b$;
$R_2$ is independently chosen from C1-6 alkyl, C3-6 cycloalkyl optionally substituted by C1-3 alkyl and C1-5 alkoxy, each being optionally be partially or fully halogenated;
$R^6$ is chosen from a bond, —O—, —O—(CH$_2$)$_{1-5}$—, —NH—, —C(O)—NH—, C$_{1-5}$ alkyl branched or unbranched, C$_{2-5}$ alkenyl, C$_{1-3}$ alkyl(OH), heterocycle selected from morpholinyl, piperazinyl, piperidinyl and pyrrolidinyl or phenyl, each alkyl, alkenyl, heterocycle and phenyl are optionally substituted by one to three hydroxy, C$_{1-3}$ alkyl, C$_{1-3}$ alkoxy, mono or diC$_{1-3}$ alkyl amino, amino or C$_{1-5}$ alkoxycarbonyl;

wherein each $R_6$ is further optionally covalently attached to groups chosen from:

hydrogen, —$NR_7R_8$, $C_{1-3}$ alkyl, $C_{3-6}$ cycloalkyl$C_{0-2}$ alkyl, benzyloxy, phenyl$C_{0-4}$ alkyl, piperazinyl$C_{0-4}$ alkyl, piperidinyl $C_{0-4}$alkyl, pyrrolidinyl$C_{0-4}$ alkyl, morpholinyl$C_{0-4}$ alkyl, triazolyl $C_{0-4}$alkyl, imidazolyl $C_{0-4}$alkyl and pyridinyl $C_{0-4}$alkyl, each above-listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, amino, $NR_7R_8$—C(O)— or $C_{1-4}$ acyl;

each $R_7$ and $R_8$ are independently hydrogen, phenyl$C_{0-2}$ alkyl optionally subtituted by halogen, $C_{1-3}$ alkyl or di$C_{1-5}$ alkyl amino, or $R_7$ and $R_8$ are $C_{1-5}$ branched or unbranched alkyl optionally substituted by $C_{1-4}$ alkoxy, hydroxy or mono or di$C_{1-3}$ alkyl amino;

$R^b$ is chosen from hydrogen, C1-5 alkyl, C3-7 cycloalkyl$C_{0-2}$ alkyl, aryl, C1-5 alkoxy, amino, C1-5 alkylamino, C1-3 dialkylamino, C1-3 acyl, C1-5 alkoxycarbonyl, C1-3 acyloxy, C1-3 acylamino, C1-3 sulphonylamino, hydroxy, halogen, trifluoromethyl, nitro, nitrile; or $R^b$ is chosen from pyrrolidinyl, pyrrolinyl, morpholinyl, thiomorpholinyl, thiomorpholinyl sulfoxide, thiomorpholinyl sulfone, piperidinyl, piperazinyl, piperidinonyl, tetrahydropyrimidonyl, aziridinyl, isoxazolyl, oxazolyl, thiazolyl, thiadiazolyl, tetrazolyl, pyrazolyl, pyrrolyl, imidazolyl, pyridinyl, pyrimidinyl, pyrazinyl and pyridazinyl.

5. The compound according to claim 4 and wherein:
$Ar^1$ is formula (A) or (B)

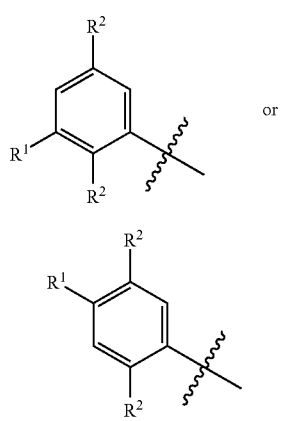

wherein:
when $Ar^1$ is formula (A) then:
$R^1$ is $NH_2$, J-N($R^a$)—($CH_2$)$_m$—, $NH_2C(O)$—, J-N($R^a$)—C(O)—, J-S(O)$_2$—N($R^a$)—, J-N($R^a$)—S(O)$_2$— or heterocycle-($CH_2$)$_{1-2}$— wherein the heterocycle is chosen from pyrrolidinyl, morpholinyl and piperazinyl each optionally substituted by C1-4 alkyl, and
J is $C_{1-5}$ alkyl optionally substituted by $R^b$;
or
when $Ar^1$ is formula (B) then:
$R^1$ is hydrogen or halogen;
$R_2$ is independently chosen from C1-5 alkyl, C3-6 cycloalkyl optionally substituted by C1-3 alkyl and C1-5 alkoxy, each being optionally partially or fully halogenated;

$R^6$ is chosen from
a bond, —O—, —O—($CH_2$)$_{1-5}$—, —NH—, —C(O)—NH—, $C_{1-5}$ alkyl branched or unbranched, $C_{2-5}$ alkenyl, $C_{1-3}$ alkyl(OH), heterocycle selected from morpholinyl, piperazinyl, piperidinyl and pyrrolidinyl or phenyl, each alkyl, alkenyl, heterocycle and phenyl are optionally substituted by one to three hydroxy, $C_{1-3}$ alkyl, $C_{1-3}$ alkoxy, mono or di$C_{1-3}$ alkyl amino, amino or $C_{1-5}$ alkoxycarbonyl;

wherein each $R_6$ is further optionally covalently attached to groups chosen from:

hydrogen, —$NR_7R_8$, $C_{1-3}$ alkyl, $C_{3-6}$ cycloalkyl$C_{0-2}$ alkyl, benzyloxy, phenyl$C_{0-4}$ alkyl, piperazinyl, piperazinyl$C_{1-2}$ alkyl, piperidinyl, piperidinyl $C_{1-2}$alkyl, pyrrolidinyl, pyrrolidinyl $C_{1-2}$ alkyl, morpholinyl, morpholinyl$C_{1-2}$ alkyl, triazolyl, triazolyl $C_{1-2}$alkyl, imidazolyl, imidazolyl $C_{1-2}$alkyl, pyridinyl and pyridinyl $C_{1-2}$alkyl, each above-listed heterocycle, heteroaryl and phenyl group is optionally substituted by one to three hydroxy, oxo, $C_{1-4}$ alkyl, $C_{1-3}$ alkoxy, $C_{1-5}$ alkoxycarbonyl, amino, $NR_7R_8$—C(O)— or $C_{1-4}$ acyl.

6. The compound according to claim 5 and wherein:
$Ar^1$ is formula (A) or (B)

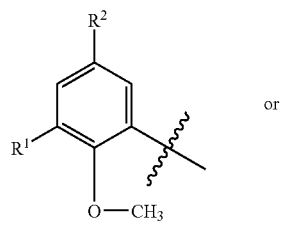

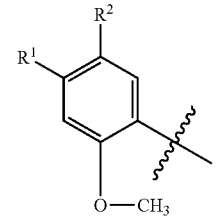

and $R^2$ is chosen from

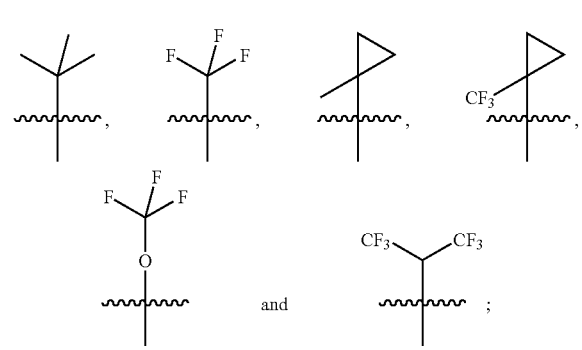

when $Ar^1$ is formula (A) then:
when $R^1$ is J-S(O)$_2$—N($R^a$)— or J-N($R^a$)—S(O)$_2$— then J is $C_{1-3}$ alkyl; and when R¹ is NH₂, J-N(Rᵃ)—(CH₂)ₘ—, NH₂C(O)—, J-N(Rᵃ)—C(O)—,
or heterocycle-(CH₂)₁₋₂— wherein the heterocycle is chosen from pyrrolidinyl, morpholinyl, piperazinyl or C1-4alkylpiperazinyl, then J is C1-3 alkyl optionally substituted by Rᵇ.

7. The compound according to claim 6 and wherein:
Rᵇ is chosen from hydrogen, C1-5 alkyl, C3-6 cycloalkylC0-2 alkyl, phenyl, C1-5 alkoxy, amino, C1-5 alkylamino, C1-3 dialkylamino, C1-3 acyl, C1-5 alkoxycarbonyl, C1-3 acyloxy, C1-3 acylamino, hydroxy, halogen;
or Rᵇ is chosen from morpholinyl, thiomorpholinyl, thiomorpholinyl sulfoxide, thiomorpholinyl sulfone, piperidinyl, piperidinonyl, pyridinyl, pyrimidinyl, pyrazinyl and pyridazinyl.

8. The compound according to claim 7 and wherein:
Rᵇ is chosen from amino, C1-5 alkylamino, C1-3 dialkylamino;
or Rᵇ is chosen morpholinyl, piperidinyl and pyridinyl.

9. The compound according to claim 6 and wherein:
Ar¹ is formula (A).

10. The compound according to claim 6 and wherein:
Ar¹ is formula (B).

11. The compound according to claim 6 and wherein:
Ar¹ is

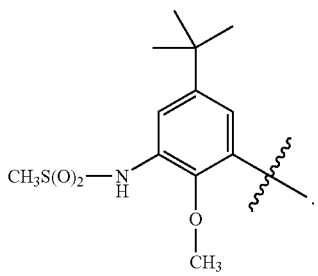

12. A compound chosen from:
1-Methyl-7-(pyrimidin-4-yloxy)-1H-indole-2-carboxylic acid (5-tert-butyl-3-methanesulfonylamino-2-methoxy-phenyl)-amide
7-(2-Methylamino-pyrimidin-4-yloxy)-1H-indole-2-carboxylic acid (5-tert-butyl-3-methanesulfonylamino-2-methoxy-phenyl)-amide
1-Methyl-7-(2-methylamino-pyrimidin-4-yloxy)-1H-indole-2-carboxylic acid (5-tert-butyl-3-methanesulfonylamino-2-methoxy-phenyl)-amide
1-Methyl-7-(2-methylamino-pyrimidin-4-yloxy)-1H-indole-2-carboxylic acid (5-tert-butyl-2-methoxy-phenyl)-amide
7-[2-(2-Dimethylamino-ethylamino)-pyrimidin-4-yloxy]-1-methyl-1H-indole-2-carboxylic acid (5-tert-butyl-3-methanesulfonylamino-2-methoxy-phenyl)-amide
7-(2-Cyclopropylamino-pyrimidin-4-yloxy)-1-methyl-1H-indole-2-carboxylic acid (5-tert-butyl-3-methanesulfonylamino-2-methoxy-phenyl)-amide
7-[2-(4-Methoxy-benzylamino)-pyrimidin-4-yloxy]-1-methyl-1H-indole-2-carboxylic acid (5-tert-butyl-3-methanesulfonylamino-2-methoxy-phenyl)-amide
1-Methyl-7-[2-(4-methyl-piperazin-1-yl)-pyrimidin-4-yloxy]-1H-indole-2-carboxylic acid (5-tert-butyl-3-methanesulfonylamino-2-methoxy-phenyl)-amide
7-[2-(2-Dimethylamino-ethylamino)-pyrimidin-4-yloxy]-1-methyl-1H-indole-2-carboxylic acid (5-tert-butyl-2-methoxy-phenyl)-amide
1-Methyl-7-[2-(4-methyl-piperazin-1-yl)-pyrimidin-4-yloxy]-1H-indole-2-carboxylic acid (5-tert-butyl-2-methoxy-phenyl)-amide
1-Methyl-7-[2-(2-morpholin-4-yl-ethylamino)-pyrimidin-4-yloxy]-1H-indole-2-carboxylic acid (5-tert-butyl-3-methanesulfonylamino-2-methoxy-phenyl)-amide
7-[2-(3-Dimethylamino-propylamino)-pyrimidin-4-yloxy]-1-methyl-1H-indole-2-carboxylic acid (5-tert-butyl-3-methanesulfonylamino-2-methoxy-phenyl)-amide
7-[2-(3-Dimethylamino-2,2-dimethyl-propylamino)-pyrimidin-4-yloxy]-1-methyl-1H-indole-2-carboxylic acid (5-tert-butyl-3-methanesulfonylamino-2-7-(2-Dimethylamino-pyrimidin-4-yloxy)-1-methyl-1H-indole-2-carboxylic acid (5-tert-butyl-3-methanesulfonylamino-2-methoxy-phenyl)-amide
1-Methyl-7-(6-methyl-2-methylamino-pyrimidin-4-yloxy)-1H-indole-2-carboxylic acid (5-tert-butyl-3-methanesulfonylamino-2-methoxy-phenyl)-amide
1-Methyl-7-[2-(2-pyrrolidin-1-yl-ethylamino)-pyrimidin-4-yloxy]-1H-indole-2-carboxylic acid (5-tert-butyl-3-methanesulfonylamino-2-methoxy-phenyl)-amide
1-Methyl-7-[2-(piperidin-4-ylamino)-pyrimidin-4-yloxy]-1H-indole-2-carboxylic acid (5-tert-butyl-3-methanesulfonylamino-2-methoxy-phenyl)-amide
4-{4-[2-(5-tert-Butyl-3-methanesulfonylamino-2-methoxy-phenylcarbamoyl)-1-methyl-1H-indol-7-yloxy]-pyrimidin-2-ylamino}-piperidine-1-carboxylic acid
7-{2-[(2-Dimethylamino-ethyl)-methyl-amino]-pyrimidin-4-yloxy}-1-methyl-1H-indole-2-carboxylic acid (5-tert-butyl-3-methanesulfonylamino-2-methoxy-1-Methyl-7-[6-methyl-2-(4-methyl-piperazin-1-yl)-pyrimidin-4-yloxy]-1H-indole-2-carboxylic acid (5-tert-butyl-3-methanesulfonylamino-2-methoxy-7-[2-(2-Dimethylamino-ethoxy)-pyrimidin-4-yloxy]-1-methyl-1H-indole-2-carboxylic acid (5-tert-butyl-3-methanesulfonylamino-2-methoxy-phenyl)-amide
7-[2-(2-Dimethylamino-ethoxy)-pyrimidin-4-yloxy]-1-methyl-1H-indole-2-carboxylic acid (5-tert-butyl-2-methoxy-phenyl)-amide
1-Methyl-7-[2-(2-pyrrolidin-1-yl-ethoxy)-pyrimidin-4-yloxy]-1H-indole-2-carboxylic acid (5-tert-butyl-3-methanesulfonylamino-2-methoxy-phenyl)-amide
1-Methyl-7-[2-(2-morpholin-4-yl-ethoxy)-pyrimidin-4-yloxy]-1H-indole-2-carboxylic acid (5-tert-butyl-3-methanesulfonylamino-2-methoxy-phenyl)-amide
1-Methyl-7-[2-(1-methyl-piperidin-4-yloxy)-pyrimidin-4-yloxy]-1H-indole-2-carboxylic acid (5-tert-butyl-3-methanesulfonylamino-2-methoxy-phenyl)-amide
7-[2-(2-Dimethylamino-ethoxy)-6-methyl-pyrimidin-4-yloxy]-1-methyl-1H-indole-2-carboxylic acid (5-tert-butyl-3-methanesulfonylamino-2-methoxy-1-Methyl-7-(2-methylcarbamoyl-pyridin-4-yloxy)-1H-indole-2-carboxylic acid[5-tert-butyl-3-(2-dimethylamino-ethylcarbamoyl)-2-methoxy-phenyl]-amide
7-[2-(2-Dimethylamino-ethylcarbamoyl)-pyridin-4-yloxy]-1-methyl-1H-indole-2-carboxylic acid (5-tert-butyl-3-methanesulfonylamino-2-methoxy-phenyl)-amide 1-Methyl-7-(2-methylamino-pyrimidin-4-yloxy)-1H-indole-2-carboxylic acid[5-tert-butyl-3-(2-dimethylamino-ethylcarbamoyl)-2-methoxy-phenyl]-amide
1-Methyl-7-(2-methylamino-pyrimidin-4-yloxy)-1H-indole-2-carboxylic acid[5-tert-butyl-2-methoxy-3-(2-morpholin-4-yl-ethylcarbamoyl)-phenyl]-amide
1-Methyl-7-(2-methylamino-pyrimidin-4-yloxy)-1H-indole-2-carboxylic acid (5-tert-butyl-3-carbamoyl-2-methoxy-phenyl)-amide
1-Methyl-7-(2-methylamino-pyrimidin-4-yloxy)-1H-indole-2-carboxylic acid (5-tert-butyl-2-methoxy-3-methylcarbamoyl-phenyl)-amide
1-Methyl-7-(2-vinyl-pyrimidin-4-yloxy)-1H-indole-2-carboxylic acid (5-tert-butyl-3-methanesulfonylamino-2-methoxy-phenyl)-amide
7-[2-(1,2-Dihydroxy-ethyl)-pyrimidin-4-yloxy]-1-methyl-1H-indole-2-carboxylic acid (5-tert-butyl-3-methanesulfonylamino-2-methoxy-phenyl)-amide
1-Methyl-7-[2-(morpholin-4-ylamino)-pyrimidin-4-yloxy]-1H-indole-2-carboxylic acid (5-tert-butyl-3-methanesulfonylamino-2-methoxy-phenyl)-amide
1-Methyl-7-(2-morpholin-4-ylmethyl-pyrimidin-4-yloxy)-1H-indole-2-carboxylic acid (5-tert-butyl-3-methanesulfonylamino-2-methoxy-phenyl)-amide
1-Methyl-7-(2-morpholin-4-ylmethyl-pyridin-4-yloxy)-1H-indole-2-carboxylic acid (5-tert-butyl-3-methanesulfonylamino-2-methoxy-phenyl)-amide
1-Methyl-7-[2-(4-methyl-piperazin-1-ylmethyl)-pyrimidin-4-yloxy]-1H-indole-2-carboxylic acid (5-tert-butyl-3-methanesulfonylamino-2-methoxy-phenyl)-amide
7-(2-Dimethylaminomethyl-pyridin-4-yloxy)-1-methyl-1H-indole-2-carboxylic acid (5-tert-butyl-3-methanesulfonylamino-2-methoxy-phenyl)-amide
1-Methyl-7-(2-methylcarbamoyl-pyridin-4-yloxy)-1H-indole-2-carboxylic acid (5-tert-butyl-3-methanesulfonylamino-2-methoxy-phenyl)-amide
7-(2-Benzyloxymethyl-pyridin-4-yloxy)-1-methyl-1H-indole-2-carboxylic acid (5-tert-butyl-3-methanesulfonylamino-2-methoxy-phenyl)-amide
1-Methyl-7-(2-methylamino-pyrimidin-4-yloxy)-1H-indole-2-carboxylic acid (5-tert-butyl-2-methoxy-3-morpholin-4-ylmethyl-phenyl)-amide
1-Methyl-7-(2-methylamino-pyrimidin-4-yloxy)-1H-indole-2-carboxylic acid[5-tert-butyl-2-methoxy-3-(4-methyl-piperazin-1-ylmethyl)-phenyl]-amide
1-Methyl-7-(2-methylamino-pyrimidin-4-yloxy)-1H-indole-2-carboxylic acid (5-tert-butyl-3-dimethylaminomethyl-2-methoxy-phenyl)-amide
1-Methyl-7-(2-methylamino-pyrimidin-4-yloxy)-1H-indole-2-carboxylic acid (3-amino-5-tert-butyl-2-methoxy-phenyl)-amide
1-Methyl-7-(2-methylamino-pyrimidin-4-yloxy)-1H-indole-2-carboxylic acid (5-tert-butyl-3-dibenzylamino-2-methoxy-phenyl)-amide
1-Methyl-7-(2-methylamino-pyrimidin-4-yloxy)-1H-indole-2-carboxylic acid (5-tert-butyl-2-methoxy-3-methylsulfamoyl-phenyl)-amide
7-[2-(2-Dimethylamino-ethylamino)-pyrimidin-4-yloxy]-1-methyl-1H-indole-2-carboxylic acid (5-tert-butyl-3-[1,3]dioxolan-2-yl-2-methoxy-phenyl)-amide
1-Methyl-7-[2-(4-methyl-piperazin-1-yl)-pyrimidin-4-yloxy]-1H-indole-2-carboxylic acid (5-tert-butyl-2-methoxy-3-methylaminomethyl-phenyl)-amide
1-Methyl-7-[2-(4-methyl-piperazin-1-yl)-pyrimidin-4-yloxy]-1H-indole-2-carboxylic acid (5-tert-butyl-2-methoxy-3-pyrrolidin-1-ylmethyl-phenyl)-amide
1-Methyl-7-{2-[methyl-(1-methyl-piperidin-4-yl)-amino]-pyrimidin-4-yloxy}-1H-indole-2-carboxylic acid (5-tert-butyl-3-methanesulfonylamino-2-methoxy-7-(2-Hydroxymethyl-pyridin-4-yloxy)-1-methyl-1H-indole-2-carboxylic acid (5-tert-butyl-3-methanesulfonylamino-2-methoxy-phenyl)-amide
1-Methyl-7-(2-methylamino-pyrimidin-4-yloxy)-1H-indole-2-carboxylic acid[5-tert-butyl-2-methoxy-3-(2-morpholin-4-yl-ethylamino)-phenyl]-amide
1-Methyl-7-(pyridin-4-yloxy)-1H-indole-2-carboxylic acid (5-tert-butyl-3-methanesulfonylamino-2-methoxy-phenyl)-amide
1-Methyl-7-(2-piperazin-1-yl-pyrimidin-4-yloxy)-1H-indole-2-carboxylic acid (5-tert-butyl-3-methanesulfonylamino-2-methoxy-phenyl)-amide
1-Methyl-7-(pyrimidin-4-yloxy)-1H-indole-2-carboxylic acid[3-methanesulfonylamino-2-methoxy-5-(1-methyl-cyclopropyl)-phenyl]-amide
1-Methyl-7-[2-(5-methyl-2,5-diaza-bicyclo[2.2.1]hept-2-yl)-pyrimidin-4-yloxy]-1H-indole-2-carboxylic acid (5-tert-butyl-3-methanesulfonylamino-2-methoxy-7-[2-(2,5-Diaza-bicyclo[2.2.1]hept-2-yl)-pyrimidin-4-yloxy]-1-methyl-1H-indole-2-carboxylic acid (5-tert-butyl-3-methanesulfonylamino-2-methoxy-7-(2-Methoxy-pyrimidin-4-yloxy)-1-methyl-1H-indole-2-carboxylic acid (5-tert-butyl-3-methanesulfonylamino-2-methoxy-phenyl)-amide
7-[2-(4-tert-Butyl-piperazin-1-yl)-pyrimidin-4-yloxy]-1-methyl-1H-indole-2-carboxylic acid (5-tert-butyl-3-methanesulfonylamino-2-methoxy-phenyl)-amide
1-Methyl-7-[2-(2-morpholin-4-yl-ethyl)-pyrimidin-4-yloxy]-1H-indole-2-carboxylic acid (5-tert-butyl-3-methanesulfonylamino-2-methoxy-phenyl)-amide
1-Methyl-7-{2-[2-(4-methyl-piperazin-1-yl)-ethyl]-pyrimidin-4-yloxy}-1H-indole-2-carboxylic acid (5-tert-butyl-3-methanesulfonylamino-2-methoxy-1-Methyl-7-[2-(2-pyrrolidin-1-yl-ethyl)-pyrimidin-4-yloxy]-1H-indole-2-carboxylic acid (5-tert-butyl-3-methanesulfonylamino-2-methoxy-phenyl)-amide
7-[2-(2-Dimethylamino-ethyl)-pyrimidin-4-yloxy]-1-methyl-1H-indole-2-carboxylic acid (5-tert-butyl-3-methanesulfonylamino-2-methoxy-phenyl)-amide
1-Methyl-7-[2-(2-morpholin-4-yl-ethyl)-pyrimidin-4-yloxy]-1H-indole-2-carboxylic acid (3-methanesulfonylamino-2-methoxy-5-trifluoromethyl-phenyl)-1-Methyl-7-[2-(4-methyl-piperazin-1-yl)-pyrimidin-4-yloxy]-1H-indole-2-carboxylic acid (3-methanesulfonylamino-2-methoxy-5-trifluoromethyl-phenyl)-7-{2-[2-(4-tert-Butyl-piperazin-1-yl)-ethyl]-pyrimidin-4-yloxy}-1-methyl-1H-indole-2-carboxylic acid (5-tert-butyl-3-methanesulfonylamino-2-methoxy-7-[2-(4-tert-Butyl-piperazin-1-ylmethyl)-pyrimidin-4-yloxy]-1-methyl-1H-indole-2-carboxylic acid (5-tert-butyl-3-methanesulfonylamino-2-methoxy-1-Methyl-7-(2-pyrrolidin-1-ylmethyl-pyrimidin-4-yloxy)-1H-indole-2-carboxylic acid (5-tert-butyl-3-methanesulfonylamino-2-methoxy-phenyl)-amide 7-(2,6-Dimethyl-pyridin-4-yloxy)-1-methyl-1H-indole-2-carboxylic acid (5-tert-butyl-3-methanesulfonylamino-2-methoxy-phenyl)-amide 7-(2-Ethyl-pyridin-4-yloxy)-1-methyl-1H-indole-2-carboxylic acid (5-tert-butyl-3-methanesulfonylamino-2-methoxy-phenyl)-amide 1-Methyl-7-[2-(1,2,3,6-tetrahydro-pyridin-4-yl)-pyrimidin-4-yloxy]-1H-indole-2-carboxylic acid (5-tert-butyl-3-methanesulfonylamino-2-methoxy-phenyl)-amide 7-(2-Amino-pyrimidin-4-yloxy)-1-methyl-1H-indole-2-carboxylic acid (5-tert-butyl-3-methanesulfonylamino-2-methoxy-phenyl)-amide 1-Methyl-7-(2-pyrrolidin-1-ylmethyl-pyridin-4-yloxy)-1H-indole-2-carboxylic acid (5-tert-butyl-3-methanesulfonylamino-2-methoxy-phenyl)-amide 1-Methyl-7-(2-piperidin-1-ylmethyl-pyridin-4-yloxy)-1H-indole-2-carboxylic acid (5-tert-butyl-3-methanesulfonylamino-2-methoxy-phenyl)-amide 1-Methyl-7-[2-(4-methyl-piperazin-1-ylmethyl)-pyridin-4-yloxy]-1H-indole-2-carboxylic acid (5-tert-butyl-3-methanesulfonylamino-2-methoxy-phenyl)-amide 1-Methyl-7-(pyridin-4-yloxy)-1H-indole-2-carboxylic acid (5-tert-butyl-3-{[(2-dimethylamino-ethyl)-methyl-amino]-methyl}-2-methoxy-phenyl)-amide 7-(2-{[(2-Dimethylamino-ethyl)-methyl-amino]-methyl}-pyrimidin-4-yloxy)-1-methyl-1H-indole-2-carboxylic acid (5-tert-butyl-3-methanesulfonylamino-2-1-Methyl-7-[2-(4-methyl-piperazin-1-yl)-pyrimidin-4-yloxy]-1H-indole-2-carboxylic acid (5-tert-butyl-3-carbamoyl-2-methoxy-phenyl)-amide 1-Methyl-7-[2-((1S,4S)-5-methyl-2,5-diaza-bicyclo[2.2.1]hept-2-yl)-pyridin-4-yloxy]-1H-indole-2-carboxylic acid (5-tert-butyl-3-methanesulfonylamino-2-1-Methyl-7-[2-(4-methyl-[1,4]diazepan-1-yl)-pyridin-4-yloxy]-1H-indole-2-carboxylic acid (5-tert-butyl-3-methanesulfonylamino-2-methoxy-phenyl)-amide 7-(2-[1,4]Diazepan-1-yl-pyridin-4-yloxy)-1-methyl-1-H-indole-2-carboxylic acid (5-tert-butyl-3-methanesulfonylamino-2-methoxy-phenyl)-amide 1-Methyl-7-(2-piperazin-1-yl-pyridin-4-yloxy)-1H-indole-2-carboxylic acid (5-tert-butyl-3-methanesulfonylamino-2-methoxy-phenyl)-amide 1-trideuterio-7-(2-piperazin-1-yl-pyridin-4-yloxy)-1H-indole-2-carboxylic acid (5-tert-butyl-3-methanesulfonylamino-2-methoxy-phenyl)-amide 7-[2-(Hexahydro-pyrrolo[1,2-a]pyrazin-2-yl)-pyridin-4-yloxy]-1-methyl-1H-indole-2-carboxylic acid (5-tert-butyl-3-methanesulfonylamino-2-methoxy-1-trideuterio-7-[2-(4-methyl-piperazin-1-yl)-pyridin-4-yloxy]-1H-indole-2-carboxylic acid[3-methanesulfonylamino-2-methoxy-5-(1-methyl-cyclopropyl)-7-[2-((S)-3-Dimethylamino-pyrrolidin-1-yl)-pyridin-4-yloxy]-1-methyl-1H-indole-2-carboxylic acid[3-methanesulfonylamino-2-methoxy-5-(1-methyl-7-[2-((S)-3-Dimethylamino-pyrrolidin-1-yl)-pyridin-4-yloxy]-1-methyl-1H-indole-2-carboxylic acid[3-methanesulfonylamino-2-methoxy-5-(1-methyl-1-Methyl-7-[2-(4-methyl-piperazine-1-carbonyl)-pyridin-4-yloxy]-1H-indole-2-carboxylic acid (5-tert-butyl-3-methanesulfonylamino-2-methoxy-phenyl)-amide 1-Methyl-7-[2-(piperazine-1-carbonyl)-pyridin-4-yloxy]-1H-indole-2-carboxylic acid (5-tert-butyl-3-methanesulfonylamino-2-methoxy-phenyl)-amide or the pharmaceutically acceptable salts or acids thereof.

13. A compound chosen from:

7-(Pyrimidin-4-yloxy)-benzo[b]thiophene-2-carboxylic acid (5-tert-butyl-3-methanesulfonylamino-2-methoxy-phenyl)-amide 7-(Pyrimidin-4-yloxy)-1H-indole-2-carboxylic acid (5-tert-butyl-3-methanesulfonylamino-2-methoxy-phenyl)-amide 7-(Pyrimidin-4-yloxy)-benzofuran-2-carboxylic acid (5-tert-butyl-3-methanesulfonylamino-2-methoxy-phenyl)-amide 1-Methyl-7-(pyridin-3-yloxy)-1H-indole-2-carboxylic acid (5-tert-butyl-3-methanesulfonylamino-2-methoxy-phenyl)-amide 7-(2-Benzylamino-pyrimidin-4-yloxy)-1-methyl-1H-indole-2-carboxylic acid (5-tert-butyl-3-methanesulfonylamino-2-methoxy-phenyl)-amide 1-Methyl-7-{2-[(pyridin-2-ylmethyl)-amino]-pyrimidin-4-yloxy}-1H-indole-2-carboxylic acid (5-tert-butyl-3-methanesulfonylamino-2-methoxy-phenyl)-amide 7-[2-(2-Imidazol-1-yl-ethylamino)-pyrimidin-4-yloxy]-1-methyl-1H-indole-2-carboxylic acid (5-tert-butyl-3-methanesulfonylamino-2-methoxy-phenyl)-amide 1-Methyl-7-[2-(2-[1,2,3]triazol-1-yl-ethylamino)-pyrimidin-4-yloxy]-1H-indole-2-carboxylic acid (5-tert-butyl-3-methanesulfonylamino-2-methoxy-phenyl)-7-[2-(3-Dimethylamino-propylamino)-pyrimidin-4-yloxy]-1-methyl-1H-indole-2-carboxylic acid[2-methoxy-5-(2,2,2-trifluoro-1-trifluoromethyl-ethyl)-phenyl]-7-{2-[(2-Dimethylamino-ethyl)-methyl-amino]-pyrimidin-4-yloxy}-1-methyl-1H-indole-2-carboxylic acid (4-chloro-2-methoxy-5-trifluoromethyl-phenyl)-7-[2-(4-Acetyl-piperazin-1-yl)-pyrimidin-4-yloxy]-1-methyl-1H-indole-2-carboxylic acid (5-tert-butyl-3-methanesulfonylamino-2-methoxy-phenyl)-amide 1-Methyl-7-[2-(4-methyl-piperazin-1-yl)-pyrimidin-4-yloxy]-1H-indole-2-carboxylic acid (4-chloro-2-methoxy-5-trifluoromethyl-phenyl)-amide 7-[2-(2-Dimethylamino-ethylamino)-pyrimidin-4-yloxy]-1-methyl-1H-indole-2-carboxylic acid (2-methoxy-5-trifluoromethoxy-phenyl)-amide 7-[2-(4-Dimethylamino-piperidin-1-yl)-pyrimidin-4-yloxy]-1-methyl-1H-indole-2-carboxylic acid (5-tert-butyl-3-methanesulfonylamino-2-methoxy-phenyl)-7-[2-(3-Dimethylamino-pyrrolidin-1-yl)-pyrimidin-4-yloxy]-1-methyl-1H-indole-2-carboxylic acid (5-tert-butyl-3-methanesulfonylamino-2-methoxy-phenyl)-1-Methyl-7-[2-(1-methyl-piperidin-4-ylamino)-pyrimidin-4-yloxy]-1H-indole-2-carboxylic acid (5-tert-butyl-3-methanesulfonylamino-2-methoxy-phenyl)-amide 7-[2-(1-Acetyl-piperidin-4-ylamino)-pyrimidin-4-yloxy]-1-methyl-1H-indole-2-carboxylic acid (5-tert-butyl-3-methanesulfonylamino-2-methoxy-phenyl)-amide 1-Methyl-7-[2-(2-morpholin-4-yl-ethoxy)-pyrimidin-4-yloxy]-1H-indole-2-carboxylic acid (3-methanesulfonylamino-2-methoxy-5-trifluoromethyl-phenyl)-7-[2-(2-Imidazol-1-yl-ethoxy)-pyrimidin-4-yloxy]-1-methyl-1H-indole-2-carboxylic acid (5-tert-butyl-3-methanesulfonylamino-2-methoxy-phenyl)-amide 7-[2-(2-Imidazol-1-yl-ethoxy)-pyrimidin-4-yloxy]-1-methyl-1H-indole-2-carboxylic acid (4-chloro-2-methoxy-5-trifluoromethyl-phenyl)-amide 7-[2-(2-Dimethylamino-ethylamino)-pyrimidin-4-yloxy]-1-methyl-1H-indole-2-carboxylic acid (5-tert-butyl-2-methoxy-3-methylcarbamoyl-phenyl)-amide 7-(2-Amino-pyrimidin-4-yloxy)-1-methyl-1H-indole-2-carboxylic acid (5-tert-butyl-3-carbamoyl-2-methoxy-phenyl)-amide 7-(2-Amino-pyrimidin-4-yloxy)-1-methyl-1H-indole-2-carboxylic acid[5-tert-butyl-3-(2-dimethylamino-ethylcarbamoyl)-2-methoxy-phenyl]-amide 7-[2-(2-Dimethylamino-ethylamino)-pyrimidin-4-yloxy]-1-methyl-1H-indole-2-carboxylic acid (5-tert-butyl-3-dimethylaminomethyl-2-methoxy-phenyl)-amide 7-[2-(2-Dimethylamino-ethylamino)-pyrimidin-4-yloxy]-1-methyl-1H-indole-2-carboxylic acid (5-tert-butyl-2-methoxy-3-pyrrolidin-1-ylmethyl-phenyl)-amide 7-[2-(2-Dimethylamino-ethylamino)-pyrimidin-4-yloxy]-1-methyl-1H-indole-2-carboxylic acid (5-tert-butyl-2-methoxy-3-morpholin-4-ylmethyl-phenyl)-amide 1-Methyl-7-(2-morpholin-4-ylmethyl-pyrimidin-4-yloxy)-1H-indole-2-carboxylic acid (4-chloro-2-methoxy-5-trifluoromethyl-phenyl)-amide 7-[2-(3-Dimethylamino-pyrrolidin-1-ylmethyl)-pyrimidin-4-yloxy]-1-methyl-1H-indole-2-carboxylic acid (5-tert-butyl-3-methanesulfonylamino-2-methoxy-7-(2-Carbamoyl-pyrimidin-4-yloxy)-1-methyl-1H-indole-2-carboxylic acid (5-tert-butyl-3-methanesulfonylamino-2-methoxy-phenyl)-amide 1-Methyl-7-(2-morpholin-4-ylmethyl-pyrimidin-4-yloxy)-1H-indole-2-carboxylic acid (2-methoxy-3-morpholin-4-ylmethyl-5-trifluoromethyl-phenyl)-amide 1-Methyl-7-[2-(4-methyl-piperazin-1-yl)-pyrimidin-4-yloxy]-1H-indole-2-carboxylic acid (2-methoxy-3-morpholin-4-ylmethyl-5-trifluoromethyl-phenyl)-1-Methyl-7-(2-morpholin-4-ylmethyl-pyrimidin-4-yloxy)-1H-indole-2-carboxylic acid (3-methanesulfonylamino-2-methoxy-5-trifluoromethyl-phenyl)-amide 7-(1'-tert-Butyl-1',2',3',4',5',6'-hexahydro-[2,4']bipyridinyl-4-yloxy)-1-methyl-1H-indole-2-carboxylic acid (3-methanesulfonylamino-2-methoxy-5-trifluoromethyl-1-Methyl-7-(2-methylaminomethyl-pyridin-4-yloxy)-1H-indole-2-carboxylic acid (3-methanesulfonylamino-2-methoxy-5-trifluoromethyl-phenyl)-amide 1-Methyl-7-(2-pyrrolidin-1-ylmethyl-pyridin-4-yloxy)-1H-indole-2-carboxylic acid (2-methoxy-3-morpholin-4-ylmethyl-5-trifluoromethyl-phenyl)-amide 1-Methyl-7-[2-(2-morpholin-4-yl-ethyl)-pyrimidin-4-yloxy]-1H-indole-2-carboxylic acid (3-dimethylaminomethyl-2-methoxy-5-trifluoromethyl-phenyl)-1-Methyl-7-(2-pyrrolidin-1-ylmethyl-pyrimidin-4-yloxy)-1H-indole-2-carboxylic acid (2-methoxy-3-pyrrolidin-1-ylmethyl-5-trifluoromethyl-phenyl)-amide 7-(2-Dimethylaminomethyl-pyrimidin-4-yloxy)-1-methyl-1H-indole-2-carboxylic acid[2-methoxy-3-(4-methyl-piperazin-1-ylmethyl)-5-7-(2-Dimethylaminomethyl-pyridin-4-yloxy)-1-methyl-1H-indole-2-carboxylic acid (3-methanesulfonylamino-2-methoxy-5-trifluoromethyl-phenyl)-amide 7-(2-Dimethylaminomethyl-pyrimidin-4-yloxy)-1-methyl-1H-indole-2-carboxylic acid (3-methanesulfonylamino-2-methoxy-5-trifluoromethyl-phenyl)-1-Methyl-7-[2-(4-methyl-piperazin-1-ylmethyl)-pyrimidin-4-yloxy]-1H-indole-2-carboxylic acid (3-methanesulfonylamino-2-methoxy-5-trifluoromethyl-phenyl)-7-(2-Dimethylaminomethyl-pyrimidin-4-yloxy)-1-methyl-1H-indole-2-carboxylic acid (3-methanesulfonylamino-2-methoxy-5-trifluoromethyl-phenyl)-1-Methyl-7-[2-(2-morpholin-4-yl-ethyl)-pyrimidin-4-yloxy]-1H-indole-2-carboxylic acid[3-methanesulfonylamino-2-methoxy-5-(1-methyl-cyclopropyl)-1-Methyl-7-[2-(1-methyl-piperidin-4-yl)-pyrimidin-4-yloxy]-1H-indole-2-carboxylic acid (5-tert-butyl-3-methanesulfonylamino-2-methoxy-phenyl)-amide 7-[2-(1-Cyclopropyl-piperidin-4-yl)-pyrimidin-4-yloxy]-1-methyl-1H-indole-2-carboxylic acid (5-tert-butyl-3-methanesulfonylamino-2-methoxy-phenyl)-amide 1-Methyl-7-[2-(4-methyl-piperazin-1-yl)-pyrimidin-4-yloxy]-1H-indole-2-carboxylic acid (3-dimethylaminomethyl-2-methoxy-5-trifluoromethyl-phenyl)-1-Methyl-7-[2-(1-methyl-pyrrolidin-3-ylamino)-pyridin-4-yloxy]-1H-indole-2-carboxylic acid (5-tert-butyl-3-methanesulfonylamino-2-methoxy-phenyl)-amide or the pharmaceutically acceptable salts or acids thereof.

14. A pharmaceutical composition containing a pharmaceutically effective amount of a compound according to claim 1 and one or more pharmaceutically acceptable carriers and/or adjuvants.

15. A method of treating inflammation comprising administering to a patient a pharmaceutically effective amount of a compound according to claim 1.

16. A process of making a compound of the formula (I):

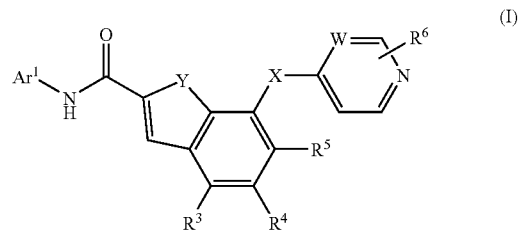

Ar$_1$, X, Y, Q, W, R$^3$, R$^4$, R$^5$, R$^6$ and R$^y$ are defined in claim 1;

said process comprising coupling an amine bearing Ar$^1$ carboxylic acid of the formula (III), where P is a protecting group, removing the protecting group P to provide an intermediate of formula (V);

coupling the intermediate (V) with a halo heterocycle VI (Z=halogen) bearing R$^6$ in the presence of a suitable base to provide a compound of the formula (I):